(12) United States Patent
Wang et al.

(10) Patent No.: US 11,884,612 B2
(45) Date of Patent: Jan. 30, 2024

(54) COVALENT PEPTIDE BINDERS

(71) Applicant: The Regents of the University of California, Oakland, CA (US)

(72) Inventors: Lei Wang, San Francisco, CA (US); Christian Hoppmann, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1100 days.

(21) Appl. No.: 16/085,243

(22) PCT Filed: Mar. 16, 2017

(86) PCT No.: PCT/US2017/022804
§ 371 (c)(1),
(2) Date: Sep. 14, 2018

(87) PCT Pub. No.: WO2017/161183
PCT Pub. Date: Sep. 21, 2017

(65) Prior Publication Data
US 2020/0010411 A1  Jan. 9, 2020

Related U.S. Application Data

(60) Provisional application No. 62/309,356, filed on Mar. 16, 2016.

(51) Int. Cl.
*C07C 311/21* (2006.01)
*C07C 313/02* (2006.01)
*C07K 1/107* (2006.01)

(52) U.S. Cl.
CPC .......... *C07C 311/21* (2013.01); *C07C 313/02* (2013.01); *C07K 1/1075* (2013.01)

(58) Field of Classification Search
None
See application file for complete search history.

(56) References Cited

U.S. PATENT DOCUMENTS

| 4,725,545 A | 2/1988 | Powers |
| 2013/0078671 A1 | 3/2013 | Liu |
| 2015/0094457 A1 | 4/2015 | Miao et al. |

FOREIGN PATENT DOCUMENTS

| EP | 2 221 370 A1 | 8/2010 |
| EP | 2 192 185 B1 | 1/2014 |
| WO | WO-2004/087925 A1 | 10/2004 |
| WO | WO-2015/188120 A1 | 12/2015 |

OTHER PUBLICATIONS

Mokotoff et al. "Potential inhibitors of L-asparagine biosynthesis. 3. Aromatic sulfonyl fluoride analogs of L-asparagine and L-glutamine" Journal of Medicinal Chemistry, 1975, vol. 18, No. 9, pp. 888-891.*
Chen, X.H. et al. (Sep. 19, 2014, e-published Jul. 10, 2014). "Genetically encoding an electrophilic amino acid for protein stapling and covalent binding to native receptors," *ACS Chem Biol.* 9(9):1956-1961.
Chen, W. et al. (Jan. 26, 2016, e-published Dec. 22, 2015). "Synthesis of Sulfotyrosine-Containing Peptides by Incorporating Fluorosulfated Tyrosine Using an Fmoc-Based Solid-Phase Strategy," *Angew Chem Int Ed Intl* 55(5):1835-1838.
Chen, W. et al. (Jun. 15, 2016, e-published Jun. 2, 2016). "Arylfluorosulfates Inactivate Intracellular Lipid Binding Protein(s) through Chemoselective SuFEx Reaction with a Binding Site Tyr Residue," *J Am Chem Soc* 138(23):7353-7364.
Chen, Y. et al. (Feb. 2017, e-published Dec. 9, 2016). "Heritable expansion of the genetic code in mouse and zebrafish," *Cell Res* 27(2):294-297.
Coin, I. et al. (Dec. 5, 2013, e-published Nov. 27, 2013). "Genetically encoded chemical probes in cells reveal the binding path of urocortin-I to CRF class B GPCR," *Cell* 155(6):1258-1269.
Davis, B.G. et al. (1998). "Controlled Site-Selective Glycosylation of Proteins by a Combined Site-Directed Mutagenesis and Chemical Modification Approach," *J Org Chem* 63:9614-9615.
Dong, J. et al. (Sep. 1, 2014, e-published Aug. 11, 2014). "Sulfur(VI) fluoride exchange (SuFEx): another good reaction for click chemistry," *Angew Chem Int Ed Engl* 53(36):9430-9448.
Furman, J.L. et al. (Jun. 11, 2014, e-published May 30, 2014). "A genetically encoded aza-Michael acceptor for covalent cross-linking of protein-receptor complexes," *J Am Chem Soc* 136(23):8411-8417.
Guo, J. et al. (2008). "Site-specific incorporation of methyl- and acetyl-lysine analogues into recombinant proteins," *Angew Chem Int Ed Engl* 47(34):6399-6401.
Hoppmann, C. et al. (Apr. 7, 2014, e-published Mar. 11, 2014). "Genetically Encoding Photoswitchable Click Amino Acids in *Escherichia coli* and Mammalian Cell," *Angew Chem Int Ed Engl.* 53(15):3932-3936.
Hoppmann, C. (Apr. 14, 2016, e-published Mar. 21, 2016). "Proximity-enabled bioreactivity to generate covalent peptide inhibitors of p53-Mdm4. *Chem Commun (Camb)*," 52(29):5140-5143.
Kavran, J.M. et al. (Jul. 3, 2007, e-published Jun. 25, 2007). "Structure of pyrrolysyl-tRNA synthetase, an archaeal enzyme for genetic code innovation," *PNAS USA* 104(27):11268-11273.
Kobayashi,T. et al. (Nov. 16, 2016, e-published Nov. 4, 2016). "Using Protein-Confined Proximity to Determine Chemical Reactivity," *J Am Chem Soc.* 138(45):14832-14835.
Lacey, V.K. et al. (Nov. 4, 2013, e-published Sep. 9, 2013). "Expanding the library and substrate diversity of the pyrrolysyl-tRNA synthetase to incorporate unnatural amino acids containing conjugated rings," *Chembiochem.* 14(16):2100-2105.

(Continued)

*Primary Examiner* — Joseph R Kosack
(74) *Attorney, Agent, or Firm* — Mintz, Levin, Cohn, Ferris, Glovsky and Popeo, P.C.

(57) ABSTRACT

There are provided, inter alia, compositions and methods for covalently binding peptides to proteins.

9 Claims, 11 Drawing Sheets

Specification includes a Sequence Listing.

(56) References Cited

OTHER PUBLICATIONS

Li, H. et al. (Feb. 16, 2007). "The phosphothreonine lyase activity of a bacterial type III effector family," *Science* 315(5814):1000-1003.

Liu, C.C. et al. (2010). Adding new chemistries to the genetic code, *Annu Rev Biochem* 79:413-444.

Parrish, A.R. et al. (2010). "Genetic Incorporation of Unnatural Amino Acids into Proteins," Comprehensive Natural Products Chemistry II Chemistry and Biology 5:587-617.

Parrish, A.R. et al. (Jul. 20, 2012, e-published May 11, 2012). "Expanding the genetic code of Caenorhabditis elegans using bacterial aminoacyl-tRNA synthetase/tRNA pairs," *ACS Chem Biol.* 7(7):1292-1302.

Repka, L.M. et al. (Apr. 26, 2017, e-published Jan. 30, 2017). "Mechanistic Understanding of Lanthipeptide Biosynthetic Enzymes," *Chem Rev* 117(8):5457-5520.

Seebeck, F.P. et al. (Jun. 7, 2006). "Ribosomal synthesis of dehydroalanine-containing peptides," *J Am Chem Soc* 128(22):7150-7151.

Takimoto, J.K. et al. (Sep. 2009, e-published Jul. 2, 2009). "Improving orthogonal tRNA-synthetase recognition for efficient unnatural amino acid incorporation and application in mammalian cells," *Mol Biosyst.* 5(9):931-934.

Takimoto, J.K. (Jul. 15, 2011, e-published May 5, 2011). "Stereochemical basis for engineered pyrrolysyl-tRNA synthetase and the efficient in vivo incorporation of structurally divergent non-native amino acids," *ACS Chem Biol* 6(7):733-743.

Wan, W. et al. (Jun. 2014, e-published Mar. 12, 2014). "Pyrrolysyl-tRNA synthetase: an ordinary enzyme but an outstanding genetic code expansion tool," *Biochim Biophys Acta* 1844(6):1059-1070.

Wang, L. et al. (May 4, 2000). "A New Functional Suppressor tRNA/Aminoacyl-tRNA Synthetase Pair for the in vivo Incorporation of Unnatural Amino Acids into Proteins," *J Am Chem Soc.* 122(20):5010-5011.

Wang, L. (Sep. 25, 2017, e-published Oct. 6, 2016). "Genetically encoding new bioreactivity," *N. Biotechnol.* 38(Pt A):16-25.

Wang, L. et al. (Apr. 20, 2001). "Expanding the genetic code of Escherichia coli," *Science* 292(5516):498-500.

Wang, L. et al. (Dec. 17, 2004). "Expanding the genetic code," *Angew Chem Int Ed Engl* 44(1):34-66.

Wang, L. et al. (2006). "Expanding the genetic code," *Annu Rev Biophys Biomol Struct* 35:225-249.

Wang, J. et al. (2007). "A biosynthetic route to dehydroalanine-containing proteins," *Angew Chem Int Ed Engl* 46(36):6849-6851.

Wang, W. et al. (Aug. 2007). "Genetically encoding unnatural amino acids for cellular and neuronal studies," *Nat Neurosci* 10(8):1063-1072.

Wang, Z.U. et al. (Jul. 3, 2012). "A facile method to synthesize histones with posttranslational modification mimics," *Biochemistry* 51(26):5232-5234.

Wright, T.H. et al. (Nov. 4, 2016, e-published Sep. 22, 2016). "Posttranslational mutagenesis: A chemical strategy for exploring protein side-chain diversity," *Science* 354 (6312):aag1465.

Xiang, Z. et al. (Sep. 2013, e-published Aug. 4, 2013). "Adding an unnatural covalent bond to proteins through proximity-enhanced bioreactivity," *Nat Methods.* 10(9):885-888.

Xiang, Z. et al. (Feb. 17, 2014, e-published Jan. 21, 2014). "Proximity-enabled protein crosslinking through genetically encoding haloalkane unnatural amino acids," *Angew Chem Int Ed Engl.* 53(8):2190-2193.

Xie, J. et al. (Oct. 2004, e-published Sep. 19, 2004). "The site-specific incorporation of p-iodo-L-phenylalanine into proteins for structure determination," *Nat Biotechnol.* 22(10):1297-1301.

Yang, A. et al. (Nov. 4, 2016, e-published Sep. 29, 2016). "A chemical biology route to site-specific authentic protein modifications," *Science* 354(6312):623-626.

Chern, J.W. et al. (Apr. 16, 1993). "Nucleosides. 5. Synthesis of guanine and formycin B derivatives as potential inhibitors of purine nucleoside phosphorylase," *J Med Chem* 36(8):1024-1031.

International Search Report dated Jul. 19, 2017, for PCT Application No. PCT/US2017/022804, filed Mar. 16, 2017, 5 pages.

PubChem CID 316445 (Mar. 26, 2005), 13 pages.

PubChem CID 54079384 (Dec. 4, 2011). 10 pages.

Written Opinion dated Jul. 19, 2017, for PCT Application No. PCT/US2017/022804, filed Mar. 16, 2017, 4 pages.

\* cited by examiner

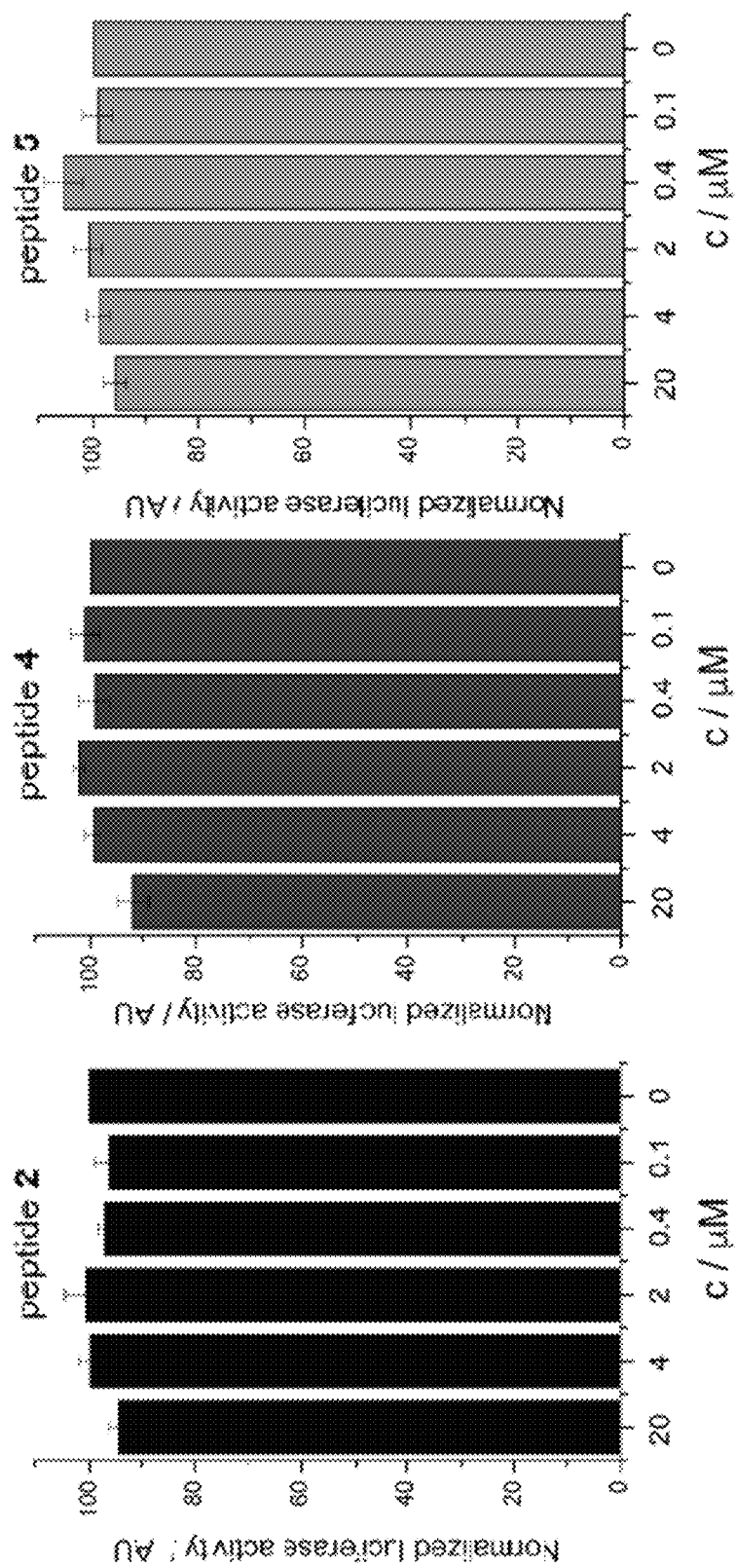

```
                         SEQUENCE LISTING

<160> NUMBER OF SEQ ID NOS: 8

<210> SEQ ID NO 1
<211> LENGTH: 88
<212> TYPE: PRT
<213> ORGANISM: Homo sapiens

<400> SEQUENCE: 1

Met Gln Glu Thr Leu Val Arg Pro Lys Pro Leu Leu Leu Lys Leu Leu
1               5                   10                  15

Lys Ser Val Gly Ala Gln Lys Asp Thr Tyr Thr Met Lys Glu Val Leu
            20                  25                  30

Phe Tyr Leu Gly Gln Tyr Ile Met Thr Lys Arg Leu Tyr Asp Glu Lys
        35                  40                  45

Gln Gln His Ile Val Tyr Cys Ser Asn Asp Leu Leu Gly Asp Leu Phe
    50                  55                  60

Gly Val Pro Ser Phe Ser Val Lys Glu His Arg Lys Ile Tyr Thr Met
65                  70                  75                  80

Ile Tyr Arg Asn Leu Val Val Val
                85

<210> SEQ ID NO 2
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (7)..(7)
<223> OTHER INFORMATION: Residue is (2R)-2-amino-2-methylnonanoic acid
<220> FEATURE:
<221> NAME/KEY: MOD_RES
<222> LOCATION: (14)..(14)
<223> OTHER INFORMATION: Residue is 2-methyl-L-norleucine

<400> SEQUENCE: 2

Gln Ser Gln Gln Thr Phe Xaa Asn Leu Trp Arg Leu Leu Xaa Gln Asn
1               5                   10                  15
```

```
<210> SEQ ID NO 3
<211> LENGTH: 130
<212> TYPE: PRT
<213> ORGANISM: Homo sapiens

<400> SEQUENCE: 3

Met Ala His His His His His His Val Asp Asp Asp Lys Ile Arg
1               5                   10                  15

Thr Leu Pro Gly Glu Gly Thr Gln Val His Pro Arg Ala Pro Leu Leu
            20                  25                  30

Gln Ile Leu Lys Val Ala Gly Ala Gln Glu Glu Val Phe Thr Val Lys
                35                  40                  45

Glu Val Met His Tyr Leu Gly Gln Tyr Ile Met Met Lys Gln Leu Tyr
            50                  55                  60

Asp Lys Gln Arg Gln His Ile Val His Cys His Asp Asp Pro Leu Gly
65                  70                  75                  80

Glu Leu Leu Glu Val Gly Ser Phe Ser Val Lys Asn Pro Ser Pro Leu
                85                  90                  95

Tyr Glu Met Leu Lys Arg Asn Leu Val Ile Leu Asn Asn Ser Asp Ala
            100                 105                 110

Ala Lys Asn Leu Ser Val Gly Lys Asp Ser Asn Glu Ser Pro Ser Glu
        115                 120                 125

Asp Pro
    130

<210> SEQ ID NO 4
<211> LENGTH: 21
<212> TYPE: PRT
<213> ORGANISM: Homo sapiens

<400> SEQUENCE: 4

Glu Thr Phe Ser Asp Leu Trp Lys Leu Leu Pro Glu Asn Asn Val Leu
1               5                   10                  15

Ser Pro Leu Pro Ser
            20

<210> SEQ ID NO 5
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: Residue is (2R)-2-amino-2-methylnonanoic acid
<220> FEATURE:
<221> NAME/KEY: MOD_RES
<222> LOCATION: (14)..(14)
<223> OTHER INFORMATION: Residue is 2-methyl-L-norleucine
<220> FEATURE:
<221> NAME/KEY: MOD_RES
<222> LOCATION: (16)..(16)
<223> OTHER INFORMATION: AMIDATION

<400> SEQUENCE: 5

Gln Ser Gln Gln Thr Phe Xaa Asn Leu Trp Arg Leu Leu Xaa Gln Asn
1               5                   10                  15
```

```
<210> SEQ ID NO 6
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: Residue is (2R)-2-amino-2-methylnonanoic acid
<220> FEATURE:
<221> NAME/KEY: MOD_RES
<222> LOCATION: (9)..(9)
<223> OTHER INFORMATION: Residue is 2-amino-3-(4-
      (fluorosulfonyl)benzamido)propanoic acid
<220> FEATURE:
<221> NAME/KEY: MOD_RES
<222> LOCATION: (14)..(14)
<223> OTHER INFORMATION: Residue is 2-methyl-L-norleucine
<220> FEATURE:
<221> NAME/KEY: MOD_RES
<222> LOCATION: (16)..(16)
<223> OTHER INFORMATION: AMIDATION

<400> SEQUENCE: 6

Gln Ser Gln Gln Thr Phe Xaa Asn Xaa Trp Arg Leu Leu Xaa Gln Asn
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: Residue is (2R)-2-amino-2-methylnonanoic acid
<220> FEATURE:
<221> NAME/KEY: MOD_RES
<222> LOCATION: (9)..(9)
<223> OTHER INFORMATION: Residue is 2-amino-3-(3-
      (fluorosulfonyl)benzamido)propanoic acid
<220> FEATURE:
<221> NAME/KEY: MOD_RES
<222> LOCATION: (14)..(14)
<223> OTHER INFORMATION: Residue is 2-methyl-L-norleucine
<220> FEATURE:
<221> NAME/KEY: MOD_RES
<222> LOCATION: (16)..(16)
<223> OTHER INFORMATION: AMIDATION

<400> SEQUENCE: 7

Gln Ser Gln Gln Thr Phe Xaa Asn Xaa Trp Arg Leu Leu Xaa Gln Asn
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (7)..(7)
<223> OTHER INFORMATION: Residue is (2R)-2-amino-2-methylnonanoic acid
<220> FEATURE:
<221> NAME/KEY: MOD_RES
<222> LOCATION: (9)..(9)
<223> OTHER INFORMATION: Residue is 2-amino-3-(3-
      (fluorosulfonyl)benzamido)propanoic acid
<220> FEATURE:
<221> NAME/KEY: MOD_RES
<222> LOCATION: (14)..(14)
<223> OTHER INFORMATION: Residue is 2-methyl-L-norleucine
<220> FEATURE:
<221> NAME/KEY: MOD_RES
<222> LOCATION: (16)..(16)
<223> OTHER INFORMATION: AMIDATION

<400> SEQUENCE: 8

Gln Ser Gln Gln Thr Ala Xaa Asn Xaa Trp Arg Leu Leu Xaa Gln Asn
1               5                   10                  15
```

COVALENT PEPTIDE BINDERS

CROSS-REFERENCES TO RELATED APPLICATIONS

This application is a Section 371 US national phase of International Application No. PCT/US2017/22804 filed Mar. 16, 2017, which claims the benefit of priority to U.S. Provisional Application No. 62/309,356, filed Mar. 16, 2016, the contents of which are incorporated hereby by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 48536-582001WO_ST25.TXT, created Mar. 16, 2017, 5,556 bytes, machine format IBM-PC, MS-Windows operating system, is hereby incorporated by reference.

BACKGROUND

Small molecule drugs can be classified as covalent or non-covalent depending upon the chemical bonding rearrangements, if any, that occur upon interaction with a target biomolecule. Macromolecule drugs, however, are largely non-covalent. Indeed, in comparison with macromolecule non-covalent drugs, macromolecular covalent drugs can irreversibly bind to target biomolecule, thus increasing binding affinity, biological activity and potency. Although small molecule covalent modulators (e.g., inhibitors and activators) have been widely explored, macromolecular covalent inhibitors are more difficult to design and implement.

There are provided inter alia solutions to these and other problems in the art.

SUMMARY

Provided herein, inter alia, are compounds and strategies to enable a peptide to bind to its target protein covalently via proximity-enabled bioreactivity.

In a first aspect, there is provided a compound of Formula (III):

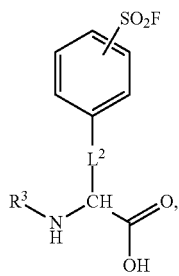

(III)

wherein: $R^3$ is hydrogen or an amino protecting group; $L^2$ is a bond, —S(O)$_2$—, —NH—, —O—, —S—, —C(O)—, —NHC(O)—, —C(O)NH—, —NHC(O)NH—, —C(O)O—, —OC(O)—, —NHS(O)$_2$—, —S(O)$_2$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In another aspect, there is provided a compound of Formula (IV):

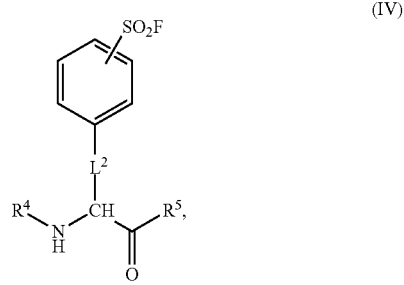

(IV)

wherein: $R^4$ is a first peptidyl moiety; $R^5$ is a second peptidyl moiety; and $L^2$ is a bond, —S(O)$_2$—, —NH—, —O—, —S—, —C(O)—, —NHC(O)—, —C(O)NH—, —NHC(O)NH—, —C(O)O—, —OC(O)—, —NHS(O)$_2$—, —S(O)$_2$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In another aspect, there is provided a compound of Formula (V):

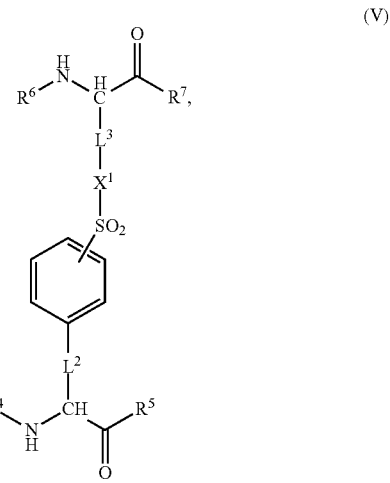

(V)

wherein: $R^4$ is a first peptidyl moiety; $R^5$ is a second peptidyl moiety; $R^6$ is a third peptidyl moiety; $R^7$ is a fourth peptidyl moiety; $L^2$ and $L^3$ are independently a bond, —S(O)$_2$—, —NH—, —O—, —S—, —C(O)—, —NHC(O)—, —C(O)NH—, —NHC(O)NH—, —C(O)O—, —OC(O)—, —NHS(O)$_2$—, —S(O)$_2$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $X^1$ is —NH—, —O—, or —S—.

In another aspect, there is provided a method of covalently binding a peptide to a protein, the method comprising combining a compound of Formula (IV):

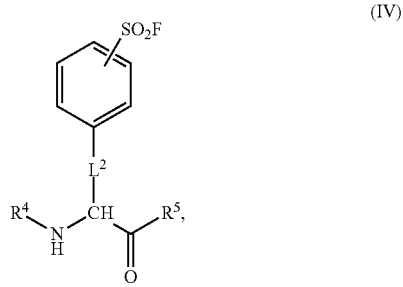

with a protein, thereby forming a compound of Formula (V):

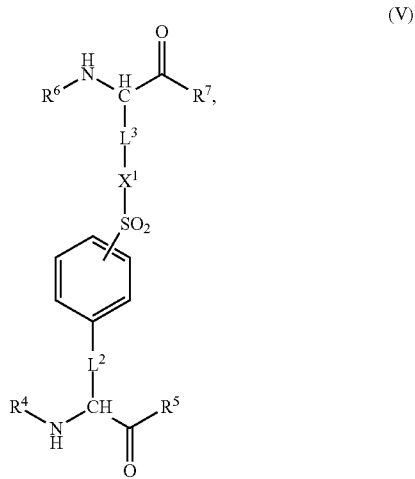

wherein: $R^4$ is a first peptidyl moiety; $R^5$ is a second peptidyl moiety; $R^6$ is a third peptidyl moiety; $R^7$ is a fourth peptidyl moiety; $L^2$ and $L^3$ are independently a bond, —S(O)$_2$—, —NH—, —O—, —S—, —C(O)—, —NHC(O)—, —C(O)NH—, —NHC(O)NH—, —C(O)O—, —OC(O)—, —NHS(O)$_2$—, —S(O)$_2$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $X^1$ is —NH—, —O—, or —S—.

BRIEF DESCRIPTION OF THE DRAWINGS

FIG. 2A) Unnatural amino acid (Uaa) 1 with aryl sulfonyl fluoride as crosslinking unit reactive with lysine and histidine. Reaction with lysine is shown. FIG. 2B) Crystal structure of Mdm2 in complex with the stapled peptide SAHp53-8 (top panel, PDB code 3V3B) (SEQ ID NOS:1-2) and of Mdm4 in complex with a 15-residue transactivation domain peptide of p53 (bottom panel, PDB code 3DAC) (SEQ ID NOS:3-4). L22 in the peptide was substituted by Uaa 1 to target the natural amino acids highlighted (H73, K94 and H96 in Mdm2; H69 and K90 in Mdm4). FIG. 2C) Structures of stapled peptides disclosed herein. Sequence legend: Peptides 2, 3, 4 and 5 (SEQ ID NOS:5-8, respectively). FIG. 2D) Schematic representation of the synthesis of stapled peptides with Ar—SO$_2$F "click" function.

FIGS. 3A-3D. ReBiL assay reveals that the stapled peptide 4 with SuFEx inhibited the p53-Mdm4 interaction more efficiently than the parental stapled peptide SAHp53-8 2. FIG. 3A) Scheme showing the mechanism of ReBiL assay [12]. FIG. 3B) ReBiL assay of peptide inhibition of p53-Mdm2 interaction in cell lysates of Saos-2 cells. 2: IC$_{50}$=4.1 μM; 4: IC$_{50}$=1.3 μM; 5: no inhibition. FIG. 3C) ReBiL assay of peptide inhibition of p53-Mdm4 interaction in cell lysates of Saos-2 cells. 2: IC$_{50}$=3.6 μM; 4: IC$_{50}$=0.2 μM; 5: no inhibition. FIG. 3D) ReBiL assay of peptide inhibition of Brca1-Bard1 interaction in cell lysates of Saos-2 cells. No inhibition was detected for all peptides tested. Data are shown as mean±s.e.m. (n=5) and normalized to the luminescent reading of DMSO treated cells. "S.E.M" refers to the standard error of the mean.

DETAILED DESCRIPTION

Definitions

Figure 1:
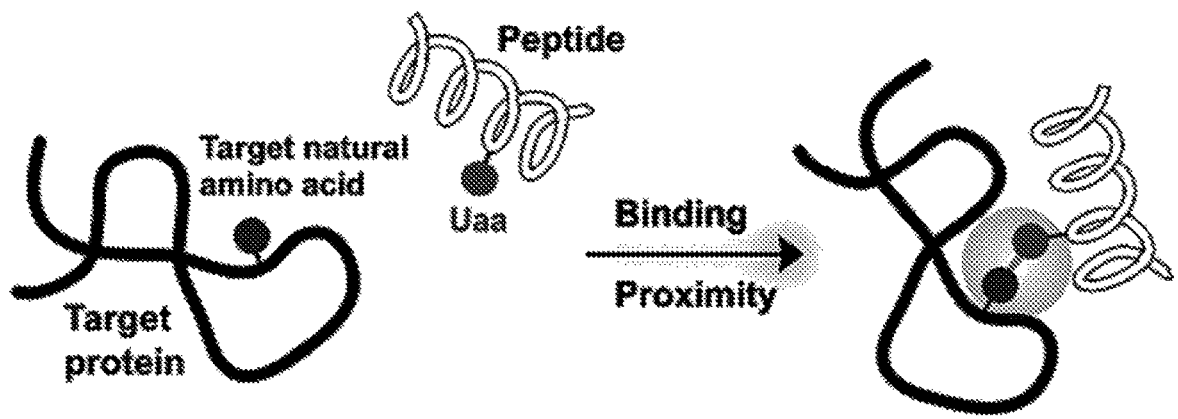
FIG. 1. Schematic depicting covalent crosslinking of a peptide to its target protein via proximity-enabled bioreactivity.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds (e.g., alkene, alkyne). Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. Heteroalkyl is not cyclized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

The term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded ("=O") to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C($O_2$)R', —NR—C(NR'R")=NR''', —S(O)R', —S($O_2$)R', —S($O_2$)N(R)('R"—NRS$O_2$R'), —CN, and —$NO_2$ in a number ranging from zero to (2m'+1), where m' is the total number of carbon atoms in such radical. R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R'", NR"C(O)$_2$R', NRC(NR'R")=NR'", S(O)R', —S(O)$_2$R', —S(O)$_2$N(R')(R", —NRSO$_2$R'), —CN, —NO$_2$, —R', —N$_3$, —CH(Ph)$_2$, fluoro(C$_1$-C$_4$)alkoxy, and fluoro (C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Where a moiety is substituted with an R substituent, the group may be referred to as "R-substituted." Where a moiety is R-substituted, the moiety is substituted with at least one R substituent and each R substituent is optionally different. For example, where a moiety herein is R$^{14}$-substituted or unsubstituted alkyl, a plurality of R$^{14}$ substituents may be attached to the alkyl moiety wherein each R$^{14}$ substituent is optionally different. Where an R-substituted moiety is substituted with a plurality R substituents, each of the R-substituents may be differentiated herein using a prime symbol (') such as R', R", etc. For example, where a moiety is R$^{14}$-substituted or unsubstituted alkyl, and the moiety is substituted with a plurality of R$^{14}$ substituents, the plurality of R$^{14}$ substituents may be differentiated as R$^{14'}$, R$^{14''}$, R$^{14'''}$, etc. In some embodiments, the plurality of R substituents is 3. In some embodiments, the plurality of R substituents is 2.

In embodiments, a compound as described herein may include multiple instances of R$^1$, R$^2$, and/or other substituents and variables. In such embodiments, each variable may optional be different and be appropriately labeled to distinguish each group for greater clarity. For example, where each R$^{64}$ is different, they may be referred to, for example, as R$^{64.1}$, R$^{64.2}$, R$^{64.3}$, or R$^{64.4}$, respectively, wherein the definition of R$^{64}$ is assumed by R$^{64.1}$, R$^{64.2}$, R$^{64.3}$, and/or R$^{64.4}$. The variables used within a definition of R$^1$, R$^2$, and/or other variables that appear at multiple instances and are different may similarly be appropriately labeled to distinguish each group for greater clarity.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In embodiments, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where variables s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, In embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth in the Examples section below.

The term "protecting group," or the like refer, in the usual and customary sense, to chemical moieties which can temporarily mask a functional group to allow regio-selective bond formation, as well known in the art. The term "amino protecting group," or the like refer, in the usual and customary sense, to chemical moieties which can temporarily mask an amine functional group to allow regio-selective bond formation, as well known in the art. In embodiments, the amino protecting groups is a chemical moiety which can temporarily mask an amine functional group to allow regio-selective bond formation during peptide synthesis (e.g., solid phase peptide synthesis). Exemplary amino protecting groups include: tert-butyloxycarbonyl (tBoc), trityl, α,α-dimethyl-3,5-dimethoxybenzyloxycarbonyl (Ddz), Propargyloxycarbonyl (Poc), 2-(4-Biphenyl) isopropoxycarbonyl (Bpoc), 2-Nitrophenylsulfenyl (Nps), 9H-fluoren-9-yl-methoxycarbonyl (Fmoc), 2-(4-Nitrophenylsulfonyl) ethoxycarbonyl (Nsc), 2,7-Di-tert-butyl-Fmoc (Fmoc*), (1,1-Dioxobenzo[b]thiophene-2-yl) methyloxycarbonyl (Bsmoc), (1,1-dioxonaphtho[1,2-b]thiophene-2-yl)methyloxycarbonyl (α-Nsmoc), 2-fluoro-Fmoc (Fmoc(2F)), 2-Monoisooctyl-Fmoc (mio-Fmoc) and 2,7-Diisooctyl-Fmoc (dio-Fmoc), Tetrachlorophthaloyl (TCP), 2-[Phenyl (methyl) sulfonio]ethyloxycarbonyl tetrafluoroborate (Pms), ethanesulfonylethoxycarbonyl (Esc), benzyloxy-carbonyl (Z), allyloxycarbonyl (Alloc), 4-methyltriryl (Mtt), 1-(4,4-Dimethyl-2,6-dioxocyclohex-1-ylidene)-3-ethyl (Dde), or 1-(4,4-Dimethyl-2,6-dioxocyclohex-1-ylidene)-3-methyl-butyl (ivDde), 2-(4-Sulfophenylsulfonyl) ethoxycarbonyl (Sps), 2,4-Dinitrobenzenesulfonyl (dNBS), benzothiazole-2-sulfonyl (Bts), 2,2,2-Trichloroethyloxycarbonyl (Troc), dithiasuccinoyl (Dts), 2-(2-Nitrophenyl)propyloxycarbonyl (NPPOC), 2-(3,4-Methylenedioxy-6-nitrophenyl) propyloxycarbonyl (MNPPOC), 9-(4-Bromophenyl)-9-fluorenyl (BrPhF), or Azidomethoxycarbonyl (Azoc).

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g., compounds, drugs, therapeutic agents) that may be in a prodrug form. Prodrugs of the compounds described herein are those compounds that readily undergo chemical changes under select physiological conditions to provide the final agents (e.g., compounds, drugs, therapeutic agents). Additionally, prodrugs can be converted to agents (e.g., compounds, drugs, therapeutic agents) by chemical or biochemical methods in an ex vivo environment. Prodrugs described herein include compounds that readily undergo chemical changes under select physiological conditions to provide agents (e.g., compounds, drugs, therapeutic agents) to a biological system (e.g., in a subject, in a cell, in the extracellular space near a cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "therapeutically effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g., infectious disease, hyperproliferative disease, cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with infection may be treated with an agent (e.g., compound as described herein) effective as an antibiotic.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, metastatic bone cancer, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer "Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As defined herein, the term "inhibition", "inhibit", "inhibiting" and the like in reference to a protein-inhibitor interaction means negatively affecting (e.g., decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

The term "activation", "activate", "activating" and the like in reference to a protein refers, in the usual and customary sense, to positively affecting (e.g., increasing) the activity or function of the protein relative to the activity or function of the protein in the absence of the positively affecting agent. In embodiments, activation refers to an increase in the activity of a particular protein. Thus, activation includes, at least in part, partially or fully increasing stimulation, increasing, allowing, or expediting activation, or activating, sensitizing, or up-regulating signal transduction or enzymatic activity or the amount of a protein.

The term "modulator," "modulating" and the like refer, in the usual and customary sense, to an agent capable of inhibiting or activating the function, amount, or biological activity of the species being modulated. The term "species being modulated" and the like refers, in the usual and customary sense, to a chemical species (e.g., biomolecule), cell, or the like having a biological activity or function capable of being increased or decreased. In embodiments, the modulator is an inhibitor, and the modulated agent is reduced in activity or function (e.g., protein biological activity including binding to another protein). In embodiments, the modulator is an activator, and the modulated agent is increased in activity or function (e.g., protein biological activity).

"Contacting" is used in accordance with its plain ordinary meaning and refers to the process of allowing at least two distinct species (e.g., chemical compounds including biomolecules, cells, compound disclosed herein, or the like) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway or regulatory pathway.

As used herein, "biomolecule" is used in its customary sense and refers to a molecule found in nature or derivatives thereof, including macromolecules such as proteins, carbohydrates, lipids, and nucleic acids, as well as small molecules such as primary metabolites, secondary metabolites, and natural products. A biomolecule may be present as a moiety attached to the remainder of a compound. A biomolecule includes but is not limited to nucleic acids (e.g., DNA and RNA), peptide nucleic acids, sugars, peptides, proteins, antibodies, lipids, small molecule affinity ligands, e.g., inhibitors, biotin and haptens. Absent express indication otherwise, term "small molecule" generally refers to a chemical species having a molecular weight of about 500 Dalton or less, e.g., 500, 400 m, 300, 200, 100 Dalton, or even less. The term "target biomolecule" and like refer, in the usual and customary sense, to a biomolecule which can be targeted for covalent or non-covalent interaction with another biomolecule, a small molecule, or a chemical moiety disclosed herein and derivatives thereof. In embodiments, the biological activity of the target biomolecule is modulated (e.g., increased or decreased) upon interaction with a targeting agent, e.g., another biomolecule, a small molecule, or a chemical moiety disclosed herein and derivatives thereof. In embodiments, the biological activity (e.g., binding to another biomolecule, enzymatic activity, and the like) of the target biomolecule is increased upon interaction with a targeting agent. In embodiments, the biological activity of the target biomolecule is decreased upon interaction with a targeting agent. In embodiments, the targeting agent is a compound or moiety disclosed herein. The term "macromolecule" and like refers, in the usual and customary sense, to a chemical species, e.g., biomolecule, having a molecular weight greater than 500 Dalton. The term "macromolecule drug" refers, in the usual and customary sense, to a medicament including a macromolecule. The term "non-covalent" in the context of macromolecule drug refers to a macromolecule drug which does not covalently attach to a target. Conversely, the term "covalent" in the context of a macromolecule drug refers to a macromolecule drug which covalently attached to a target.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g., to reduce metabolic degradation).

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

The term "associated" or "associated with" in the context of a substance or substance activity or function associated with a disease means that the disease is caused by or otherwise characterized by (in whole or in part), a symptom of the disease is caused by (in whole or in part) the substance or substance activity or function, or a side-effect of the compound (e.g., toxicity) is caused by or characterized by (in whole or in part) the substance or substance activity or function.

An "agonist," as used herein, refers to a compound capable of detectably increasing the expression or activity of a given protein or receptor. The agonist can increase expression or activity 10%, 20%, 30%, 40%, 50%, 60%, 70%, 80%, 90%, 100% or more in comparison to a control in the absence of the agonist. In embodiments, expression or activity is 1.5-fold, 2-fold, 3-fold, 4-fold, 10-fold or more higher than the expression or activity in the absence of the agonist.

The term "antagonist" refers to a substance capable of detectably lowering expression or activity of a given protein. The antagonist can inhibit expression or activity 10%, 20%, 30%, 40%, 50%, 60%, 70%, 80%, 90%, 100% or less in comparison to a control in the absence of the antagonist. In embodiments, the inhibition is 1.5-fold, 2-fold, 3-fold, 4-fold, 5-fold, 10-fold, or more than the expression or activity in the absence of the antagonist.

The term "proximity-enabled bioreactivity" refers to modulation (e.g., activation or inhibition) of a target protein which is facilitated by proximity in three-dimensional space of a modulating moiety, (e.g., a protein binding moiety as disclosed herein and derivatives thereof) with a target protein. In embodiments, the proximity-enabled bioreactivity is sufficient to afford covalent linkage of the modulating moiety with the target protein.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "polypeptide," "peptide" and "protein" and the like are used interchangeably herein to refer, in the usual and customary sense, to a polymer of amino acid residues. In embodiments, the polymer can be conjugated to a moiety that does not consist of amino acids. In embodiments, the terms apply to amino acid polymers of naturally occurring amino acids (e.g., Ala, Cys, Asp, Glu, Phe, Gly, His, Ile, Lys, Leu, Met, Asn, Pro, Gln, Arg, Ser, Thr, Val, Trp, or Tyr). In embodiments, the terms apply to amino acid polymers in which one or more amino acid residue is an artificial chemical mimetic of a naturally occurring amino acid. In embodiments, the terms apply to naturally occurring amino acid polymers and non-naturally occurring amino acid polymers.

The term "peptidyl" or "peptidyl moiety" refers, in the usual and customary sense, to a monovalent peptide attached to the remainder of a molecule.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "about" in the context of a numeric value means, unless indicated otherwise, the nominal numeric value ±10% thereof Compositions In a first aspect, there is provided a compound of Formula (III):

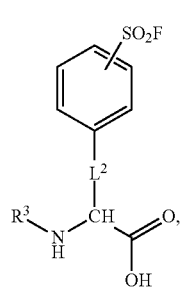

(III)

wherein: $R^3$ is hydrogen or an amino protecting group; $L^2$ is a bond, —S(O)$_2$—, —NH—, —O—, —S—, —C(O)—, —NHC(O)—, —C(O)NH—, —NHC(O)NH—, —C(O)O—, —OC(O)—, —NHS(O)$_2$—, —S(O)$_2$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^2$ is substituted or unsubstituted alkyl. In embodiments, $L^2$ is substituted or unsubstituted $C_1$-$C_{10}$ alkyl. In embodiments, $L^2$ is unsubstituted $C_1$-$C_{10}$ alkyl. In embodiments, $L^2$ is methylene.

In embodiments, $L^2$ is substituted or unsubstituted heteroalkyl. In embodiments, said $L^2$ is substituted or unsubstituted 2 to 10 membered heteroalkyl. In embodiments, $L^2$ is unsubstituted 2 to 10 membered heteroalkyl. In embodiments, $L^2$ is oxo substituted 2 to 10 membered heteroalkyl. In embodiments, said $L^2$ is —(CH$_2$)$_n$—NH—C(O)—, wherein n is an integer in the range 1-10. In embodiments, n is 1, 2, 3, 4, 5, 6, 7, 8, 9 or 10. In embodiments, n is 1. In embodiments, n is 2. In embodiments, n is 3. In embodiments, n is 4. In embodiments, n is 5. In embodiments, n is 6. In embodiments, n is 7. In embodiments, n is 8. In embodiments, n is 9. In embodiments, n is 10.

In embodiments, the compound of Formula (III) has the structure of Formula (IIIa):

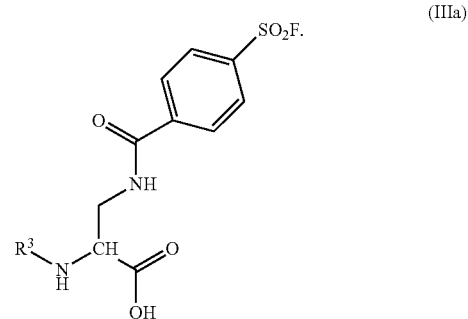

(IIIa)

In embodiments, $R^3$ is hydrogen.

In embodiments, $R^3$ is an amino protecting group. In embodiments, the amino protecting group is tert-butyloxycarbonyl (tBoc), 9H-fluoren-9-ylmethoxycarbonyl (Fmoc), benzyloxy-carbonyl (Z), allyloxycarbonyl (Alloc), 4-methyltrityl (Mtt), 1-(4,4-Dimethyl-2,6-dioxocyclohex-1-ylidene)-3-ethyl (Dde), or 1-(4,4-Dimethyl-2,6-dioxocyclohex-1-ylidene)-3-methylbutyl (ivDde). In embodiments, the amino protecting group is Fmoc.

In another aspect, there is provided a compound of Formula (IV):

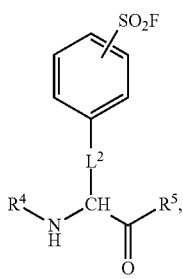

(IV)

wherein: $R^4$ is a first peptidyl moiety; $R^5$ is a second peptidyl moiety; and $L^2$ is a bond, —S(O)$_2$—, —NH—, —O—, —S—, —C(O)—, —NHC(O)—, —C(O)NH—, —NHC(O)NH—, —C(O)O—, —OC(O)—, —NHS(O)$_2$—, —S(O)$_2$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^2$ is substituted or unsubstituted alkyl. In embodiments, $L^2$ is substituted or unsubstituted $C_1$-$C_{10}$ alkyl. In embodiments, $L^2$ is unsubstituted $C_1$-$C_{10}$ alkyl. In embodiments, $L^2$ is methylene.

In embodiments, $L^2$ is substituted or unsubstituted heteroalkyl. In embodiments, $L^2$ is substituted or unsubstituted $C_1$-$C_{10}$ heteroalkyl. In embodiments, $L^2$ is unsubstituted $C_1$-$C_{10}$ heteroalkyl. In embodiments, $L^2$ is substituted $C_1$-$C_{10}$ heteroalkyl. In embodiments, $L^2$ is —(CH$_2$)$_n$—NH—C(O)—, wherein n is an integer in the range 1-10. In embodiments, n is 1, 2, 3, 4, 5, 6, 7, 8, 9 or 10. In embodiments, n is 1. In embodiments, n is 2. In embodiments, n is 3. In embodiments, n is 4. In embodiments, n is 5. In embodiments, n is 6. In embodiments, n is 7. In embodiments, n is 8. In embodiments, n is 9. In embodiments, n is 10.

In embodiments, the compound has the structure of Formula (Iva):

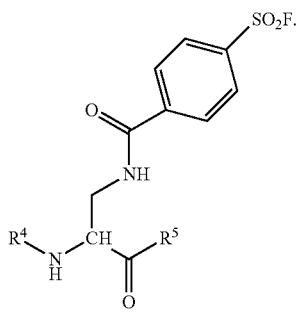

(IVa)

In another aspect, there is provided a compound of Formula (V):

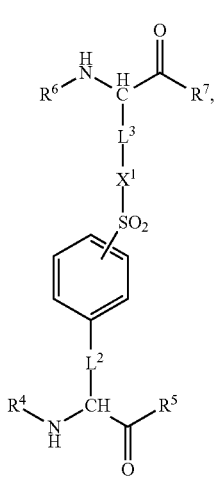

(V)

wherein: $R^4$ is a first peptidyl moiety; $R^5$ is a second peptidyl moiety; $R^6$ is a third peptidyl moiety; $R^7$ is a fourth peptidyl moiety; $L^2$ and $L^3$ are independently a bond, —S(O)$_2$—, —NH—, —O—, —S—, —C(O)—, —NHC(O)—, —C(O)NH—, —NHC(O)NH—, —C(O)O—, —OC(O)—, —NHS(O)$_2$—, —S(O)$_2$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $X^1$ is —NH—, —O—, or —S—. In embodiments, $X^1$ and $L^3$ together form a divalent amino acid side chain moiety (e.g., the reacted product of an amino acid side chain).

In embodiments, $L^2$ is substituted or unsubstituted alkyl. In embodiments, $L^2$ is substituted or unsubstituted $C_1$-$C_{10}$ alkyl. In embodiments, $L^2$ is unsubstituted $C_1$-$C_{10}$ alkyl. In embodiments, $L^2$ is methylene.

In embodiments, $L^2$ is substituted or unsubstituted heteroalkyl. In embodiments, $L^2$ is substituted or unsubstituted $C_1$-$C_{10}$ heteroalkyl. In embodiments, $L^2$ is unsubstituted $C_1$-$C_{10}$ heteroalkyl. In embodiments, $L^2$ is substituted $C_1$-$C_{10}$ heteroalkyl. In embodiments, $L^2$ is —(CH$_2$)$_n$—NH—C(O)—, wherein n is an integer in the range 1-10. In embodiments, n is 1, 2, 3, 4, 5, 6, 7, 8, 9 or 10. In embodiments, n is 1. In embodiments, n is 2. In embodiments, n is 3. In embodiments, n is 4. In embodiments, n is 5. In embodiments, n is 6. In embodiments, n is 7. In embodiments, n is 8. In embodiments, n is 9. In embodiments, n is 10.

In embodiments, -$L^3$-$X^1$— is the reacted product of a lysine side chain, histidine side chain, cysteine side chain, serine side chain, threonine side chain or tyrosine side chain. The term "reacted product," "reacted product of an amino acid side chain," or the like refers to the product of a reaction between the recited amino acid chain side and the —SO$_2$F (sulfonyl fluoride) group (e.g., of the compound of Formula III or IV or embodiments thereof). In embodiments, the reaction occurs between sulfonyl fluoride and the side chain nitrogen of lysine, a side chain nitrogen of histidine, the side chain sulfur of cysteine, or the side chain oxygen of serine, threonine, or tyrosine. Thus, in embodiments the amino acid side chain that reacts with the sulfonyl fluoride is a lysine side chain, histidine side chain, cysteine side chain, serine side chain, threonine side chain or tyrosine side chain.

In embodiments, -$L^3$-$X^1$— is the reacted product of a lysine side chain. In embodiments, -$L^3$-$X^1$— is the reacted product of a cysteine side chain. In embodiments, -$L^3$-$X^1$— is the reacted product of a serine, threonine or tyrosine side chain. In embodiments, -$L^3$-$X^1$— is the reacted product of a serine side chain. In embodiments, -$L^3$-$X^1$— is the reacted product of a threonine side chain. In embodiments, -$L^3$-$X^1$— is the reacted product of a tyrosine side chain.

Further to any aspect disclosed herein contemplating a compound of Formulae (III), (IV), (V), or embodiments thereof, in embodiments $L^2$ and $L^3$ are independently a bond, —S(O)$_2$—, —NH—, —O—, —S—, —C(O)—, —NHC(O)—, —C(O)NH—, —NHC(O)NH—, —C(O)O—, —OC(O)—, —NHS(O)$_2$—, —S(O)$_2$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^2$ is a bond, —S(O)$_2$—, —NH—, —O—, —S—, —C(O)—, —NHC(O)—, —C(O)NH—, —NHC(O)NH—, —C(O)O—, —OC(O)—, —NHS(O)$_2$—, —S(O)$_2$NH—, $R^{8A}$-substituted or unsubstituted alkylene (e.g., $C_1$-$C_8$ alkylene, $C_1$-$C_6$ alkylene, or $C_1$-$C_4$ alkylene), $R^{8A}$-substituted or unsubstituted heteroalkylene (e.g., 2 to 10 membered heteroalkylene, 2 to 8 membered heteroalkylene, 2 to 6 membered heteroalkylene, or 2 to 4 membered heteroalkylene), $R^{8A}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{8A}$-substituted or unsubstituted heterocycloalkylene (e.g., 3 to 8 membered heterocycloalkylene, 3 to 6 membered heterocycloalkylene, or 5 to 6 membered heterocycloalkylene), $R^{8A}$-substituted or unsubstituted arylene (e.g., $C_6$-$C_{10}$ arylene, $C_{10}$ arylene, or phenylene), or $R^{8A}$-substituted or unsubstituted heteroarylene (e.g., 5 to 10 membered heteroarylene, 5 to 9 membered heteroarylene, or 5 to 6 membered heteroarylene).

In embodiments, $L^2$ is $R^{8A}$-substituted or unsubstituted alkylene (e.g., $C_1$-$C_8$ alkylene, $C_1$-$C_6$ alkylene, or $C_1$-$C_4$ alkylene). In embodiments, $L^2$ is $R^{8A}$-substituted alkylene (e.g., $C_1$-$C_8$ alkylene, $C_1$-$C_6$ alkylene, or $C_1$-$C_4$ alkylene). In embodiments, $L^2$ is unsubstituted alkylene (e.g., $C_1$-$C_8$ alkylene, $C_1$-$C_6$ alkylene, or $C_1$-$C_4$ alkylene).

In embodiments, $L^2$ is $R^{8A}$-substituted or unsubstituted heteroalkylene (e.g., 2 to 8 membered heteroalkylene, 2 to 6 membered heteroalkylene, or 2 to 4 membered heteroalkylene). In embodiments, $L^2$ is $R^{8A}$-substituted heteroalkylene (e.g., 2 to 8 membered heteroalkylene, 2 to 6 membered heteroalkylene, or 2 to 4 membered heteroalkylene). In embodiments $L^2$ is unsubstituted heteroalkylene (e.g., 2 to 8 membered heteroalkylene, 2 to 6 membered heteroalkylene, or 2 to 4 membered heteroalkylene).

In embodiments, $L^2$ is $R^{8A}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^2$ is $R^{8A}$-substituted cycloalkylene (e.g., $C_3$-$C_8$ cycloalkylene, $C_3$-$C_6$ cycloalkylene, or $C_5$-$C_6$ cycloalkylene). In embodiments, $L^2$ is unsubstituted cycloalkylene (e.g., $C_3$-$C_8$ cycloalkylene, $C_3$-$C_6$ cycloalkylene, or $C_5$-$C_6$ cycloalkylene).

In embodiments, $L^2$ is $R^{8A}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^2$ is $R^{8A}$-substituted heterocycloalkylene (e.g., 3 to 8 membered heterocycloalkylene, 3 to 6 membered heterocycloalkylene, or 5 to 6 membered heterocycloalkylene). In embodiments, $L^2$ is unsubstituted heterocycloalkylene (e.g., 3 to 8 membered heterocycloalkylene, 3 to 6 membered heterocycloalkylene, or 5 to 6 membered heterocycloalkylene).

In embodiments, $L^2$ is $R^{8A}$-substituted or unsubstituted arylene (e.g., $C_6$-$C_{10}$ arylene, $C_{10}$ arylene, or phenylene). In embodiments, $L^2$ is $R^{8A}$-substituted arylene (e.g., $C_6$-$C_{10}$ arylene, $C_{10}$ arylene, or phenylene). In embodiments, $L^2$ is unsubstituted arylene (e.g., $C_6$-$C_{10}$ arylene, $C_{10}$ arylene, or phenylene).

In embodiments, $L^2$ is $R^{8A}$-substituted or unsubstituted heteroarylene (e.g., 5 to 10 membered heteroarylene, 5 to 9 membered heteroarylene, or 5 to 6 membered heteroarylene). In embodiments, $L^2$ is $R^{8A}$-substituted heteroarylene (e.g., 5 to 10 membered heteroarylene, 5 to 9 membered heteroarylene, or 5 to 6 membered heteroarylene). In embodiments, $L^2$ is unsubstituted heteroarylene (e.g., 5 to 10 membered heteroarylene, 5 to 9 membered heteroarylene, or 5 to 6 membered heteroarylene).

$R^{8A}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $R^{9A}$-substituted or unsubstituted alkyl (e.g., $C_1$-$C_8$ alkyl, $C_1$-$C_6$ alkyl, or $C_1$-$C_4$ alkyl), $R^{9A}$-substituted or unsubstituted heteroalkyl (e.g., 2 to 8 membered heteroalkyl, 2 to 6 membered heteroalkyl, or 2 to 4 membered heteroalkyl), $R^{9A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{9A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{9A}$-substituted or unsubstituted aryl (e.g., $C_6$-$C_{10}$ aryl, $C_{10}$ aryl, or phenyl), or $R^{9A}$-substituted or unsubstituted heteroaryl (e.g., 5 to 10 membered heteroaryl, 5 to 9 membered heteroaryl, or 5 to 6 membered heteroaryl).

$R^{9A}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $R^{10A}$-substituted or unsubstituted alkyl (e.g., $C_1$-$C_8$ alkyl, $C_1$-$C_6$ alkyl, or $C_1$-$C_4$ alkyl), $R^{10A}$-substituted or unsubstituted heteroalkyl (e.g., 2 to 8 membered heteroalkyl, 2 to 6 membered heteroalkyl, or 2 to 4 membered heteroalkyl), $R^{10A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{14O}$-substituted or unsubstituted heterocycloalkyl (e.g., 3 to 8 membered heterocycloalkyl, 3 to 6 membered heterocycloalkyl, or 5 to 6 membered heterocycloalkyl), $R^{10A}$-substituted or unsubstituted aryl (e.g., $C_6$-$C_{10}$ aryl, $C_{10}$ aryl, or phenyl), or $R^{10A}$-substituted or unsubstituted heteroaryl (e.g., 5 to 10 membered heteroaryl, 5 to 9 membered heteroaryl, or 5 to 6 membered heteroaryl).

$R^{10A}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl) unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $L^3$ is a bond, $-S(O)_2-$, $-NH-$, $-O-$, $-S-$, $-C(O)-$, $-NHC(O)-$, $-C(O)NH-$, $-NHC(O)NH-$, $-C(O)O-$, $-OC(O)-$, $-NHS(O)_2-$, $-S(O)_2NH-$, $R^{8B}$-substituted or unsubstituted alkylene (e.g., $C_1$-$C_8$ alkylene, $C_1$-$C_6$ alkylene, or $C_1$-$C_4$ alkylene), $R^{8B}$-substituted or unsubstituted heteroalkylene (e.g., 2 to 10 membered heteroalkylene, 2 to 8 membered heteroalkylene, 2 to 6 membered heteroalkylene, or 2 to 4 membered heteroalkylene), $R^{8B}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{8B}$-substituted or unsubstituted heterocycloalkylene (e.g., 3 to 8 membered heterocycloalkylene, 3 to 6 membered heterocycloalkylene, or 5 to 6 membered heterocycloalkylene), $R^{8B}$-substituted or unsubstituted arylene (e.g., $C_6$-$C_{10}$ arylene, $C_{10}$ arylene, or phenylene), or $R^{8B}$-substituted or unsubstituted heteroarylene (e.g., 5 to 10 membered heteroarylene, 5 to 9 membered heteroarylene, or 5 to 6 membered heteroarylene).

In embodiments, $L^3$ is $R^{8B}$-substituted or unsubstituted alkylene (e.g., $C_1$-$C_8$ alkylene, $C_1$-$C_6$ alkylene, or $C_1$-$C_4$ alkylene). In embodiments, $L^3$ is $R^{8B}$-substituted alkylene (e.g., $C_1$-$C_8$ alkylene, $C_1$-$C_6$ alkylene, or $C_1$-$C_4$ alkylene). In embodiments, $L^3$ is unsubstituted alkylene (e.g., $C_1$-$C_8$ alkylene, $C_1$-$C_6$ alkylene, or $C_1$-$C_4$ alkylene).

In embodiments, $L^3$ is $R^{8B}$-substituted or unsubstituted heteroalkylene (e.g., 2 to 8 membered heteroalkylene, 2 to 6 membered heteroalkylene, or 2 to 4 membered heteroalkylene). In embodiments, $L^3$ is $R^{8B}$-substituted heteroalkylene (e.g., 2 to 8 membered heteroalkylene, 2 to 6 membered heteroalkylene, or 2 to 4 membered heteroalkylene). In embodiments $L^3$ is unsubstituted heteroalkylene (e.g., 2 to 8 membered heteroalkylene, 2 to 6 membered heteroalkylene, or 2 to 4 membered heteroalkylene).

In embodiments, $L^3$ is $R^{8B}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^3$ is $R^{8B}$-substituted cycloalkylene (e.g., $C_3$-$C_8$ cycloalkylene, $C_3$-$C_6$ cycloalkylene, or $C_5$-$C_6$ cycloalkylene). In embodiments, $L^3$ is unsubstituted cycloalkylene (e.g., $C_3$-$C_8$ cycloalkylene, $C_3$-$C_6$ cycloalkylene, or $C_5$-$C_6$ cycloalkylene).

In embodiments, $L^3$ is $R^{8B}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^3$ is $R^{8B}$-substituted heterocycloalkylene (e.g., 3 to 8 membered heterocycloalkylene, 3 to 6 membered heterocycloalkylene, or 5 to 6 membered heterocycloalkylene). In embodiments, $L^3$ is unsubstituted heterocycloalkylene (e.g., 3 to 8 membered heterocycloalkylene, 3 to 6 membered heterocycloalkylene, or 5 to 6 membered heterocycloalkylene).

In embodiments, $L^3$ is $R^{8B}$-substituted or unsubstituted arylene (e.g., $C_6$-$C_{10}$ arylene, $C_{10}$ arylene, or phenylene). In embodiments, $L^3$ is $R^{8B}$-substituted arylene (e.g., $C_6$-$C_{10}$ arylene, $C_{10}$ arylene, or phenylene). In embodiments, $L^3$ is unsubstituted arylene (e.g., $C_6$-$C_{10}$ arylene, $C_{10}$ arylene, or phenylene).

In embodiments, $L^3$ is $R^{8B}$-substituted or unsubstituted heteroarylene (e.g., 5 to 10 membered heteroarylene, 5 to 9 membered heteroarylene, or 5 to 6 membered heteroarylene). In embodiments, $L^3$ is $R^{8B}$-substituted heteroarylene (e.g., 5 to 10 membered heteroarylene, 5 to 9 membered heteroarylene, or 5 to 6 membered heteroarylene). In embodiments, $L^3$ is unsubstituted heteroarylene (e.g., 5 to 10 membered heteroarylene, 5 to 9 membered heteroarylene, or 5 to 6 membered heteroarylene).

$R^{8B}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $R^{9B}$-substituted or unsubstituted alkyl (e.g., $C_1$-$C_8$ alkyl, $C_1$-$C_6$ alkyl, or $C_1$-$C_4$ alkyl), $R^{9B}$-substituted or unsubstituted heteroalkyl (e.g., 2 to 8 membered heteroalkyl, 2 to 6 membered heteroalkyl, or 2 to 4 membered heteroalkyl), $R^{9B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{9B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{9B}$-substituted or unsubstituted aryl (e.g., $C_6$-$C_{10}$ aryl, $C_{10}$ aryl, or phenyl), or $R^{9B}$-substituted or unsubstituted heteroaryl (e.g., 5 to 10 membered heteroaryl, 5 to 9 membered heteroaryl, or 5 to 6 membered heteroaryl).

$R^{9B}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $R^{10B}$-substituted or unsubstituted alkyl (e.g., $C_1$-$C_8$ alkyl, $C_1$-$C_6$ alkyl, or $C_1$-$C_4$ alkyl), $R^{10B}$-substituted or unsubstituted heteroalkyl (e.g., 2 to 8 membered heteroalkyl, 2 to 6 membered heteroalkyl, or 2 to 4 membered heteroalkyl), $R^{10B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{10B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{10B}$-substituted or unsubstituted aryl (e.g., $C_6$-$C_{10}$ aryl, $C_{10}$ aryl, or phenyl), or $R^{10B}$-substituted or unsubstituted heteroaryl (e.g., 5 to 10 membered heteroaryl, 5 to 9 membered heteroaryl, or 5 to 6 membered heteroaryl).

$R^{10B}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

Further to any aspect disclosed herein contemplating a compound of Formulae (III), (IV), (V), or embodiments thereof, in embodiments -$L^3$-$X^1$— is the reacted product of a lysine side chain, histidine side chain, cysteine side chain, serine side chain, threonine side chain or tyrosine side chain. In embodiments, -$L^3$-$X^1$— is the reacted product of a lysine side chain. In embodiments, -$L^3$-$X^1$— is the reacted product of a cysteine side chain. In embodiments, -$L^3$-$X^1$— is the reacted product of a serine, threonine or tyrosine side chain.

In embodiments, the first peptidyl moiety $R^4$ is 1 to 200 amino acid residues in length. In embodiments, the second peptidyl moiety $R^5$ is 1 to 200 amino acid residues in length. In embodiments, the third peptidyl moiety $R^6$ is 1 to 200 amino acid residues in length. In embodiments, the fourth peptidyl moiety $R^7$ is 1 to 200 amino acid residues in length.

In embodiments, the first peptidyl moiety $R^4$ is 1 to 2000 amino acid residues in length. In embodiments, the first peptidyl moiety $R^4$ is 1 to 1500 amino acid residues in length. In embodiments, the first peptidyl moiety $R^4$ is 1 to 1000 amino acid residues in length. In embodiments, the first peptidyl moiety $R^4$ is 1 to 900 amino acid residues in length. In embodiments, the first peptidyl moiety $R^4$ is 1 to 800 amino acid residues in length. In embodiments, the first peptidyl moiety $R^4$ is 1 to 700 amino acid residues in length. In embodiments, the first peptidyl moiety $R^4$ is 1 to 600 amino acid residues in length. In embodiments, the first peptidyl moiety $R^4$ is 1 to 500 amino acid residues in length. In embodiments, the first peptidyl moiety $R^4$ is 1 to 400 amino acid residues in length. In embodiments, the first peptidyl moiety $R^4$ is 1 to 300 amino acid residues in length. In embodiments, the first peptidyl moiety $R^4$ is 1 to 200 amino acid residues in length. In embodiments, the first peptidyl moiety $R^4$ is 1 to 100 amino acid residues in length. In embodiments, the first peptidyl moiety $R^4$ is 1 to 90 amino acid residues in length. In embodiments, the first peptidyl moiety $R^4$ is 1 to 80 amino acid residues in length. In embodiments, the first peptidyl moiety $R^4$ is 1 to 70 amino acid residues in length. In embodiments, the first peptidyl moiety $R^4$ is 1 to 60 amino acid residues in length. In embodiments, the first peptidyl moiety $R^4$ is 1 to 50 amino acid residues in length. In embodiments, the first peptidyl moiety $R^4$ is 1 to 40 amino acid residues in length. In embodiments, the first peptidyl moiety $R^4$ is 1 to 30 amino acid residues in length. In embodiments, the first peptidyl moiety $R^4$ is 1 to 20 amino acid residues in length. In embodiments, the first peptidyl moiety $R^4$ is 1 to 10 amino acid residues in length. In embodiments, the first peptidyl moiety $R^4$ is 1 to 9 amino acid residues in length. In embodiments, the first peptidyl moiety $R^4$ is 1 to 8 amino acid residues in length. In embodiments, the first peptidyl moiety $R^4$ is 1 to 7 amino acid residues in length. In embodiments, the first peptidyl moiety $R^4$ is 1 to 6 amino acid residues in length. In embodiments, the first peptidyl moiety $R^4$ is 1 to 5 amino acid residues in length. In embodiments, the first peptidyl moiety $R^4$ is 1 to 4 amino acid residues in length. In embodiments, the first peptidyl moiety $R^4$ is 1 to 3 amino acid residues in length. In embodiments, the first peptidyl moiety $R^4$ is 1 to 2 amino acid residues in length. In embodiments, $R^4$ is 1, 2, 3, 4, 5, 6, 7, 8, 9, 10, 11, 12, 13, 14, 15, 16, 17, 18, 19, 20 amino acid residues in length. In embodiments, $R^4$ is about 20, 25, 30, 35, 40, 45 or 50 amino acid residues in length. In embodiments, $R^4$ is about 50, 60, 70, 80, 90 or 100 amino acid residues in length. In embodiments, $R^4$ is about 100, 200, 300, 400, 500, 600, 700, 800, 900, 1000, 1500 or 2000 amino acid residues in length. In embodiments, $R^4$ is 1 amino acid residue in length. In embodiments, $R^4$ is 2 amino acid residue in length. In embodiments, $R^4$ is 3 amino acid residue in length. In embodiments, $R^4$ is 4 amino acid residue in length. In embodiments, $R^4$ is 5 amino acid residue in length. In embodiments, $R^4$ is 6 amino acid residue in length. In embodiments, $R^4$ is 7 amino acid residue in length. In embodiments, $R^4$ is 8 amino acid residue in length. In embodiments, $R^4$ is 9 amino acid residue in length. In embodiments, $R^4$ is 10 amino acid residue in length. In embodiments, $R^4$ is 11 amino acid residue in length. In embodiments, $R^4$ is 12 amino acid residue in length. In embodiments, $R^4$ is 13 amino acid residue in length. In embodiments, $R^4$ is 14 amino acid residue in length. In embodiments, $R^4$ is 15 amino acid residue in length. In embodiments, $R^4$ is 16 amino acid residue in length. In embodiments, $R^4$ is 17 amino acid residue in length. In embodiments, $R^4$ is 18 amino acid residue in length. In embodiments, $R^4$ is 19 amino acid residue in length. In embodiments, $R^4$ is 20 amino acid residue in length. In embodiments, $R^4$ is about 20 amino acid residues in length. In embodiments, $R^4$ is about 25 amino acid residues in length. In embodiments, $R^4$ is about 30 amino acid residues in length. In embodiments, $R^4$ is about 35 amino acid residues in length. In embodiments, $R^4$ is about 40 amino acid residues in length. In embodiments, $R^4$ is about 45 amino acid residues in length. In embodiments, $R^4$ is about 50 amino acid residues in length. In embodiments, $R^4$ is about 60 amino acid residues in length. In embodiments, $R^4$ is about 70 amino acid residues in length. In embodiments, $R^4$ is about 80 amino acid residues in length. In embodiments, $R^4$ is about 90 amino acid residues in length. In embodiments, $R^4$ is about 100 amino acid residues in length. In embodiments, $R^4$ is about 200 amino acid residues in length. In embodiments, $R^4$ is about 300 amino acid residues in length. In embodiments, $R^4$ is about 400 amino acid residues in length. In embodiments, $R^4$ is about 500 amino acid residues in length.

In embodiments, $R^4$ is about 600 amino acid residues in length. In embodiments, $R^4$ is about 700 amino acid residues in length. In embodiments, $R^4$ is about 800 amino acid residues in length. In embodiments, $R^4$ is about 900 amino acid residues in length. In embodiments, $R^4$ is about 1000 amino acid residues in length. In embodiments, $R^4$ is about 1500 amino acid residues in length. In embodiments, $R^4$ is about 2000 amino acid residues in length.

In embodiments, the second peptidyl moiety $R^5$ is 1 to 2000 amino acid residues in length. In embodiments, the second peptidyl moiety $R^5$ is 1 to 1500 amino acid residues in length. In embodiments, the second peptidyl moiety $R^5$ is 1 to 1000 amino acid residues in length. In embodiments, the second peptidyl moiety $R^5$ is 1 to 900 amino acid residues in length. In embodiments, the second peptidyl moiety $R^5$ is 1 to 800 amino acid residues in length. In embodiments, the second peptidyl moiety $R^5$ is 1 to 700 amino acid residues in length. In embodiments, the second peptidyl moiety $R^5$ is 1 to 600 amino acid residues in length. In embodiments, the second peptidyl moiety $R^5$ is 1 to 500 amino acid residues in length. In embodiments, the second peptidyl moiety $R^5$ is 1 to 400 amino acid residues in length. In embodiments, the second peptidyl moiety $R^5$ is 1 to 300 amino acid residues in length. In embodiments, the second peptidyl moiety $R^5$ is 1 to 200 amino acid residues in length. In embodiments, the second peptidyl moiety $R^5$ is 1 to 100 amino acid residues in length. In embodiments, the second peptidyl moiety $R^5$ is 1 to 90 amino acid residues in length. In embodiments, the second peptidyl moiety $R^5$ is 1 to 80 amino acid residues in length. In embodiments, the second peptidyl moiety $R^5$ is 1 to 70 amino acid residues in length. In embodiments, the second peptidyl moiety $R^5$ is 1 to 60 amino acid residues in length. In embodiments, the second peptidyl moiety $R^5$ is 1 to 50 amino acid residues in length. In embodiments, the second peptidyl moiety $R^5$ is 1 to 40 amino acid residues in length. In embodiments, the second peptidyl moiety $R^5$ is 1 to 30 amino acid residues in length. In embodiments, the second peptidyl moiety $R^5$ is 1 to 20 amino acid residues in length. In embodiments, the second peptidyl moiety $R^5$ is 1 to 10 amino acid residues in length. In embodiments, the second peptidyl moiety $R^5$ is 1 to 9 amino acid residues in length. In embodiments, the second peptidyl moiety $R^5$ is 1 to 8 amino acid residues in length. In embodiments, the second peptidyl moiety $R^5$ is 1 to 7 amino acid residues in length. In embodiments, the second peptidyl moiety $R^5$ is 1 to 6 amino acid residues in length. In embodiments, the second peptidyl moiety $R^5$ is 1 to 5 amino acid residues in length. In embodiments, the second peptidyl moiety $R^5$ is 1 to 4 amino acid residues in length. In embodiments, the second peptidyl moiety $R^5$ is 1 to 3 amino acid residues in length. In embodiments, the second peptidyl moiety $R^5$ is 1 to 2 amino acid residues in length. In embodiments, $R^5$ is 1, 2, 3, 4, 5, 6, 7, 8, 9, 10, 11, 12, 13, 14, 15, 16, 17, 18, 19, 20 amino acid residues in length. In embodiments, $R^5$ is about 20, 25, 30, 35, 40, 45 or 50 amino acid residues in length. In embodiments, $R^5$ is about 50, 60, 70, 80, 90 or 100 amino acid residues in length. In embodiments, $R^5$ is about 100, 200, 300, 400, 500, 600, 700, 800, 900, 1000, 1500 or 2000 amino acid residues in length. In embodiments, $R^5$ is 1 amino acid residue in length. In embodiments, $R^5$ is 2 amino acid residue in length. In embodiments, $R^5$ is 3 amino acid residue in length. In embodiments, $R^5$ is 4 amino acid residue in length. In embodiments, $R^5$ is 5 amino acid residue in length. In embodiments, $R^5$ is 6 amino acid residue in length. In embodiments, $R^5$ is 7 amino acid residue in length. In embodiments, $R^5$ is 8 amino acid residue in length. In embodiments, $R^5$ is 9 amino acid residue in length. In embodiments, $R^5$ is 10 amino acid residue in length. In embodiments, $R^5$ is 11 amino acid residue in length. In embodiments, $R^5$ is 12 amino acid residue in length. In embodiments, $R^5$ is 13 amino acid residue in length. In embodiments, $R^5$ is 14 amino acid residue in length. In embodiments, $R^5$ is 15 amino acid residue in length. In embodiments, $R^5$ is 16 amino acid residue in length. In embodiments, $R^5$ is 17 amino acid residue in length. In embodiments, $R^5$ is 18 amino acid residue in length. In embodiments, $R^5$ is 19 amino acid residue in length. In embodiments, $R^5$ is 20 amino acid residue in length. In embodiments, $R^5$ is about 20 amino acid residues in length. In embodiments, $R^5$ is about 25 amino acid residues in length. In embodiments, $R^5$ is about 30 amino acid residues in length. In embodiments, $R^5$ is about 35 amino acid residues in length. In embodiments, $R^5$ is about 40 amino acid residues in length. In embodiments, $R^5$ is about 45 amino acid residues in length. In embodiments, $R^5$ is about 50 amino acid residues in length. In embodiments, $R^5$ is about 60 amino acid residues in length. In embodiments, $R^5$ is about 70 amino acid residues in length. In embodiments, $R^5$ is about 80 amino acid residues in length. In embodiments, $R^5$ is about 90 amino acid residues in length. In embodiments, $R^5$ is about 100 amino acid residues in length. In embodiments, $R^5$ is about 200 amino acid residues in length. In embodiments, $R^5$ is about 300 amino acid residues in length. In embodiments, $R^5$ is about 400 amino acid residues in length. In embodiments, $R^5$ is about 500 amino acid residues in length. In embodiments, $R^5$ is about 600 amino acid residues in length. In embodiments, $R^5$ is about 700 amino acid residues in length. In embodiments, $R^5$ is about 800 amino acid residues in length. In embodiments, $R^5$ is about 900 amino acid residues in length. In embodiments, $R^5$ is about 1000 amino acid residues in length. In embodiments, $R^5$ is about 1500 amino acid residues in length. In embodiments, $R^5$ is about 2000 amino acid residues in length.

In embodiments, the third peptidyl moiety $R^6$ is 1 to 2000 amino acid residues in length. In embodiments, the third peptidyl moiety $R^6$ is 1 to 1500 amino acid residues in length. In embodiments, the third peptidyl moiety $R^6$ is 1 to 1000 amino acid residues in length. In embodiments, the third peptidyl moiety $R^6$ is 1 to 900 amino acid residues in length. In embodiments, the third peptidyl moiety $R^6$ is 1 to 800 amino acid residues in length. In embodiments, the third peptidyl moiety $R^6$ is 1 to 700 amino acid residues in length. In embodiments, the third peptidyl moiety $R^6$ is 1 to 600 amino acid residues in length. In embodiments, the third peptidyl moiety $R^6$ is 1 to 500 amino acid residues in length. In embodiments, the third peptidyl moiety $R^6$ is 1 to 400 amino acid residues in length. In embodiments, the third peptidyl moiety $R^6$ is 1 to 300 amino acid residues in length. In embodiments, the third peptidyl moiety $R^6$ is 1 to 200 amino acid residues in length. In embodiments, the third peptidyl moiety $R^6$ is 1 to 100 amino acid residues in length. In embodiments, the third peptidyl moiety $R^6$ is 1 to 90 amino acid residues in length. In embodiments, the third peptidyl moiety $R^6$ is 1 to 80 amino acid residues in length. In embodiments, the third peptidyl moiety $R^6$ is 1 to 70 amino acid residues in length. In embodiments, the third peptidyl moiety $R^6$ is 1 to 60 amino acid residues in length. In embodiments, the third peptidyl moiety $R^6$ is 1 to 50 amino acid residues in length. In embodiments, the third peptidyl moiety $R^6$ is 1 to 40 amino acid residues in length. In embodiments, the third peptidyl moiety $R^6$ is 1 to 30 amino acid residues in length. In embodiments, the third peptidyl moiety $R^6$ is 1 to 20 amino acid residues in length. In embodiments, the third peptidyl moiety $R^6$ is 1 to 10 amino acid residues in length. In embodiments, the third peptidyl moiety $R^6$ is 1 to 9 amino acid residues in length. In embodiments, the third peptidyl moiety $R^6$ is 1 to 8 amino acid residues in length. In embodiments, the third peptidyl moiety $R^6$ is 1 to 7 amino acid residues in length. In embodiments, the third peptidyl moiety $R^6$ is 1 to 6 amino acid residues in length. In embodiments, the third peptidyl moiety $R^6$ is 1 to 5 amino acid residues in length. In embodiments, the third peptidyl moiety $R^6$ is 1 to 4 amino acid residues in length. In embodiments, the third peptidyl moiety $R^6$ is 1 to 3 amino acid residues in length. In embodiments, the third peptidyl moiety $R^6$ is 1 to 2 amino acid residues in length. In embodiments, $R^6$ is 1, 2, 3, 4, 5, 6, 7, 8, 9, 10, 11, 12, 13, 14, 15, 16, 17, 18, 19, 20 amino acid residues in length. In embodiments, $R^6$ is about 20, 25, 30, 35, 40, 45 or 50 amino acid residues in length. In embodiments, $R^6$ is about 50, 60, 70, 80, 90 or 100 amino acid residues in length. In embodiments, $R^6$ is about 100, 200, 300, 400, 500, 600, 700, 800, 900, 1000, 1500 or 2000 amino acid residues in length. In embodiments, $R^6$ is 1 amino acid residue in length. In embodiments, $R^6$ is 2 amino acid residue in length. In embodiments, $R^6$ is 3 amino acid residue in length. In embodiments, $R^6$ is 4 amino acid residue in length. In embodiments, $R^6$ is 5 amino acid residue in length. In embodiments, $R^6$ is 6 amino acid residue in length. In embodiments, $R^6$ is 7 amino acid residue in length. In embodiments, $R^6$ is 8 amino acid residue in length. In embodiments, $R^6$ is 9 amino acid residue in length. In embodiments, $R^6$ is 10 amino acid residue in length. In embodiments, $R^6$ is 11 amino acid residue in length. In embodiments, $R^6$ is 12 amino acid residue in length. In embodiments, $R^6$ is 13 amino acid residue in length. In embodiments, $R^6$ is 14 amino acid residue in length. In embodiments, $R^6$ is 15 amino acid residue in length. In embodiments, $R^6$ is 16 amino acid residue in length. In embodiments, $R^6$ is 17 amino acid residue in length. In embodiments, $R^6$ is 18 amino acid residue in length. In embodiments, $R^6$ is 19 amino acid residue in length. In embodiments, $R^6$ is 20 amino acid residue in length. In embodiments, $R^6$ is about 20 amino acid residues in length. In embodiments, $R^6$ is about 25 amino acid residues in length. In embodiments, $R^6$ is about 30 amino acid residues in length. In embodiments, $R^6$ is about 35 amino acid residues in length. In embodiments, $R^6$ is about 40 amino acid residues in length. In embodiments, $R^6$ is about 45 amino acid residues in length. In embodiments, $R^6$ is about 50 amino acid residues in length. In embodiments, $R^6$ is about 60 amino acid residues in length. In embodiments, $R^6$ is about 70 amino acid residues in length. In embodiments, $R^6$ is about 80 amino acid residues in length. In embodiments, $R^6$ is about 90 amino acid residues in length. In embodiments, $R^6$ is about 100 amino acid residues in length. In embodiments, $R^6$ is about 200 amino acid residues in length. In embodiments, $R^6$ is about 300 amino acid residues in length. In embodiments, $R^6$ is about 400 amino acid residues in length. In embodiments, $R^6$ is about 500 amino acid residues in length. In embodiments, $R^6$ is about 600 amino acid residues in length. In embodiments, $R^6$ is about 700 amino acid residues in length. In embodiments, $R^6$ is about 800 amino acid residues in length. In embodiments, $R^6$ is about 900 amino acid residues in length. In embodiments, $R^6$ is about 1000 amino acid residues in length. In embodiments, $R^6$ is about 1500 amino acid residues in length. In embodiments, $R^6$ is about 2000 amino acid residues in length.

In embodiments, the fourth peptidyl moiety $R^7$ is 1 to 2000 amino acid residues in length. In embodiments, the fourth peptidyl moiety $R^7$ is 1 to 1500 amino acid residues in length. In embodiments, the fourth peptidyl moiety $R^7$ is 1 to 1000 amino acid residues in length. In embodiments, the fourth peptidyl moiety $R^7$ is 1 to 900 amino acid residues in length. In embodiments, the fourth peptidyl moiety $R^7$ is 1 to 800 amino acid residues in length. In embodiments, the fourth peptidyl moiety $R^7$ is 1 to 700 amino acid residues in length. In embodiments, the fourth peptidyl moiety $R^7$ is 1 to 600 amino acid residues in length. In embodiments, the fourth peptidyl moiety $R^7$ is 1 to 500 amino acid residues in length. In embodiments, the fourth peptidyl moiety $R^7$ is 1 to 400 amino acid residues in length. In embodiments, the fourth peptidyl moiety $R^7$ is 1 to 300 amino acid residues in length. In embodiments, the fourth peptidyl moiety $R^7$ is 1 to 200 amino acid residues in length. In embodiments, the fourth peptidyl moiety $R^7$ is 1 to 100 amino acid residues in length. In embodiments, the fourth peptidyl moiety $R^7$ is 1 to 90 amino acid residues in length. In embodiments, the fourth peptidyl moiety $R^7$ is 1 to 80 amino acid residues in length. In embodiments, the fourth peptidyl moiety $R^7$ is 1 to 70 amino acid residues in length. In embodiments, the fourth peptidyl moiety $R^7$ is 1 to 60 amino acid residues in length. In embodiments, the fourth peptidyl moiety $R^7$ is 1 to 50 amino acid residues in length. In embodiments, the fourth peptidyl moiety $R^7$ is 1 to 40 amino acid residues in length. In embodiments, the fourth peptidyl moiety $R^7$ is 1 to 30 amino acid residues in length. In embodiments, the fourth peptidyl moiety $R^7$ is 1 to 20 amino acid residues in length. In embodiments, the fourth peptidyl moiety $R^7$ is 1 to 10 amino acid residues in length. In embodiments, the fourth peptidyl moiety $R^7$ is 1 to 9 amino acid residues in length. In embodiments, the fourth peptidyl moiety $R^7$ is 1 to 8 amino acid residues in length. In embodiments, the fourth peptidyl moiety $R^7$ is 1 to 7 amino acid residues in length. In embodiments, the fourth peptidyl moiety $R^7$ is 1 to 6 amino acid residues in length. In embodiments, the fourth peptidyl moiety $R^7$ is 1 to 5 amino acid residues in length. In embodiments, the fourth peptidyl moiety $R^7$ is 1 to 4 amino acid residues in length. In embodiments, the fourth peptidyl moiety $R^7$ is 1 to 3 amino acid residues in length. In embodiments, the fourth peptidyl moiety $R^7$ is 1 to 2 amino acid residues in length. In embodiments, $R^7$ is 1, 2, 3, 4, 5, 6, 7, 8, 9, 10, 11, 12, 13, 14, 15, 16, 17, 18, 19, 20 amino acid residues in length. In embodiments, $R^7$ is about 20, 25, 30, 35, 40, 45 or 50 amino acid residues in length. In embodiments, $R^7$ is about 50, 60, 70, 80, 90 or 100 amino acid residues in length. In embodiments, $R^7$ is about 100, 200, 300, 400, 500, 600, 700, 800, 900, 1000, 1500 or 2000 amino acid residues in length. In embodiments, $R^7$ is 1 amino acid residue in length. In embodiments, $R^7$ is 2 amino acid residue in length. In embodiments, $R^7$ is 3 amino acid residue in length. In embodiments, $R^7$ is 4 amino acid residue in length. In embodiments, $R^7$ is 5 amino acid residue in length. In embodiments, $R^7$ is 6 amino acid residue in length. In embodiments, $R^7$ is 7 amino acid residue in length. In embodiments, $R^7$ is 8 amino acid residue in length. In embodiments, $R^7$ is 9 amino acid residue in length. In embodiments, $R^7$ is 10 amino acid residue in length. In embodiments, $R^7$ is 11 amino acid residue in length. In embodiments, $R^7$ is 12 amino acid residue in length. In embodiments, $R^7$ is 13 amino acid residue in length. In embodiments, $R^7$ is 14 amino acid residue in length. In embodiments, $R^7$ is 15 amino acid residue in length. In embodiments, $R^7$ is 16 amino acid residue in length. In embodiments, $R^7$ is 17 amino acid residue in length. In embodiments, $R^7$ is 18 amino acid residue in length. In embodiments, $R^7$ is 19 amino acid residue in length. In embodiments, $R^7$ is 20 amino acid residue in length. In embodiments, $R^7$ is about 20 amino acid residues in length. In embodiments, $R^7$ is about 25 amino acid residues in length. In embodiments, $R^7$ is about 30 amino acid residues in length. In embodiments, $R^7$ is about 35 amino acid residues in length. In embodiments, $R^7$ is about 40 amino acid residues in length. In embodiments, $R^7$ is about 45 amino acid residues in length. In embodiments, $R^7$ is about 50 amino acid residues in length. In embodiments, $R^7$ is about 60 amino acid residues in length. In embodiments, $R^7$ is about 70 amino acid residues in length. In embodiments, $R^7$ is about 80 amino acid residues in length. In embodiments, $R^7$ is about 90 amino acid residues in length. In embodiments, $R^7$ is about 100 amino acid residues in length. In embodiments, $R^7$ is about 200 amino acid residues in length. In embodiments, $R^7$ is about 300 amino acid residues in length. In embodiments, $R^7$ is about 400 amino acid residues in length. In embodiments, $R^7$ is about 500 amino acid residues in length. In embodiments, $R^7$ is about 600 amino acid residues in length. In embodiments, $R^7$ is about 700 amino acid residues in length. In embodiments, $R^7$ is about 800 amino acid residues in length. In embodiments, $R^7$ is about 900 amino acid residues in length. In embodiments, $R^7$ is about 1000 amino acid residues in length. In embodiments, $R^7$ is about 1500 amino acid residues in length. In embodiments, $R^7$ is about 2000 amino acid residues in length.

The term "$T(R^4+R^5)$" means the total number of amino acids included in $R^4$ and $R^5$, and the term "$T(R^6+R^7)$" means the total number of amino acids included in $R^6$ and $R^7$. In embodiments, $T(R^4+R^5)$ is 1 to 2000 amino acid residues. In embodiments, $T(R^4+R^5)$ is 1 to 1500 amino acid residues. In embodiments, $T(R^4+R^5)$ is 1 to 1000 amino acid residues. In embodiments, $T(R^4+R^5)$ is 1 to 900 amino acid residues. In embodiments, $T(R^4+R^5)$ is 1 to 800 amino acid residues. In embodiments, $T(R^4+R^5)$ is 1 to 700 amino acid residues. In embodiments, $T(R^4+R^5)$ is 1 to 600 amino acid residues. In embodiments, $T(R^4+R^5)$ is 1 to 500 amino acid residues. In embodiments, $T(R^4+R^5)$ is 1 to 400 amino acid residues. In embodiments, $T(R^4+R^5)$ is 1 to 300 amino acid residues. In embodiments, $T(R^4+R^5)$ is 1 to 200 amino acid residues. In embodiments, $T(R^4+R^5)$ is 1 to 100 amino acid residues. In embodiments, $T(R^4+R^5)$ is 1 to 90 amino acid residues. In embodiments, $T(R^4+R^5)$ is 1 to 80 amino acid residues. In embodiments, $T(R^4+R^5)$ is 1 to 70 amino acid residues. In embodiments, $T(R^4+R^5)$ is 1 to 60 amino acid residues. In embodiments, $T(R^4+R^5)$ is 1 to 50 amino acid residues. In embodiments, $T(R^4+R^5)$ is 1 to 45 amino acid residues. In embodiments, $T(R^4+R^5)$ is 1 to 40 amino acid residues. In embodiments, $T(R^4+R^5)$ is 1 to 35 amino acid residues. In embodiments, $T(R^4+R^5)$ is 1 to 30 amino acid residues. In embodiments, $T(R^4+R^5)$ is 1 to 25 amino acid residues. In embodiments, $T(R^4+R^5)$ is 1 to 20 amino acid residues. In embodiments, $T(R^4+R^5)$ is 1 to 19 amino acid residues. In embodiments, $T(R^4+R^5)$ is 1 to 18 amino acid residues. In embodiments, $T(R^4+R^5)$ is 1 to 17 amino acid residues. In embodiments, $T(R^4+R^5)$ is 1 to 16 amino acid residues. In embodiments, $T(R^4+R^5)$ is 1 to 15 amino acid residues. In embodiments, $T(R^4+R^5)$ is 1 to 14 amino acid residues. In embodiments, $T(R^4+R^5)$ is 1 to 13 amino acid residues. In embodiments, $T(R^4+R^5)$ is 1 to 12 amino acid residues. In embodiments, $T(R^4+R^5)$ is 1 to 11 amino acid residues. In embodiments, $T(R^4+R^5)$ is 1 to 10 amino acid residues. In embodiments, $T(R^4+R^5)$ is 1 to 9 amino acid residues. In embodiments, $T(R^4+R^5)$ is 1 to 8 amino acid residues. In embodiments, $T(R^4+R^5)$ is 1 to 7 amino acid residues. In embodiments, $T(R^4+R^5)$ is 1 to 6 amino acid residues. In embodiments, $T(R^4+R^5)$ is 1 to 5 amino acid residues. In embodiments, $T(R^4+R^5)$ is 1 to 4 amino acid residues. In embodiments, $T(R^4+R^5)$ is 1 to 3 amino acid residues. In embodiments, $T(R^4+R^5)$ is 1 to 2 amino acid residues.

In embodiments, $T(R^6+R^7)$ is 1 to 2000 amino acid residues. In embodiments, $T(R^6+R^7)$ is 1 to 1500 amino acid residues. In embodiments, $T(R^6+R^7)$ is 1 to 1000 amino acid residues. In embodiments, $T(R^6+R^7)$ is 1 to 900 amino acid residues. In embodiments, $T(R^6+R^7)$ is 1 to 800 amino acid residues. In embodiments, $T(R^6+R^7)$ is 1 to 700 amino acid residues. In embodiments, $T(R^6+R^7)$ is 1 to 600 amino acid residues. In embodiments, $T(R^6+R^7)$ is 1 to 500 amino acid residues. In embodiments, $T(R^6+R^7)$ is 1 to 400 amino acid residues. In embodiments, $T(R^6+R^7)$ is 1 to 300 amino acid residues. In embodiments, $T(R^6+R^7)$ is 1 to 200 amino acid residues. In embodiments, $T(R^6+R^7)$ is 1 to 100 amino acid residues. In embodiments, $T(R^6+R^7)$ is 1 to 90 amino acid residues. In embodiments, $T(R^6+R^7)$ is 1 to 80 amino acid residues. In embodiments, $T(R^6+R^7)$ is 1 to 70 amino acid residues. In embodiments, $T(R^6+R^7)$ is 1 to 60 amino acid residues. In embodiments, $T(R^6+R^7)$ is 1 to 50 amino acid residues. In embodiments, $T(R^6+R^7)$ is 1 to 45 amino acid residues. In embodiments, $T(R^6+R^7)$ is 1 to 40 amino acid residues. In embodiments, $T(R^6+R^7)$ is 1 to 35 amino acid residues. In embodiments, $T(R^6+R^7)$ is 1 to 30 amino acid residues. In embodiments, $T(R^6+R^7)$ is 1 to 25 amino acid residues. In embodiments, $T(R^6+R^7)$ is 1 to 20 amino acid residues. In embodiments, $T(R^6+R^7)$ is 1 to 19 amino acid residues. In embodiments, $T(R^6+R^7)$ is 1 to 18 amino acid residues. In embodiments, $T(R^6+R^7)$ is 1 to 17 amino acid residues. In embodiments, $T(R^6+R^7)$ is 1 to 16 amino acid residues. In embodiments, $T(R^6+R)$ is 1 to 15 amino acid residues. In embodiments, $T(R^6+R^7)$ is 1 to 14 amino acid residues. In embodiments, $T(R^6+R^7)$ is 1 to 13 amino acid residues. In embodiments, $T(R^6+R^7)$ is 1 to 12 amino acid residues. In embodiments, $T(R^6+R^7)$ is 1 to 11 amino acid residues. In embodiments, $T(R^6+R^7)$ is 1 to 10 amino acid residues. In embodiments, $T(R^6+R^7)$ is 1 to 9 amino acid residues. In embodiments, $T(R^6+R^7)$ is 1 to 8 amino acid residues. In embodiments, $T(R^6+R)$ is 1 to 7 amino acid residues. In embodiments, $T(R^6+R^7)$ is 1 to 6 amino acid residues. In embodiments, $T(R^6+R^7)$ is 1 to 5 amino acid residues. In embodiments, $T(R^6+R^7)$ is 1 to 4 amino acid residues. In embodiments, $T(R^6+R^7)$ is 1 to 3 amino acid residues. In embodiments, $T(R^6+R^7)$ is 1 to 2 amino acid residues.

In embodiments, $R^4$ has a molecule weight in the range of 50 to 240,000 Dalton. In embodiments, $R^4$ has a molecule weight in the range of 50 to 180,000 Dalton. In embodiments, $R^4$ has a molecule weight in the range of 50 to 120,000 Dalton. In embodiments, $R^4$ has a molecule weight in the range of 50 to 108,000 Dalton. In embodiments, $R^4$ has a molecule weight in the range of 50 to 96,000 Dalton. In embodiments, $R^4$ has a molecule weight in the range of 50 to 84,000 Dalton. In embodiments, $R^4$ has a molecule weight in the range of 50 to 72,000 Dalton. In embodiments, $R^4$ has a molecule weight in the range of 50 to 60,000 Dalton. In embodiments, $R^4$ has a molecule weight in the range of 50 to 48,000 Dalton. In embodiments, $R^4$ has a molecule weight in the range of 50 to 36,000 Dalton. In embodiments, $R^4$ has a molecule weight in the range of 50 to 24,000 Dalton. In embodiments, $R^4$ has a molecule weight in the range of 50 to 12,000 Dalton. In embodiments, $R^4$ has a molecule weight in the range of 50 to 10,800 Dalton. In embodiments, $R^4$ has a molecule weight in the range of 50 to 9,600 Dalton. In embodiments, $R^4$ has a molecule weight in the range of 50 to 8,400 Dalton. In embodiments, $R^4$ has a molecule weight in the range of 50 to 7,200 Dalton. In embodiments, $R^4$ has a molecule weight in the range of 50 to 6,000 Dalton. In embodiments, $R^4$ has a molecule weight in the range of 50 to 5,400 Dalton. In embodiments, $R^4$ has a molecule weight in the range of 50 to 4,800 Dalton. In embodiments, $R^4$ has a molecule weight in the range of 50 to 4,200 Dalton. In embodiments, $R^4$ has a molecule weight in the range of 50 to 3,600 Dalton. In embodiments, $R^4$ has a molecule weight in the range of 50 to 3,000 Dalton. In embodiments, $R^4$ has a molecule weight in the range of 50 to 2,400 Dalton. In embodiments, $R^4$ has a molecule weight in the range of 50 to 2,280 Dalton. In embodiments, $R^4$ has a molecule weight in the range of 50 to 2,160 Dalton. In embodiments, $R^4$ has a molecule weight in the range of 50 to 2,040 Dalton. In embodiments, $R^4$ has a molecule weight in the range of 50 to 1,920 Dalton. In embodiments, $R^4$ has a molecule weight in the range of 50 to 1,800 Dalton. In embodiments, $R^4$ has a molecule weight in the range of 50 to 1,680 Dalton. In embodiments, $R^4$ has a molecule weight in the range of 50 to 1,560 Dalton. In embodiments, $R^4$ has a molecule weight in the range of 50 to 1,440 Dalton. In embodiments, $R^4$ has a molecule weight in the range of 50 to 1,320 Dalton. In embodiments, $R^4$ has a molecule weight in the range of 50 to 1,200 Dalton. In embodiments, $R^4$ has a molecule weight in the range of 50 to 1,080 Dalton. In embodiments, $R^4$ has a molecule weight in the range of 50 to 960 Dalton. In embodiments, $R^4$ has a molecule weight in the range of 50 to 840 Dalton. In embodiments, $R^4$ has a molecule weight in the range of 50 to 720 Dalton. In embodiments, $R^4$ has a molecule weight in the range of 50 to 600 Dalton. In embodiments, $R^4$ has a molecule weight in the range of 50 to 480 Dalton. In embodiments, $R^4$ has a molecule weight in the range of 50 to 360 Dalton. In embodiments, $R^4$ has a molecule weight in the range of 50 to 240 Dalton. In embodiments, $R^4$ has a molecule weight in the range of 50 to 180 Dalton. In embodiments, $R^4$ has a molecular weight of about 60 Dalton. In embodiments, $R^4$ has a molecular weight of about 120 Dalton. In embodiments, $R^4$ has a molecular weight of about 240 Dalton. In embodiments, $R^4$ has a molecular weight of about 360 Dalton. In embodiments, $R^4$ has a molecular weight of about 480 Dalton. In embodiments, $R^4$ has a molecular weight of about 600 Dalton. In embodiments, $R^4$ has a molecular weight of about 720 Dalton. In embodiments, $R^4$ has a molecular weight of about 840 Dalton. In embodiments, $R^4$ has a molecular weight of about 96 Dalton. In embodiments, $R^4$ has a molecular weight of about 1,080 Dalton. In embodiments, $R^4$ has a molecular weight of about 1,200 Dalton. In embodiments, $R^4$ has a molecular weight of about 1,320 Dalton. In embodiments, $R^4$ has a molecular weight of about 1,440 Dalton. In embodiments, $R^4$ has a molecular weight of about 1,560 Dalton. In embodiments, $R^4$ has a molecular weight of about 1,680 Dalton. In embodiments, $R^4$ has a molecular weight of about 1,800 Dalton. In embodiments, $R^4$ has a molecular weight of about 1,920 Dalton. In embodiments, $R^4$ has a molecular weight of about 2,040 Dalton. In embodiments, $R^4$ has a molecular weight of about 2,160 Dalton. In embodiments, $R^4$ has a molecular weight of about 2,280 Dalton. In embodiments, $R^4$ has a molecular weight of about 2,400 Dalton. In embodiments, $R^4$ has a molecular weight of about 3,000 Dalton. In embodiments, $R^4$ has a molecular weight of about 3,600 Dalton. In embodiments, $R^4$ has a molecular weight of about 4,200 Dalton. In embodiments, $R^4$ has a molecular weight of about 4,800 Dalton. In embodiments, $R^4$ has a molecular weight of about 5,400 Dalton. In embodiments, $R^4$ has a molecular weight of about 6,000 Dalton. In embodiments, $R^4$ has a molecular weight of about 7,200 Dalton. In embodiments, $R^4$ has a molecular weight of about 8,400 Dalton. In embodiments, $R^4$ has a molecular weight of about 9,600 Dalton. In embodiments, $R^4$ has a molecular weight of about 10,800 Dalton. In embodiments, $R^4$ has a molecular weight of about 12,000 Dalton. In embodiments, $R^4$ has a molecular weight of about 24,000 Dalton. In embodiments, $R^4$ has a molecular weight of about 36,000 Dalton. In embodiments, $R^4$ has a molecular weight of about 48,000 Dalton. In embodiments, $R^4$ has a molecular weight of about 60,000 Dalton. In embodiments, $R^4$ has a molecular weight of about 72,000 Dalton. In embodiments, $R^4$ has a molecular weight of about 84,000 Dalton. In embodiments, $R^4$ has a molecular weight of about 96,000 Dalton. In embodiments, $R^4$ has a molecular weight of about 108,000 Dalton. In embodiments, $R^4$ has a molecular weight of about 180,000 Dalton. In embodiments, $R^4$ has a molecular weight of about 240,000 Dalton.

In embodiments, $R^5$ has a molecule weight in the range of 50 to 240,000 Dalton. In embodiments, $R^5$ has a molecule weight in the range of 50 to 180,000 Dalton. In embodiments, $R^5$ has a molecule weight in the range of 50 to 120,000 Dalton. In embodiments, $R^5$ has a molecule weight in the range of 50 to 108,000 Dalton. In embodiments, $R^5$ has a molecule weight in the range of 50 to 96,000 Dalton. In embodiments, $R^5$ has a molecule weight in the range of 50 to 84,000 Dalton. In embodiments, $R^5$ has a molecule weight in the range of 50 to 72,000 Dalton. In embodiments, $R^5$ has a molecule weight in the range of 50 to 60,000 Dalton. In embodiments, $R^5$ has a molecule weight in the range of 50 to 48,000 Dalton. In embodiments, $R^5$ has a molecule weight in the range of 50 to 36,000 Dalton. In embodiments, $R^5$ has a molecule weight in the range of 50 to 24,000 Dalton. In embodiments, $R^5$ has a molecule weight in the range of 50 to 12,000 Dalton. In embodiments, $R^5$ has a molecule weight in the range of 50 to 10,800 Dalton. In embodiments, $R^5$ has a molecule weight in the range of 50 to 9,600 Dalton. In embodiments, $R^5$ has a molecule weight in the range of 50 to 8,400 Dalton. In embodiments, $R^5$ has a molecule weight in the range of 50 to 7,200 Dalton. In embodiments, $R^5$ has a molecule weight in the range of 50 to 6,000 Dalton. In embodiments, $R^5$ has a molecule weight in the range of 50 to 5,400 Dalton. In embodiments, $R^5$ has a molecule weight in the range of 50 to 4,800 Dalton. In embodiments, $R^5$ has a molecule weight in the range of 50 to 4,200 Dalton. In embodiments, $R^5$ has a molecule weight in the range of 50 to 3,600 Dalton. In embodiments, $R^5$ has a molecule weight in the range of 50 to 3,000 Dalton. In embodiments, $R^5$ has a molecule weight in the range of 50 to 2,400 Dalton. In embodiments, $R^5$ has a molecule weight in the range of 50 to 2,280 Dalton. In embodiments, $R^5$ has a molecule weight in the range of 50 to 2,160 Dalton. In embodiments, $R^5$ has a molecule weight in the range of 50 to 2,040 Dalton. In embodiments, $R^5$ has a molecule weight in the range of 50 to 1,920 Dalton. In embodiments, $R^5$ has a molecule weight in the range of 50 to 1,800 Dalton. In embodiments, $R^5$ has a molecule weight in the range of 50 to 1,680 Dalton. In embodiments, $R^5$ has a molecule weight in the range of 50 to 1,560 Dalton. In embodiments, $R^5$ has a molecule weight in the range of 50 to 1,440 Dalton. In embodiments, $R^5$ has a molecule weight in the range of 50 to 1,320 Dalton. In embodiments, $R^5$ has a molecule weight in the range of 50 to 1,200 Dalton. In embodiments, $R^5$ has a molecule weight in the range of 50 to 1,080 Dalton. In embodiments, $R^5$ has a molecule weight in the range of 50 to 960 Dalton. In embodiments, $R^5$ has a molecule weight in the range of 50 to 840 Dalton. In embodiments, $R^5$ has a molecule weight in the range of 50 to 720 Dalton. In embodiments, $R^5$ has a molecule weight in the range of 50 to 600 Dalton. In embodiments, $R^5$ has a molecule weight in the range of 50 to 480 Dalton. In embodiments, $R^5$ has a molecule weight in the range of 50 to 360 Dalton. In embodiments, $R^5$ has a molecule weight in the range of 50 to 240 Dalton. In embodiments, $R^5$ has a molecule weight in the range of 50 to 180 Dalton. In embodiments, $R^5$ has a molecular weight of about 60 Dalton. In embodiments, $R^5$ has a molecular weight of about 120 Dalton. In embodiments, $R^5$ has a molecular weight of about 240 Dalton. In embodiments, $R^5$ has a molecular weight of about 360 Dalton. In embodiments, $R^5$ has a molecular weight of about 480 Dalton. In embodiments, $R^5$ has a molecular weight of about 600 Dalton. In embodiments, $R^5$ has a molecular weight of about 720 Dalton. In embodiments, $R^5$ has a molecular weight of about 840 Dalton. In embodiments, $R^5$ has a molecular weight of about 960 Dalton. In embodiments, $R^5$ has a molecular weight of about 1,080 Dalton. In embodiments, $R^5$ has a molecular weight of about 1,200 Dalton. In embodiments, $R^5$ has a molecular weight of about 1,320 Dalton. In embodiments, $R^5$ has a molecular weight of about 1,440 Dalton. In embodiments, $R^5$ has a molecular weight of about 1,560 Dalton. In embodiments, $R^5$ has a molecular weight of about 1,680 Dalton. In embodiments, $R^5$ has a molecular weight of about 1,800 Dalton. In embodiments, $R^5$ has a molecular weight of about 1,920 Dalton. In embodiments, $R^5$ has a molecular weight of about 2,040 Dalton. In embodiments, $R^5$ has a molecular weight of about 2,160 Dalton. In embodiments, $R^5$ has a molecular weight of about 2,280 Dalton. In embodiments, $R^5$ has a molecular weight of about 2,400 Dalton. In embodiments, $R^5$ has a molecular weight of about 3,000 Dalton. In embodiments, $R^5$ has a molecular weight of about 3,600 Dalton. In embodiments, $R^5$ has a molecular weight of about 4,200 Dalton. In embodiments, $R^5$ has a molecular weight of about 4,800 Dalton. In embodiments, $R^5$ has a molecular weight of about 5,400 Dalton. In embodiments, $R^5$ has a molecular weight of about 6,000 Dalton. In embodiments, $R^5$ has a molecular weight of about 7,200 Dalton. In embodiments, $R^5$ has a molecular weight of about 8,400 Dalton. In embodiments, $R^5$ has a molecular weight of about 9,600 Dalton. In embodiments, $R^5$ has a molecular weight of about 10,800 Dalton. In embodiments, $R^5$ has a molecular weight of about 12,000 Dalton. In embodiments, $R^5$ has a molecular weight of about 24,000 Dalton. In embodiments, $R^5$ has a molecular weight of about 36,000 Dalton. In embodiments, $R^5$ has a molecular weight of about 48,000 Dalton. In embodiments, $R^5$ has a molecular weight of about 60,000 Dalton. In embodiments, $R^5$ has a molecular weight of about 72,000 Dalton. In embodiments, $R^5$ has a molecular weight of about 84,000 Dalton. In embodiments, $R^5$ has a molecular weight of about 96,000 Dalton. In embodiments, $R^5$ has a molecular weight of about 108,000 Dalton. In embodiments, $R^5$ has a molecular weight of about 180,000 Dalton. In embodiments, $R^5$ has a molecular weight of about 240,000 Dalton.

In embodiments, $R^6$ has a molecule weight in the range of 50 to 240,000 Dalton. In embodiments, $R^6$ has a molecule weight in the range of 50 to 180,000 Dalton. In embodiments, $R^6$ has a molecule weight in the range of 50 to 120,000 Dalton. In embodiments, $R^6$ has a molecule weight in the range of 50 to 108,000 Dalton. In embodiments, $R^6$ has a molecule weight in the range of 50 to 96,000 Dalton. In embodiments, $R^6$ has a molecule weight in the range of 50 to 84,000 Dalton. In embodiments, $R^6$ has a molecule weight in the range of 50 to 72,000 Dalton. In embodiments, $R^6$ has a molecule weight in the range of 50 to 60,000 Dalton. In embodiments, $R^6$ has a molecule weight in the range of 50 to 48,000 Dalton. In embodiments, $R^6$ has a molecule weight in the range of 50 to 36,000 Dalton. In embodiments, $R^6$ has a molecule weight in the range of 50 to 24,000 Dalton. In embodiments, $R^6$ has a molecule weight in the range of 50 to 12,000 Dalton. In embodiments, $R^6$ has a molecule weight in the range of 50 to 10,800 Dalton. In embodiments, $R^6$ has a molecule weight in the range of 50 to 9,600 Dalton. In embodiments, $R^6$ has a molecule weight in the range of 50 to 8,400 Dalton. In embodiments, $R^6$ has a molecule weight in the range of 50 to 7,200 Dalton. In embodiments, $R^6$ has a molecule weight in the range of 50 to 6,000 Dalton. In embodiments, $R^6$ has a molecule weight in the range of 50 to 5,400 Dalton. In embodiments, $R^6$ has a molecule weight in the range of 50 to 4,800 Dalton. In embodiments, $R^6$ has a molecule weight in the range of 50 to 4,200 Dalton. In embodiments, $R^6$ has a molecule weight in the range of 50 to 3,600 Dalton. In embodiments, $R^6$ has a molecule weight in the range of 50 to 3,000 Dalton. In embodiments, $R^6$ has a molecule weight in the range of 50 to 2,400 Dalton. In embodiments, $R^6$ has a molecule weight in the range of 50 to 2,280 Dalton. In embodiments, $R^6$ has a molecule weight in the range of 50 to 2,160 Dalton. In embodiments, $R^6$ has a molecule weight in the range of 50 to 2,040 Dalton. In embodiments, $R^6$ has a molecule weight in the range of 50 to 1,920 Dalton. In embodiments, $R^6$ has a molecule weight in the range of 50 to 1,800 Dalton. In embodiments, $R^6$ has a molecule weight in the range of 50 to 1,680 Dalton. In embodiments, $R^6$ has a molecule weight in the range of 50 to 1,560 Dalton. In embodiments, $R^6$ has a molecule weight in the range of 50 to 1,440 Dalton. In embodiments, $R^6$ has a molecule weight in the range of 50 to 1,320 Dalton. In embodiments, $R^6$ has a molecule weight in the range of 50 to 1,200 Dalton. In embodiments, $R^6$ has a molecule weight in the range of 50 to 1,080 Dalton. In embodiments, $R^6$ has a molecule weight in the range of 50 to 960 Dalton. In embodiments, $R^6$ has a molecule weight in the range of 50 to 840 Dalton. In embodiments, $R^6$ has a molecule weight in the range of 50 to 720 Dalton. In embodiments, $R^6$ has a molecule weight in the range of 50 to 600 Dalton. In embodiments, $R^6$ has a molecule weight in the range of 50 to 480 Dalton. In embodiments, $R^6$ has a molecule weight in the range of 50 to 360 Dalton. In embodiments, $R^6$ has a molecule weight in the range of 50 to 240 Dalton. In embodiments, $R^6$ has a molecule weight in the range of 50 to 180 Dalton. In embodiments, $R^6$ has a molecular weight of about 60 Dalton. In embodiments, $R^6$ has a molecular weight of about 120 Dalton. In embodiments, $R^6$ has a molecular weight of about 240 Dalton. In embodiments, $R^6$ has a molecular weight of about 360 Dalton. In embodiments, $R^6$ has a molecular weight of about 480 Dalton. In embodiments, $R^6$ has a molecular weight of about 600 Dalton. In embodiments, $R^6$ has a molecular weight of about 720 Dalton. In embodiments, $R^6$ has a molecular weight of about 840 Dalton. In embodiments, $R^6$ has a molecular weight of about 96 Dalton. In embodiments, $R^6$ has a molecular weight of about 1,080 Dalton. In embodiments, $R^6$ has a molecular weight of about 1,200 Dalton. In embodiments, $R^6$ has a molecular weight of about 1,320 Dalton. In embodiments, $R^6$ has a molecular weight of about 1,440 Dalton. In embodiments, $R^6$ has a molecular weight of about 1,560 Dalton. In embodiments, $R^6$ has a molecular weight of about 1,680 Dalton. In embodiments, $R^6$ has a molecular weight of about 1,800 Dalton. In embodiments, $R^6$ has a molecular weight of about 1,920 Dalton. In embodiments, $R^6$ has a molecular weight of about 2,040 Dalton. In embodiments, $R^6$ has a molecular weight of about 2,160 Dalton. In embodiments, $R^6$ has a molecular weight of about 2,280 Dalton. In embodiments, $R^6$ has a molecular weight of about 2,400 Dalton. In embodiments, $R^6$ has a molecular weight of about 3,000 Dalton. In embodiments, $R^6$ has a molecular weight of about 3,600 Dalton. In embodiments, $R^6$ has a molecular weight of about 4,200 Dalton. In embodiments, $R^6$ has a molecular weight of about 4,800 Dalton. In embodiments, $R^6$ has a molecular weight of about 5,400 Dalton. In embodiments, $R^6$ has a molecular weight of about 6,000 Dalton. In embodiments, $R^6$ has a molecular weight of about 7,200 Dalton. In embodiments, $R^6$ has a molecular weight of about 8,400 Dalton. In embodiments, $R^6$ has a molecular weight of about 9,600 Dalton. In embodiments, $R^6$ has a molecular weight of about 10,800 Dalton. In embodiments, $R^6$ has a molecular weight of about 12,000 Dalton. In embodiments, $R^6$ has a molecular weight of about 24,000 Dalton. In embodiments, $R^6$ has a molecular weight of about 36,000 Dalton. In embodiments, $R^6$ has a molecular weight of about 48,000 Dalton. In embodiments, $R^6$ has a molecular weight of about 60,000 Dalton. In embodiments, $R^6$ has a molecular weight of about 72,000 Dalton. In embodiments, $R^6$ has a molecular weight of about 84,000 Dalton. In embodiments, $R^6$ has a molecular weight of about 96,000 Dalton. In embodiments, $R^6$ has a molecular weight of about 108,000 Dalton. In embodiments, $R^6$ has a molecular weight of about 180,000 Dalton. In embodiments, $R^6$ has a molecular weight of about 240,000 Dalton.

In embodiments, $R^7$ has a molecule weight in the range of 50 to 240,000 Dalton. In embodiments, $R^7$ has a molecule weight in the range of 50 to 180,000 Dalton. In embodiments, $R^7$ has a molecule weight in the range of 50 to 120,000 Dalton. In embodiments, $R^7$ has a molecule weight in the range of 50 to 108,000 Dalton. In embodiments, $R^7$ has a molecule weight in the range of 50 to 96,000 Dalton. In embodiments, $R^7$ has a molecule weight in the range of 50 to 84,000 Dalton. In embodiments, $R^7$ has a molecule weight in the range of 50 to 72,000 Dalton. In embodiments, $R^7$ has a molecule weight in the range of 50 to 60,000 Dalton. In embodiments, $R^7$ has a molecule weight in the range of 50 to 48,000 Dalton. In embodiments, $R^7$ has a molecule weight in the range of 50 to 36,000 Dalton. In embodiments, $R^7$ has a molecule weight in the range of 50 to 24,000 Dalton. In embodiments, $R^7$ has a molecule weight in the range of 50 to 12,000 Dalton. In embodiments, $R^7$ has a molecule weight in the range of 50 to 10,800 Dalton. In embodiments, $R^7$ has a molecule weight in the range of 50 to 9,600 Dalton. In embodiments, $R^7$ has a molecule weight in the range of 50 to 8,400 Dalton. In embodiments, $R^7$ has a molecule weight in the range of 50 to 7,200 Dalton. In embodiments, $R^7$ has a molecule weight in the range of 50 to 6,000 Dalton. In embodiments, $R^7$ has a molecule weight in the range of 50 to 5,400 Dalton. In embodiments, $R^7$ has a molecule weight in the range of 50 to 4,800 Dalton. In embodiments, $R^7$ has a molecule weight in the range of 50 to 4,200 Dalton. In embodiments, $R^7$ has a molecule weight in the range of 50 to 3,600 Dalton. In embodiments, $R^7$ has a molecule weight in the range of 50 to 3,000 Dalton. In embodiments, $R^7$ has a molecule weight in the range of 50 to 2,400 Dalton. In embodiments, $R^7$ has a molecule weight in the range of 50 to 2,280 Dalton. In embodiments, $R^7$ has a molecule weight in the range of 50 to 2,160 Dalton. In embodiments, $R^7$ has a molecule weight in the range of 50 to 2,040 Dalton. In embodiments, $R^7$ has a molecule weight in the range of 50 to 1,920 Dalton. In embodiments, $R^7$ has a molecule weight in the range of 50 to 1,800 Dalton. In embodiments, $R^7$ has a molecule weight in the range of 50 to 1,680 Dalton. In embodiments, $R^7$ has a molecule weight in the range of 50 to 1,560 Dalton. In embodiments, $R^7$ has a molecule weight in the range of 50 to 1,440 Dalton. In embodiments, $R^7$ has a molecule weight in the range of 50 to 1,320 Dalton. In embodiments, $R^7$ has a molecule weight in the range of 50 to 1,200 Dalton. In embodiments, $R^7$ has a molecule weight in the range of 50 to 1,080 Dalton. In embodiments, $R^7$ has a molecule weight in the range of 50 to 960 Dalton. In embodiments, $R^7$ has a molecule weight in the range of 50 to 840 Dalton. In embodiments, $R^7$ has a molecule weight in the range of 50 to 720 Dalton. In embodiments, $R^7$ has a molecule weight in the range of 50 to 600 Dalton. In embodiments, $R^7$ has a molecule weight in the range of 50 to 480 Dalton. In embodiments, $R^7$ has a molecule weight in the range of 50 to 360 Dalton. In embodiments, $R^7$ has a molecule weight in the range of 50 to 240 Dalton. In embodiments, $R^7$ has a molecule weight in the range of 50 to 180 Dalton. In embodiments, $R^7$ has a molecular weight of about 60 Dalton. In embodiments, $R^7$ has a molecular weight of about 120 Dalton. In embodiments, $R^7$ has a molecular weight of about 240 Dalton. In embodiments, $R^7$ has a molecular weight of about 360 Dalton. In embodiments, $R^7$ has a molecular weight of about 480 Dalton. In embodiments, $R^7$ has a molecular weight of about 600 Dalton. In embodiments, $R^7$ has a molecular weight of about 720 Dalton. In embodiments, $R^7$ has a molecular weight of about 840 Dalton. In embodiments, $R^7$ has a molecular weight of about 96 Dalton. In embodiments, $R^7$ has a molecular weight of about 1,080 Dalton. In embodiments, $R^7$ has a molecular weight of about 1,200 Dalton. In embodiments, $R^7$ has a molecular weight of about 1,320 Dalton. In embodiments, $R^7$ has a molecular weight of about 1,440 Dalton. In embodiments, $R^7$ has a molecular weight of about 1,560 Dalton. In embodiments, $R^7$ has a molecular weight of about 1,680 Dalton. In embodiments, $R^7$ has a molecular weight of about 1,800 Dalton. In embodiments, $R^7$ has a molecular weight of about 1,920 Dalton. In embodiments, $R^7$ has a molecular weight of about 2,040 Dalton. In embodiments, $R^7$ has a molecular weight of about 2,160 Dalton. In embodiments, $R^7$ has a molecular weight of about 2,280 Dalton. In embodiments, $R^7$ has a molecular weight of about 2,400 Dalton. In embodiments, $R^7$ has a molecular weight of about 3,000 Dalton. In embodiments, $R^7$ has a molecular weight of about 3,600 Dalton. In embodiments, $R^7$ has a molecular weight of about 4,200 Dalton. In embodiments, $R^7$ has a molecular weight of about 4,800 Dalton. In embodiments, $R^7$ has a molecular weight of about 5,400 Dalton. In embodiments, $R^7$ has a molecular weight of about 6,000 Dalton. In embodiments, $R^7$ has a molecular weight of about 7,200 Dalton. In embodiments, $R^7$ has a molecular weight of about 8,400 Dalton. In embodiments, $R^7$ has a molecular weight of about 9,600 Dalton. In embodiments, $R^7$ has a molecular weight of about 10,800 Dalton. In embodiments, $R^7$ has a molecular weight of about 12,000 Dalton. In embodiments, $R^7$ has a molecular weight of about 24,000 Dalton. In embodiments, $R^7$ has a molecular weight of about 36,000 Dalton. In embodiments, $R^7$ has a molecular weight of about 48,000 Dalton. In embodiments, $R^7$ has a molecular weight of about 60,000 Dalton. In embodiments, $R^7$ has a molecular weight of about 72,000 Dalton. In embodiments, $R^7$ has a molecular weight of about 84,000 Dalton. In embodiments, $R^7$ has a molecular weight of about 96,000 Dalton. In embodiments, $R^7$ has a molecular weight of about 108,000 Dalton. In embodiments, $R^7$ has a molecular weight of about 180,000 Dalton. In embodiments, $R^7$ has a molecular weight of about 240,000 Dalton.

In embodiments, the first peptidyl moiety $R^4$ includes a peptide of 1 to 200 amino acid residues; the second peptidyl moiety $R^5$ includes a peptide of 1 to 200 amino acid residues; the third peptidyl moiety $R^6$ includes a peptide of 1 to 200 amino acid residues; and the fourth peptidyl moiety $R^7$ includes a peptide of 1 to 200 amino acid residues. In embodiments, the first peptidyl moiety $R^4$ has a molecule weight in the range 50 to 24,000 Dalton; the second peptidyl moiety $R^5$ has a molecule weight in the range 50 to 24,000 Dalton; the third peptidyl moiety $R^6$ has a molecule weight in the range 50 to 24,000 Dalton; and the fourth peptidyl moiety $R^7$ has a molecule weight in the range 50 to 24,000 Dalton.

In another aspect, there is provide a composition with structure of Formula (I):

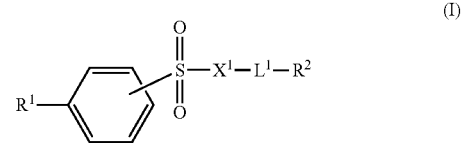

wherein $R^1$ is a protein binding moiety; $X^1$ is —O—, —NH— or —S—; $L^1$ is a lysine, histidine, cysteine, serine, threonine or tyrosine together with the side chain —O—, —NH— or —S— to which it is attached; and $R^2$ is a target protein moiety.

The term "protein binding moiety" refers to a chemical species, e.g., a biomolecule and derivatives thereof including compositions disclosed herein, which is capable of modulating (e.g., increasing or decreasing) the function (e.g., biological activity) of another chemical species. In embodiments, the protein binding moiety covalently binds another chemical species. In embodiments, the protein binding moiety non-covalently binds another chemical species. In embodiments, the protein binding moiety is a biomolecule and the another chemical species is a biomolecule. In embodiments, the protein binding moiety increases the biological activity of the another chemical species, e.g., increases the binding, affinity, enzymatic activity and the like, of the another chemical species. In embodiments, the protein binding moiety decreases the biological activity of the another chemical species, e.g., decreases the binding, affinity, enzymatic activity and the like. In embodiments, $R^1$ is a biomolecule which is covalently attached to the sulfonylphenyl functionality set forth in Formula (I).

The terms "together with the side chain —O—, —NH— or —S— to which it is attached" and the like refer to a side chain nitrogen (i.e., —NH—) attached to an internal or terminal lysine or histidine residue of a target protein moiety $R^2$, or to a side chain oxygen (i.e., —O—) attached to an internal or terminal serine, threonine or tyrosine residue of a target protein moiety $R^2$, or to a side chain sulfur (i.e., —S—) attached to an internal or terminal cysteine residue of a target protein moiety $R^2$. The term "target protein moiety" refers to a targeted biomolecule, e.g., a biomolecule having e.g., a regulatory role in a cell. In embodiments, $L^1$ is a lysine residue together with the side chain nitrogen to which it is attached. In embodiments, $L^1$ is a histidine residue together with the side chain nitrogen to which it is attached. In embodiments, $L^1$ is a serine residue together with the side chain oxygen to which it is attached. In embodiments, $L^1$ is a threonine residue together with the side chain oxygen to which it is attached. In embodiments, $L^1$ is a tyrosine residue together with the side chain oxygen to which it is attached. In embodiments, $L^1$ is a cysteine residue together with the side chain sulfur to which it is attached.

In embodiments, the target protein moiety includes a protein binding interface, active site or allosteric site, and the protein binding moiety is capable of binding the target protein moiety at the protein binding interface, active site or allosteric site. In embodiments, the target protein moiety includes a protein binding interface. In embodiments, the target protein moiety includes an active site. In embodiments, the target protein moiety includes an allosteric site.

The term "protein binding interface" in this context refers, in the usual and customary sense, to a three-dimension region of a target protein moiety, which region can form at least part of an interface (e.g., mutual contact surface) with another chemical species (e.g., a protein binding moiety as disclosed herein and derivatives thereof) upon binding. The protein binding interface can be a contiguous primary structural region, or the protein binding interface can include a plurality of discontinuous primary structural regions. The terms "primary structure," "primary structural region" and the like refer, in the usual and customary sense, to the linear amino acid sequence of a protein or peptide. In embodiments, the protein binding interface of the target protein $R^2$ can bind a region of protein binding moiety $R^1$. In embodiments, binding at the protein binding interface of the target protein moiety can modulate (e.g., increase or decrease) the biological activity of the target protein moiety.

The term "active site" in this context refers, in the usual and customary sense, to a region in the three dimensional structure of a target protein moiety, which region is involved in binding, catalysis, or other biological activity. In embodiments, the active site of target protein moiety $R^2$ can bind a region of protein binding moiety $R^1$. In embodiments, binding at the active site of the target protein moiety can modulate (e.g., increase or decrease) the biological activity of the target protein moiety.

The term "allosteric site" in this context refers, in the usual and customary sense, to a region in the three dimensional structure of a target protein moiety, which region can influence the binding, catalysis, or other biological activity of the target protein moiety, e.g., at its active site, without necessarily being directly involved in the binding, catalysis, or other biological activity. In embodiments, target protein moiety $R^2$ can bind at an allosteric site to protein binding moiety $R^1$, thereby modulating (e.g., increasing or decreasing) the biological activity of the target protein moiety.

In embodiments, the protein binding moiety is capable of binding the target protein moiety at the protein binding interface, active site or allosteric site thereof.

In embodiments, the protein binding moiety is capable of activating or inhibiting the target protein moiety upon binding. In embodiments, activation of the target protein moiety results in increase or enhancement of the biological activity of the target protein moiety. In embodiments, activation of the target protein moiety results in modulation (e.g., increase or decrease) of the biological activity of another biomolecule, e.g., another biomolecule under regulatory control by the target protein moiety. In embodiments, inhibition of the target protein moiety results in diminution or curtailment of the biological activity of the target protein moiety. In embodiments, inhibition of the target protein results in modulation (e.g., activation or diminution) of the biological activity of another biomolecule, e.g., rescue of deactivation of a tumor suppressor protein, thereby providing elevated biological activity of the other biomolecule, e.g., increase in tumor suppressor activity.

Methods

In another aspect, there is provided a method of covalently binding a peptide to a protein, the method comprising combining a compound of Formula (IV):

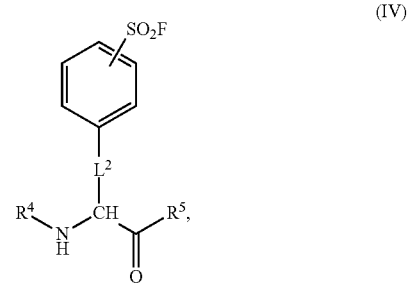

with a protein, thereby forming a compound of Formula (V):

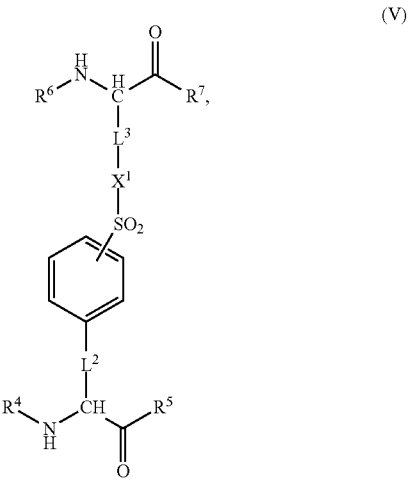

wherein: $R^4$ is a first peptidyl moiety; $R^5$ is a second peptidyl moiety; $R^6$ is a third peptidyl moiety; $R^7$ is a fourth peptidyl moiety; $L^2$ and $L^3$ are independently a bond, $-S(O)_2-$, $-NH-$, $-O-$, $-S-$, $-C(O)-$, $-NHC(O)-$, $-C(O)NH-$, $-NHC(O)NH-$, $-C(O)O-$, $-OC(O)-$, $-NHS(O)_2-$, $-S(O)_2NH-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $X^1$ is $-NH-$, $-O-$, or $-S-$.

In embodiments, $L^2$ is substituted or unsubstituted alkyl. In embodiments, $L^2$ is substituted or unsubstituted $C_1$-$C_{10}$ alkyl. In embodiments, $L^2$ is unsubstituted $C_1$-$C_{10}$ alkyl. In embodiments, $L^2$ is methylene.

In embodiments, $L^2$ is substituted or unsubstituted heteroalkyl. In embodiments, $L^2$ is substituted or unsubstituted $C_1$-$C_{10}$ heteroalkyl. In embodiments, $L^2$ is unsubstituted $C_1$-$C_{10}$ heteroalkyl. In embodiments, $L^2$ is substituted $C_1$-$C_{10}$ heteroalkyl. In embodiments, $L^2$ is $-(CH_2)_nNH-C(O)-$, wherein n is an integer in the range 1-10. In embodiments, n is 1, 2, 3, 4, 5, 6, 7, 8, 9 or 10. In embodiments, n is 1. In embodiments, n is 2. In embodiments, n is 3. In embodiments, n is 4. In embodiments, n is 5. In embodiments, n is 6. In embodiments, n is 7. In embodiments, n is 8. In embodiments, n is 9. In embodiments, n is 10.

In embodiments, the compounds of Formula (IV) has the structure of Formula (IVa):

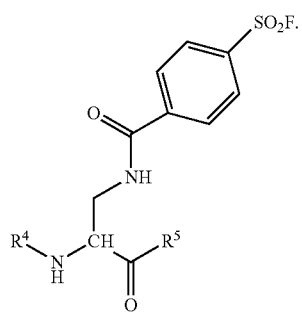

(IVa)

In embodiments, -$L^3$-$X^1$— is the reacted product of a lysine side chain, histidine side chain, cysteine side chain, serine side chain, threonine side chain or tyrosine side chain. In embodiments, -$L^3$-$X^1$— is the reacted product of a lysine side chain. In embodiments, -$L^3$-$X^1$— is the reacted product of a cysteine side chain. In embodiments, -$L^3$-$X^1$— is the reacted product of a serine, threonine or tyrosine side chain.

In embodiments, the first peptidyl moiety $R^4$ is 1 to 200 amino acid residues in length; the second peptidyl moiety $R^5$ is 1 to 200 amino acid residues in length; the third peptidyl moiety $R^6$ is 1 to 200 amino acid residues in length; and the fourth peptidyl moiety $R^7$ is 1 to 200 amino acid residues in length.

In embodiments, the first peptidyl moiety $R^4$ includes a number of amino acid residues as set forth above further to compounds of Formulae (III), (IV), (V), or embodiments thereof.

In embodiments, the second peptidyl moiety $R^5$ includes a number of amino acid residues as set forth above further to compounds of Formulae (III), (IV), (V), or embodiments thereof.

In embodiments, the third peptidyl moiety $R^6$ includes a number of amino acid residues as set forth above further to compounds of Formulae (III), (IV), (V), or embodiments thereof.

In embodiments, the fourth peptidyl moiety $R^7$ includes a number of amino acid residues as set forth above further to compounds of Formulae (III), (IV), (V), or embodiments thereof.

In embodiments, T($R^4$+$R^5$) includes a number of amino acid residues as set forth above further to compounds of Formulae (III), (IV), (V), or embodiments thereof.

In embodiments, T($R^6$+$R^7$) includes a number of amino acid residues as set forth above further to compounds of Formulae (III), (IV), (V), or embodiments thereof.

In embodiments, $R^4$ has a molecule weight as set forth above further to compounds of Formulae (III), (IV), (V), or embodiments thereof.

In embodiments, $R^5$ has a molecule weight as set forth above further to compounds of Formulae (III), (IV), (V), or embodiments thereof.

In embodiments, $R^6$ has a molecule weight as set forth above further to compounds of Formulae (III), (IV), (V), or embodiments thereof.

In embodiments, $R^7$ has a molecule weight as set forth above further to compounds of Formulae (III), (IV), (V), or embodiments thereof.

In embodiments, the first peptidyl moiety $R^4$ includes a peptide of 1 to 200 amino acid residues; the second peptidyl moiety $R^5$ includes a peptide of 1 to 200 amino acid residues; the third peptidyl moiety $R^6$ includes a peptide of 1 to 200 amino acid residues; and the fourth peptidyl moiety $R^7$ includes a peptide of 1 to 200 amino acid residues. In embodiments, the first peptidyl moiety $R^4$ has a molecule weight in the range 50 to 24,000 Dalton; the second peptidyl moiety $R^5$ has a molecule weight in the range 50 to 24,000 Dalton; the third peptidyl moiety $R^6$ has a molecule weight in the range 50 to 24,000 Dalton; and the fourth peptidyl moiety $R^7$ has a molecule weight in the range 50 to 24,000 Dalton.

In embodiments, formation of a compound of Formula (V) occurs when the sulfonyl fluoride moiety of a compound of Formula (IV) or an embodiment thereof is within sufficient proximity of a lysine, histidine, cysteine, serine, threonine or tyrosine to react with the side chain of the lysine, histidine, cysteine, serine, threonine or tyrosine. The term "sufficient proximity" or the like refers to a separation distance between reactants which is sufficiently close to allow chemical reaction, e.g., bond formation, to occur.

In embodiments, the first and second peptidyl moieties $R^4$ and $R^5$, together with the atoms covalently joining them, form a protein binding moiety.

In embodiments, the third and fourth peptidyl moieties $R^6$ and $R^7$, together with the atoms covalently joining them, form a target protein moiety.

In embodiments, the protein moiety includes a protein binding interface, active site or allosteric site, and the protein binding moiety is capable of binding to the target protein moiety at the protein binding interface, active site or allosteric site. In embodiments, the protein binding moiety is capable of activating or inhibiting the biological activity of the target protein moiety upon binding. In embodiments, upon covalent binding of the compound of Formula (IV) to the target protein, the activity of the target protein is increased or decreased. In embodiments, the activity of the target protein includes binding to another protein.

In another aspect, there is provided a method of binding a target protein. The method includes: a) contacting a covalent protein binder having structure of Formula (II) with a target protein:

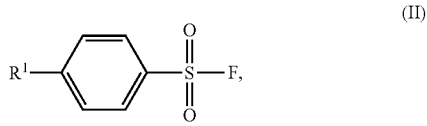

(II)

wherein $R^1$ is a protein binding moiety; and b) allowing the covalent protein binder to covalently bind to a lysine, histidine, cysteine, serine, threonine or tyrosine of the target protein.

The term "binding a target protein" and the like refers, in the usual and customary sense, to chemical binding (e.g., covalent or non-covalent binding) to a target protein. The term "covalent protein binder" and the like refers, in the usual and customary sense, to a chemical species, e.g., a compound as disclosed herein and derivatives thereof, which can undergo covalent bond formation and attachment to a target protein.

In embodiments, the lysine, histidine, cysteine, serine, threonine or tyrosine is within a protein binding interface, an active site or allosteric site of the target protein. In embodiments, the lysine, histidine, cysteine, serine, threonine or tyrosine is within a protein binding interface of the target protein. In embodiments, the lysine, histidine, cysteine, serine, threonine or tyrosine is within an active site of the target protein. In embodiments, the lysine, histidine, cysteine, serine, threonine or tyrosine is within an allosteric site of the target protein.

In embodiments, upon covalent binding of the covalent protein binder to the target protein, the biological activity of the target protein is increased or decreased. In embodiments, the biological activity is increased. In embodiments, the biological activity is decreased. In embodiments, the biological activity of the target protein includes binding to another protein. In embodiments, the biological activity of the target protein is binding to another protein. The term "covalent binding" refers, in the usual and customary sense, to binding which includes formation of a chemical bond.

In embodiments, the covalent binding occurs when the sulfonyl fluoride moiety of the covalent protein binder is within sufficient proximity of the lysine, histidine, cysteine, serine, threonine or tyrosine to react with the side chain nitrogen (—NH—), oxygen (—O—) or sulfur (—S—) of the lysine, histidine, cysteine, serine, threonine or tyrosine. In embodiments, the sulfonyl fluoride moiety of the covalent protein binder is within sufficient proximity to the side chain nitrogen of the histidine to afford covalent binding. In embodiments, the sulfonyl fluoride moiety of the covalent protein binder is within sufficient proximity to the side chain nitrogen of the lysine to afford covalent binding. In embodiments, the sulfonyl fluoride moiety of the covalent protein binder is within sufficient proximity to the side chain oxygen of the serine to afford covalent binding. In embodiments, the sulfonyl fluoride moiety of the covalent protein binder is within sufficient proximity to the side chain oxygen of the threonine to afford covalent binding. In embodiments, the sulfonyl fluoride moiety of the covalent protein binder is within sufficient proximity to the side chain oxygen of the tyrosine to afford covalent binding. In embodiments, the sulfonyl fluoride moiety of the covalent protein binder is within sufficient proximity to the side chain sulfur of the cysteine to afford covalent binding.

EMBODIMENTS

Embodiments contemplated herein include embodiments P1 to P8 following.

Embodiment P1

A composition with structure of Formula (I):

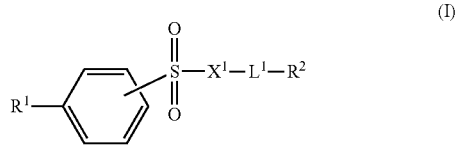

wherein $R^1$ is a protein binding moiety; $X^1$ is —O—, —NH— or —S—; $L^1$ is a lysine, histidine, cysteine, serine, threonine or tyrosine together with the side chain —O—, —NH— or —S— to which it is attached; and $R^2$ is a target protein moiety.

Embodiment P2

The composition according to embodiment P1, wherein: said target protein moiety comprises a protein binding interface, active site or allosteric site; and said protein binding moiety is capable of binding said target protein moiety at said protein binding interface, active site or allosteric site.

Embodiment P3

The composition according to embodiment P2, wherein said protein binding moiety is capable of activating or inhibiting said target protein moiety upon binding.

Embodiment P4

A method of binding a target protein, said method comprising: a) contacting a covalent protein binder having structure of Formula (II) with a target protein:

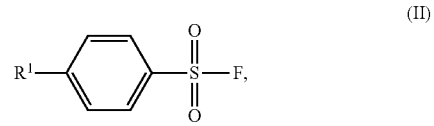

wherein $R^1$ is a protein binding moiety; and b) allowing said covalent protein binder to covalently bind to a lysine, histidine, cysteine, serine, threonine or tyrosine of said target protein.

Embodiment P5

The method according to embodiment P4, wherein said lysine, histidine, cysteine, serine, threonine or tyrosine is within a protein binding interface, active site or allosteric site of said target protein.

Embodiment P6

The method according to embodiment P4, wherein upon covalent binding of said covalent protein binder to said target protein, the activity of said target protein is increased or decreased.

Embodiment P7

The method according to embodiment P6, wherein said biological activity of said target protein comprises binding to another protein.

Embodiment P8

The method according to embodiment P6, wherein said covalent binding occurs when the sulfonyl fluoride of said covalent protein binder is within sufficient proximity of said lysine, histidine, cysteine, serine, threonine or tyrosine to react with the side chain of said lysine, histidine, cysteine, serine, threonine or tyrosine.

Further embodiments contemplated herein include embodiments 1 to 61 following.

Embodiment 1

A compound of Formula (III),

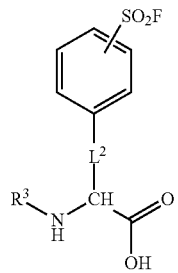

wherein $R^3$ is hydrogen or an amino protecting group; $L^2$ is a bond, —S(O)$_2$—, —NH—, —O—, —S—, —C(O)—, —NHC(O)—, —C(O)NH—, —NHC(O)NH—, —C(O)O—, —OC(O)—, —NHS(O)$_2$—, —S(O)$_2$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 2

The compound according to embodiment 1, wherein said $L^2$ is substituted or unsubstituted alkyl.

Embodiment 3

The compound according to embodiment 2, wherein said $L^2$ is substituted or unsubstituted $C_1$-$C_{10}$ alkyl.

Embodiment 4

The compound according to embodiment 3, wherein said $L^2$ is unsubstituted $C_1$-$C_{10}$ alkyl.

Embodiment 5

The compound according to embodiment 4, wherein said $L^2$ is methylene.

Embodiment 6

The compound according to embodiment 1, wherein said $L^2$ is substituted or unsubstituted heteroalkyl.

Embodiment 7

The compound according to embodiment 6, wherein said $L^2$ is substituted or unsubstituted 2 to 10 membered heteroalkyl.

Embodiment 8

The compound according to embodiment 7, wherein said $L^2$ is unsubstituted 2 to 10 membered heteroalkyl.

Embodiment 9

The compound according to embodiment 7, wherein said $L^2$ is oxo substituted 2 to 10 membered heteroalkyl.

Embodiment 10

The compound according to embodiment 9, wherein said $L^2$ is —(CH$_2$)$_n$—NH—C(O)—, wherein n is an integer in the range 1-10.

Embodiment 11

The compound according to embodiment 10, wherein n is 1.

Embodiment 12

The compound according to embodiment 1, wherein said compound has the structure of Formula (IIIa):

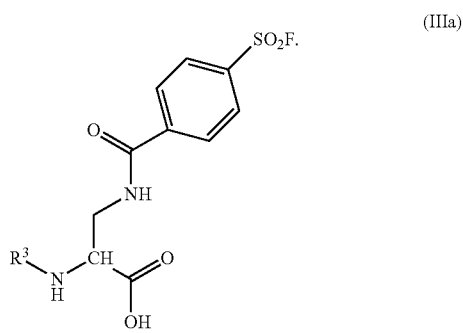

Embodiment 13

The compound according to embodiment 1, wherein $R^3$ is hydrogen.

Embodiment 14

The compound according to embodiment 1, wherein $R^3$ is an amino protecting group.

Embodiment 15

The composition according to embodiment 14, wherein said amino protecting group is tert-butyloxycarbonyl (tBoc), 9H-fluoren-9-ylmethoxycarbonyl (Fmoc), benzyloxy-carbonyl (Z), allyloxycarbonyl (Alloc), 4-methyltrityl (Mtt), 1-(4, 4-Dimethyl-2,6-dioxocyclohex-1-ylidene)-3-ethyl (Dde), or 1-(4,4-Dimethyl-2,6-dioxocyclohex-1-ylidene)-3-methylbutyl (ivDde).

Embodiment 16

The composition according to embodiment 15, wherein said amino protecting group is Fmoc.

Embodiment 17

A compound of Formula (IV),

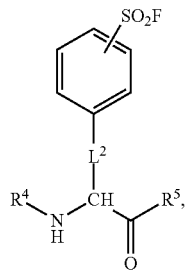

wherein: $R^4$ is a first peptidyl moiety; $R^5$ is a second peptidyl moiety; and $L^2$ is a bond, —S(O)$_2$—, —NH—, —O—, —S—, —C(O)—, —NHC(O)—, —C(O)NH—, —NHC(O)NH—, —C(O)O—, —OC(O)—, —NHS(O)$_2$—, —S(O)$_2$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 18

The compound according to embodiment 17, wherein said $L^2$ is substituted or unsubstituted alkyl.

Embodiment 19

The compound according to embodiment 18, wherein said $L^2$ is substituted or unsubstituted $C_1$-$C_{10}$ alkyl.

Embodiment 20

The compound according to embodiment 19, wherein said $L^2$ is unsubstituted $C_1$-$C_{10}$ alkyl.

Embodiment 21

The compound according to embodiment 20, wherein said $L^2$ is methylene.

Embodiment 22

The compound according to embodiment 17, wherein said $L^2$ is substituted or unsubstituted heteroalkyl.

Embodiment 23

The compound according to embodiment 22, wherein said $L^2$ is substituted or unsubstituted $C_1$-$C_{10}$ heteroalkyl.

Embodiment 24

The compound according to embodiment 23, wherein said $L^2$ is unsubstituted $C_1$-$C_{10}$ heteroalkyl.

Embodiment 25

The compound according to embodiment 23, wherein said $L^2$ is substituted $C_1$-$C_{10}$ heteroalkyl.

Embodiment 26

The compound according to embodiment 25, wherein said $L^2$ is —(CH$_2$)$_n$—NH—C(O)—, wherein n is an integer in the range 1-10.

Embodiment 27

The compound according to embodiment 26, wherein n is 1.

Embodiment 28

The compound of Formula (IV) with structure of Formula (IVa):

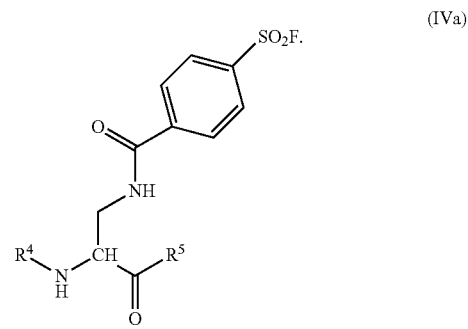

Embodiment 29

A compound of Formula (V):

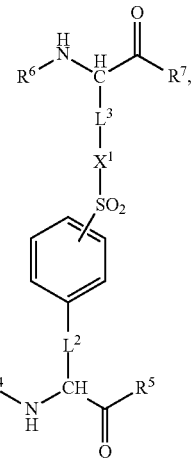

wherein: $R^4$ is a first peptidyl moiety; $R^5$ is a second peptidyl moiety; $R^6$ is a third peptidyl moiety; $R^7$ is a fourth peptidyl moiety; $L^2$ and $L^3$ are independently a bond, —S(O)$_2$—, —NH—, —O—, —S—, —C(O)—, —NHC(O)—, —C(O)NH—, —NHC(O)NH—, —C(O)O—, —OC(O)—, —NHS(O)$_2$—, —S(O)$_2$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $X^1$ is —NH—, —O—, or —S—.

Embodiment 30

The compound according to embodiment 29, wherein said $L^2$ is substituted or unsubstituted alkyl.

Embodiment 31

The compound according to embodiment 30, wherein said $L^2$ is substituted or unsubstituted $C_1$-$C_{10}$ alkyl.

Embodiment 32

The compound according to embodiment 31, wherein said $L^2$ is unsubstituted $C_1$-$C_{10}$ alkyl.

Embodiment 33

The compound according to embodiment 32, wherein said $L^2$ is methylene.

Embodiment 34

The compound according to embodiment 29, wherein said $L^2$ is substituted or unsubstituted heteroalkyl.

Embodiment 35

The compound according to embodiment 34, wherein said $L^2$ is substituted or unsubstituted $C_1$-$C_{10}$ heteroalkyl.

Embodiment 36

The compound according to embodiment 35, wherein said $L^2$ is unsubstituted $C_1$-$C_{10}$ heteroalkyl.

Embodiment 37

The compound according to embodiment 35, wherein said $L^2$ is substituted $C_1$-$C_{10}$ heteroalkyl.

Embodiment 38

The compound according to embodiment 37, wherein said $L^2$ is —$(CH_2)_n$NH—C(O)—, wherein n is an integer in the range 1-10.

Embodiment 39

The compound according to embodiment 38, wherein n is 1.

Embodiment 40

The compound according to embodiment 29, wherein -$L^3$-$X^1$— is the reacted product of a lysine side chain, histidine side chain, cysteine side chain, serine side chain, threonine side chain or tyrosine side chain.

Embodiment 41

The compound according to embodiment 40, wherein -$L^3$-$X^1$— is the reacted product of a lysine side chain.

Embodiment 42

The compound according to embodiment 40, wherein -$L^3$-$X^1$— is the reacted product of a cysteine side chain.

Embodiment 43

The compound according to embodiment 40, wherein -$L^3$-$X^1$— is the reacted product of a serine, threonine or tyrosine side chain.

Embodiment 44

A method of covalently binding a peptide to a protein, the method comprising combining a compound of Formula (IV):

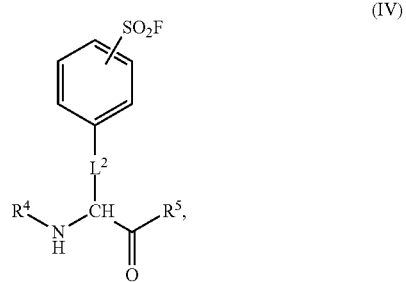

with a protein, thereby forming a compound of Formula (V):

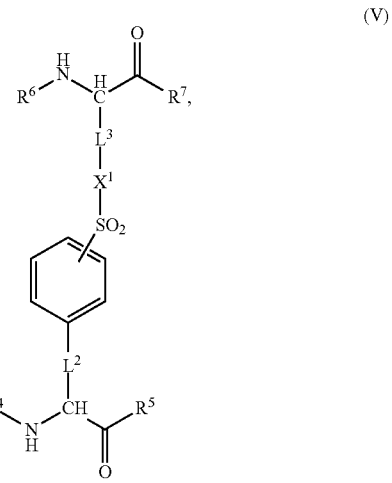

wherein: $R^4$ is a first peptidyl moiety; $R^5$ is a second peptidyl moiety; $R^6$ is a third peptidyl moiety; $R^7$ is a fourth peptidyl moiety; $L^2$ and $L^3$ are independently a bond, —S(O)$_2$—, —NH—, —O—, —S—, —C(O)—, —NHC(O)—, —C(O)NH—, —NHC(O)NH—, —C(O)O—, —OC(O)—, —NHS(O)$_2$—, —S(O)$_2$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $X^1$ is —NH—, —O—, or —S—.

Embodiment 45

The method according to embodiment 44, wherein said $L^2$ is substituted or unsubstituted alkyl.

Embodiment 46

The method according to embodiment 45, wherein said $L^2$ is substituted or unsubstituted $C_1$-$C_{10}$ alkyl.

Embodiment 47

The method according to embodiment 46, wherein said $L^2$ is unsubstituted $C_1$-$C_{10}$ alkyl.

Embodiment 48

The method according to embodiment 47, wherein said $L^2$ is methylene.

Embodiment 49

The method according to embodiment 44, wherein said $L^2$ is substituted or unsubstituted heteroalkyl.

Embodiment 50

The method according to embodiment 49, wherein said $L^2$ is substituted or unsubstituted $C_1$-$C_{10}$ heteroalkyl.

Embodiment 51

The method according to embodiment 50, wherein said $L^2$ is unsubstituted $C_1$-$C_{10}$ heteroalkyl.

Embodiment 52

The method according to embodiment 50, wherein said $L^2$ is substituted $C_1$-$C_{10}$ heteroalkyl.

Embodiment 53

The method according to embodiment 52, wherein said $L^2$ is —$(CH_2)_n$—NH—C(O)—, wherein n is an integer in the range 1-10.

Embodiment 54

The method according to embodiment 53, wherein n is 1.

Embodiment 55

The method according to embodiment 44, wherein said compound of Formula (IV) has structure of Formula (IVa):

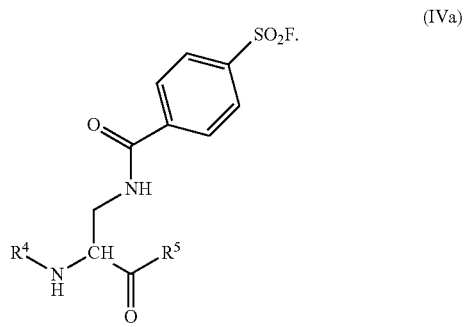

(IVa)

Embodiment 56

The method according to embodiment 44, wherein -$L^3$-$X^1$— is the reacted product of a lysine side chain, histidine side chain, cysteine side chain, serine side chain, threonine side chain or tyrosine side chain.

Embodiment 57

The method according to embodiment 56, wherein -$L^3$-$X^1$— is the reacted product of a lysine side chain.

Embodiment 58

The method according to embodiment 56, wherein -$L^3$-$X^1$— is the reacted product of a cysteine side chain.

Embodiment 59

The method according to embodiment 56, wherein -$L^3$-$X^1$— is the reacted product of a serine, threonine or tyrosine side chain.

Embodiment 60

The method according to embodiment 44, wherein: said first peptidyl moiety $R^4$ is 1 to 200 amino acid residues in length; said second peptidyl moiety $R^5$ is 1 to 200 amino acid residues in length; said third peptidyl moiety $R^6$ is 1 to 200 amino acid residues in length; and said fourth peptidyl moiety $R^7$ is 1 to 200 amino acid residues in length.

Embodiment 61

The method according to embodiment 60, wherein said first peptidyl moiety $R^4$ is 5 0 to 24,000 Daltons; said second peptidyl moiety $R^5$ is 50 to 24,000 Daltons; said third peptidyl moiety $R^6$ is 50 to 24,000 Daltons; and said fourth peptidyl moiety $R^7$ is 50 to 24,000 Daltons.

EXAMPLES

Example 1—Proximity-Enabled Bioreactivity to Generate Covalent Peptide Inhibitors of p53-Mdm4

Abstract.

Although small molecule covalent inhibitors have been widely explored, macromolecular covalent inhibitors are more difficult to design and implement. Here we present a strategy to enable a peptide to bind to its target protein covalently via proximity-enabled bioreactivity, improving its activity of inhibiting the p53-Mdm4 interaction by 10-fold.

Introduction

In human cancers elevated levels of the oncoproteins Mdm2 and Mdm4 result in deactivation of the tumor suppressor protein p53 [1,2]. Upon binding to p53, both Mdm2 and Mdm4 can block the transcriptional activity of p53, and Mdm2 also ubiquitylates p53 leading to proteasomal degradation. Attenuated p53 fails to regulate growth arrest and cell death upon DNA damage, directly contributing to tumor development, malignant progression, poor prognosis, and resistance to treatment [3]. Conversely, reactivation of endogenous p53 activity can reduce the growth of tumors in vivo by inducing apoptosis, senescence, and innate inflammatory responses [4]. Therefore, the inhibition of p53-Mdm2 or p53-Mdm4 interactions to restore p53 activity is an attractive and viable approach for cancer therapy [1,5].

Stapled peptides are an emerging class of biologics capable of disrupting p53-Mdm2 or p53-Mdm4 interactions [6-9]. The staple is a chemically introduced linkage of the side chains of two residues, which is expected to improve the stability and cellular uptake of the resultant peptide [10,11]. Compared with small molecules, peptide inhibitors show higher specificity toward the target protein due to their larger interaction interface. Indeed, the most studied stapled peptide SAHp53-8 has an $IC_{50}$ for Mdm2 ten-fold better than that of the small molecule inhibitor Nutlin-3a in vitro. While the SAHp53-8 shows high affinities in vitro (~55 nm) [7], its activity on the cellular level is reduced, possibly due to the presence of serum and inefficient cellular uptake [12-14]. Potential solutions are to increase cellular uptake and to further improve inhibitor affinity. To date, it remains to be demonstrated whether a highly active peptide targeting Mdm2 or Mdm4 with nanomolar affinity can be developed to reactivate p53 effectively without being toxic to cells.

Small molecules can react with the catalytic residues of proteins or tether to proteins via ligand-directed chemistry; such covalent reactivity has been exploited to improve the drug potency [15] or to label protein selectively [16]. In contrast, macromolecular covalent inhibitors are difficult to design and implement. Due to increased molecular weight and bulk, macromolecules such as peptide inhibitors usually cannot reach the active site of target proteins but gain access to protein surface or protein-protein interacting interface, where catalytic residues are often lacking for covalent bond formation. Here we present a new strategy to enable a peptide inhibitor to bind with the target protein covalently through proximity-enabled bioreactivity at mild conditions (FIG. 1) [17-19]. An otherwise chemically stable unnatural amino acid (Uaa) introduced into the peptide reacts with the target natural amino acid of the protein only when the peptide binds with the protein and brings the Uaa into proximity of the target natural amino acid. The resultant permanent linkage prevents dissociation and improves peptide inhibition efficiency. We demonstrated this principle by developing a stapled peptide to bind Mdm4 covalently, inhibiting p53-Mdm4 interaction more effectively.

To minimize nonspecific reactivity, the Uaa preferably remains chemically stable until it is in proximity to its target natural amino acid residue, when increased effective concentrations accelerate the reaction. Lysine or histidine are frequently found on protein surfaces, and are amenable to react with a variety of functional groups at neutral pH [18-30]. Recently, sulfur fluoride exchange (SuFEx) of sulfonyl fluorides ($-SO_2F$) was highlighted as a good reaction for click chemistry [21]. Aryl sulfonyl fluorides ($Ar-SO_2F$) can be attacked by nucleophiles such as lysine residues to form a stable sulfonamide bond [21-23]. Thereby, the sulfonyl fluoride function is stable towards hydrolysis in a wide range of pH making it an ideal "silent" group for biological applications and peptide inhibitors [24].

Results and Discussion

Figure 2A:
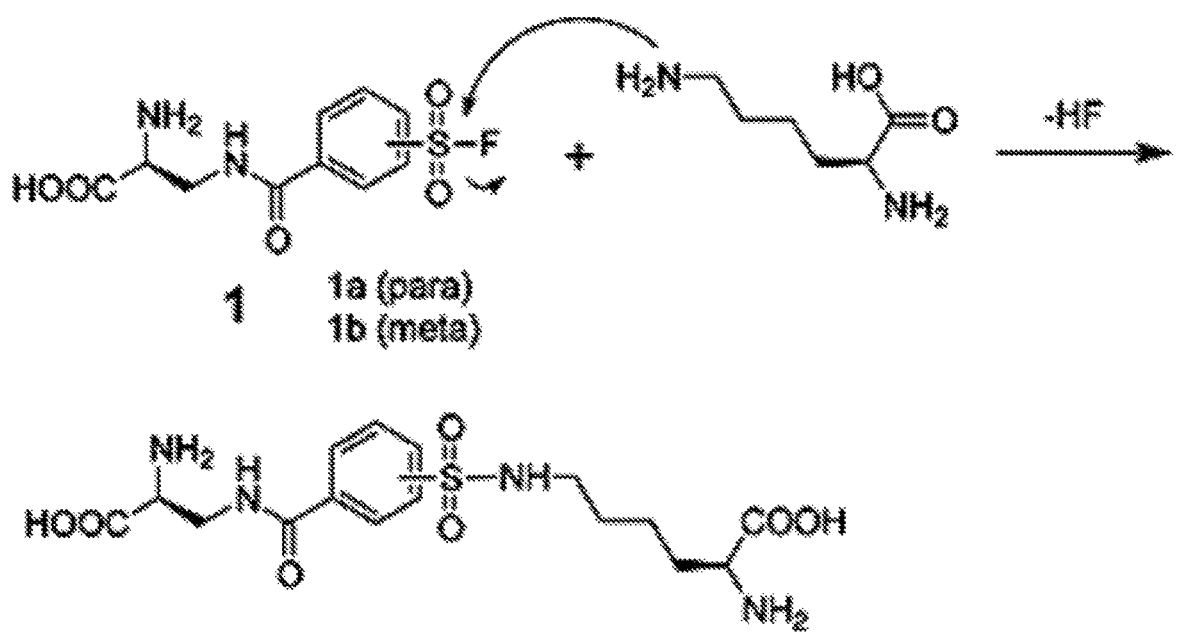
FIGS. 2A-2D.
Figure 2B:
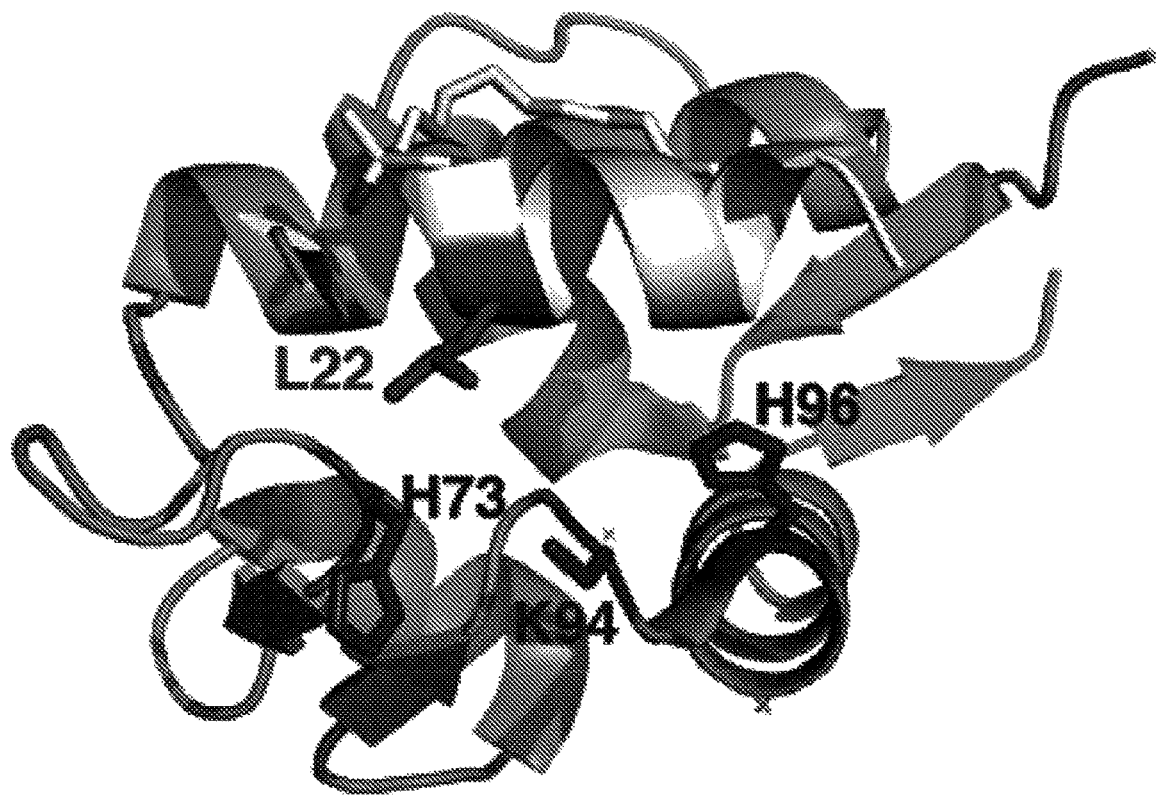
Figure 2B:
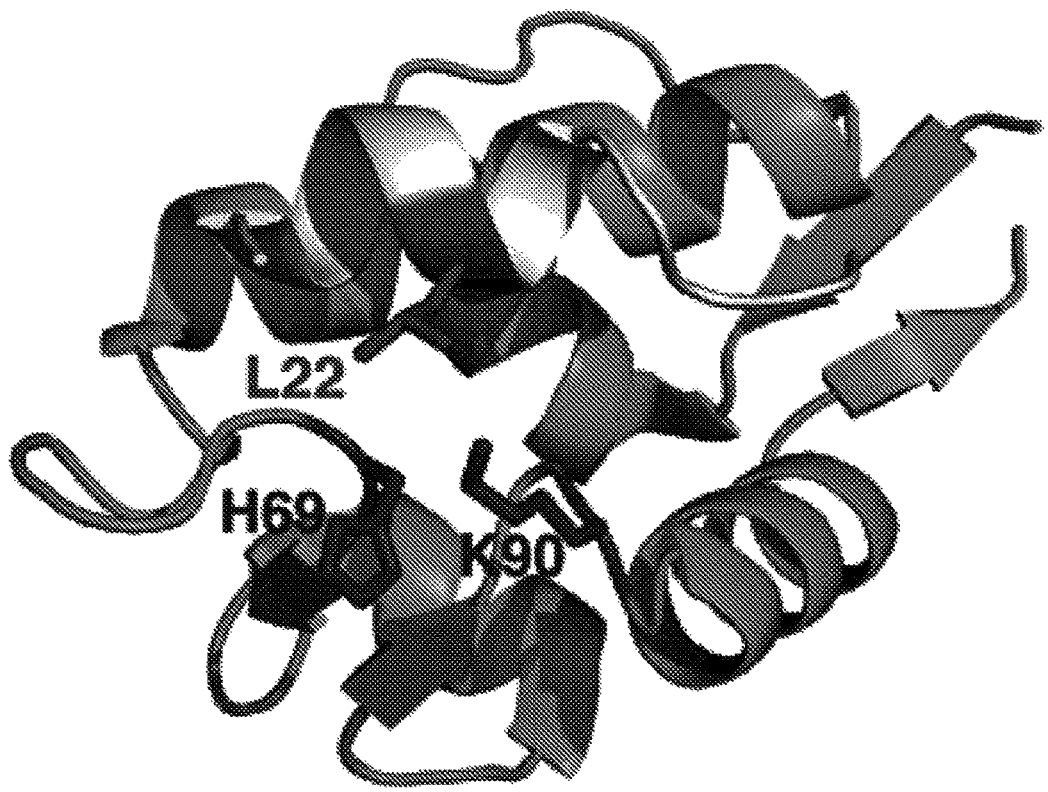
Figure 2C:
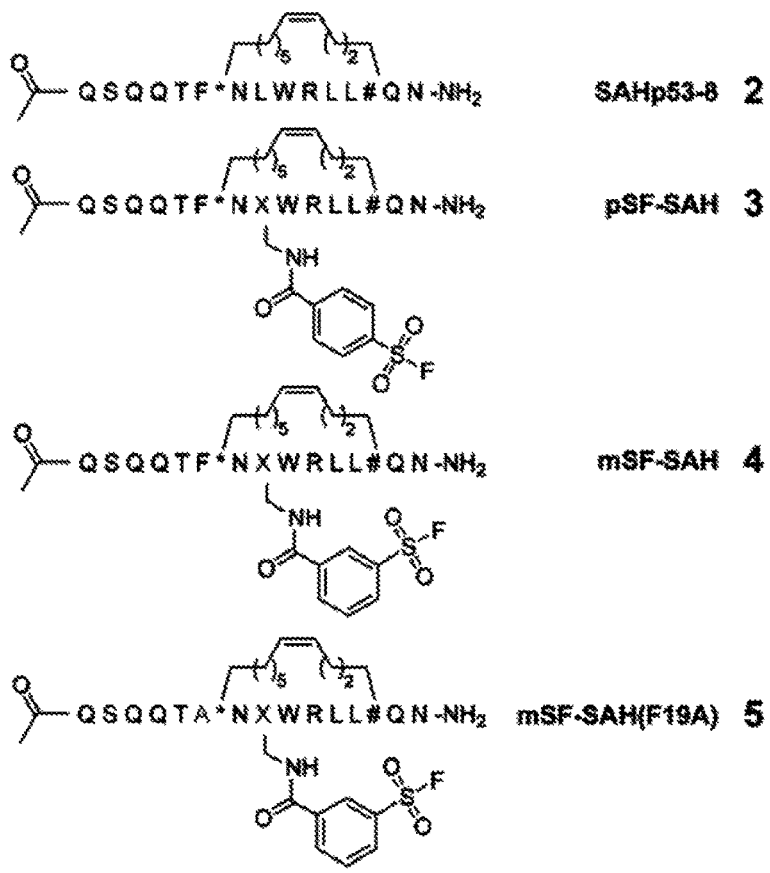
Figure 2D:
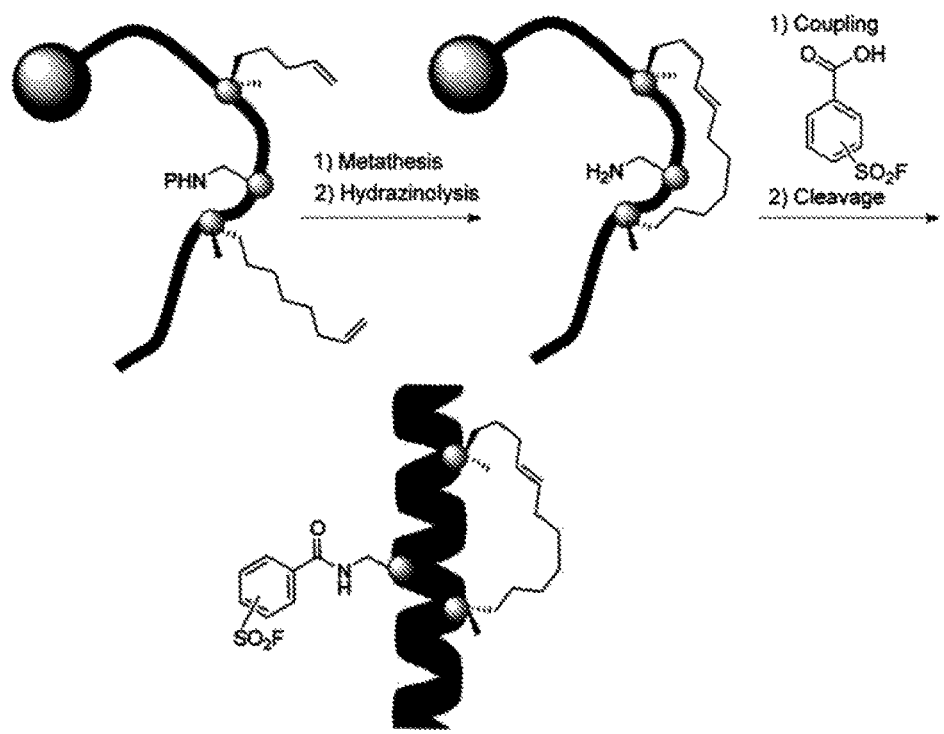
Figure 6:
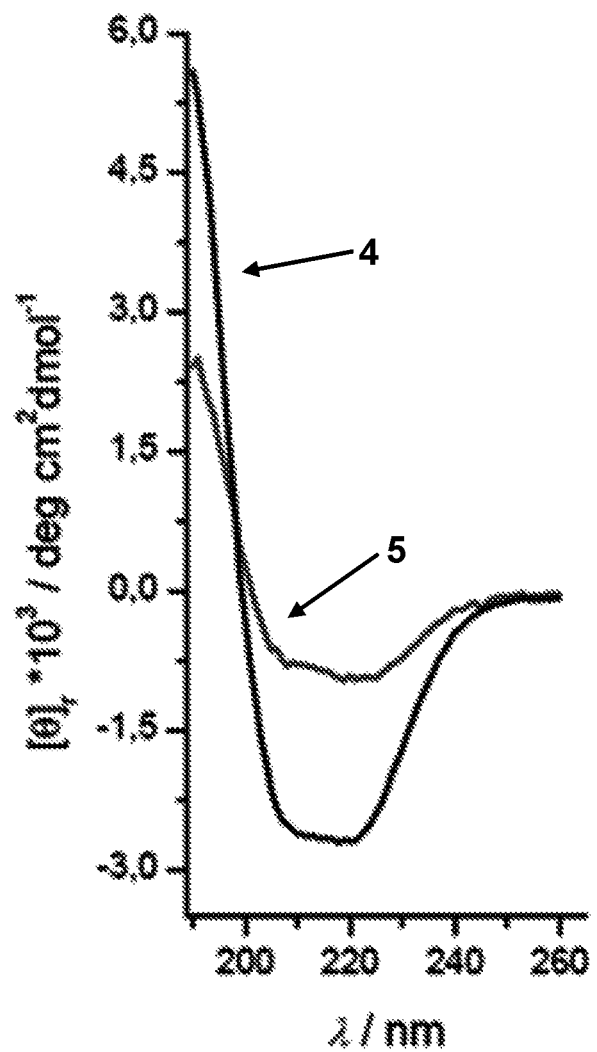
FIG. 6. The figure depicts circular dichroism (CD) spectra of 4 and 5, as indicated, showing typical shapes for α-helical conformation. CD spectra were recorded on a Bio-Logic MOS450 spectropolarimeter in Na-phosphate (10 mM) buffer containing NaF (100 mM) and at pH 7.5 using a 0.1 cm quartz cuvette (Helma) at 25° C.

To enable a stapled peptide to bind Mdm2 or Mdm4 covalently, we designed the aryl sulfonyl fluoride ($Ar-SO_2F$) unnatural amino acid (Uaa 1, FIG. 2A) and incorporated it into the SAHp53-8 peptide that inhibits p53-Mdm2/4 interactions, expecting that Uaa 1 can react with Lys or His at the binding interface of Mdm2 or Mdm4 upon binding of SAHp53-8 (FIG. 2B). We chose to work with the SAHp53-8 peptide because it has been extensively studied and crystal structures of this peptide binding with Mdm2/Mdm4 are available to guide design [6,7,25]. Previously, photocrosslinking has been used to crosslink a BH3 derived stapled peptide to proteins, but the required UV light activation can be incompatible for in vivo applications [26]. The reactivity of aryl sulfonyl fluoride was initially tested using amino acids, and it allowed crosslinking to lysine and histidine of high concentrations as analyzed by HPLC-MS. Based on the crystal structures of Mdm2 in complex with SAHp53-8 and of Mdm4 in complex with the p53 transactivation peptide (FIG. 2B), we decided to incorporate 1 into the SAHp53-8 peptide replacing the leucine at position 22 (L22) (FIG. 2B) [25]. Lysine and histidine of Mdm2 or Mdm4 in close proximity to L22 are potential candidates for reacting with Uaa 1 (FIG. 2B). Peptides were synthesized using standard protocols of peptide synthesis. The aryl sulfonyl fluoride moiety was introduced by coupling 3-(fluorosulfonyl)benzoic acid to the amino side chain of diaminopropionic acid (Dap). Final cleavage and purification gave the stapled peptides (FIG. 2D). CD spectroscopic measurements confirmed the α-helical conformation for the stapled peptides (FIG. 6).

Figure 3A:
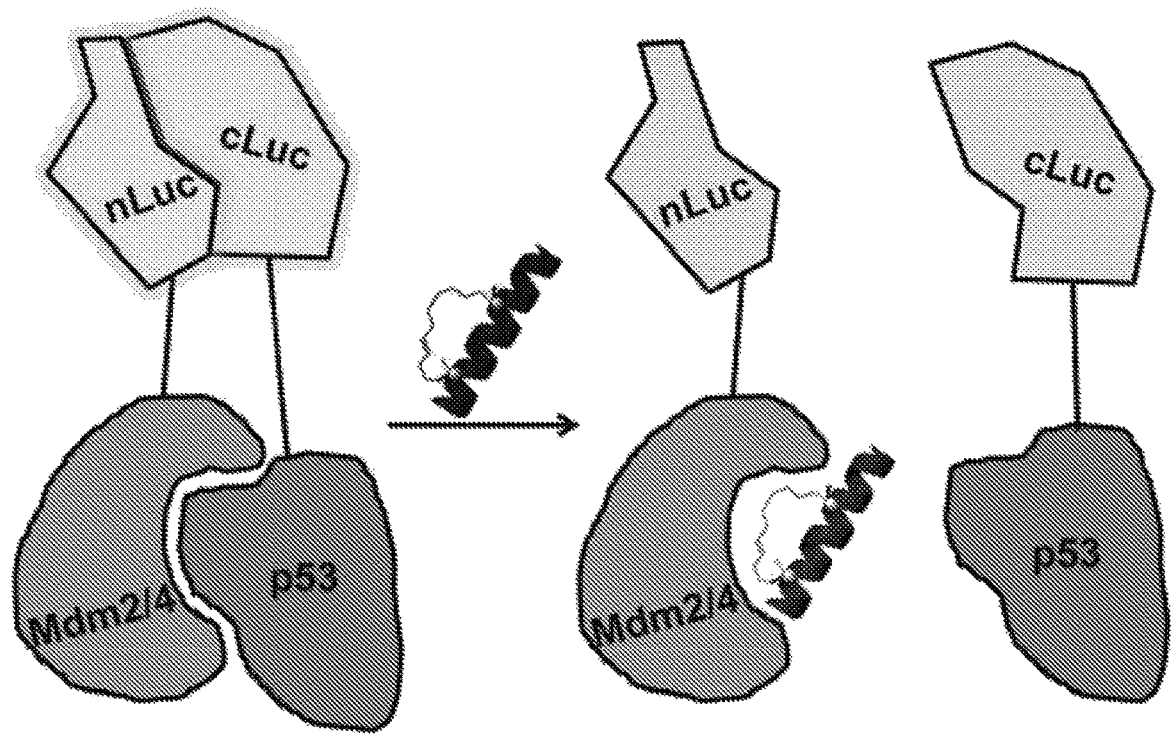

To study whether the designed stapled peptide 3 could disrupt p53-Mdm2 or p53-Mdm4 complexes more efficiently than the well-established stapled peptide 2, we measured their ability to inhibit p53-Mdm2 and p53-Mdm4 interactions in cell lysate using ReBiL (Recombinase enhanced bimolecular luciferase complementation), an assay that allows protein-protein interactions to be investigated in a more physiologically relevant context [12]. In ReBiL, luciferase is split and separately fused to Mdm2/Mdm4 and p53, and the expression cassette is integrated into a single chromosomal site in host cells (FIG. 3A). Inhibition of the interaction between p53 and Mdm2/Mdm4 results in a decrease in luciferase activity.

Figure 7A:
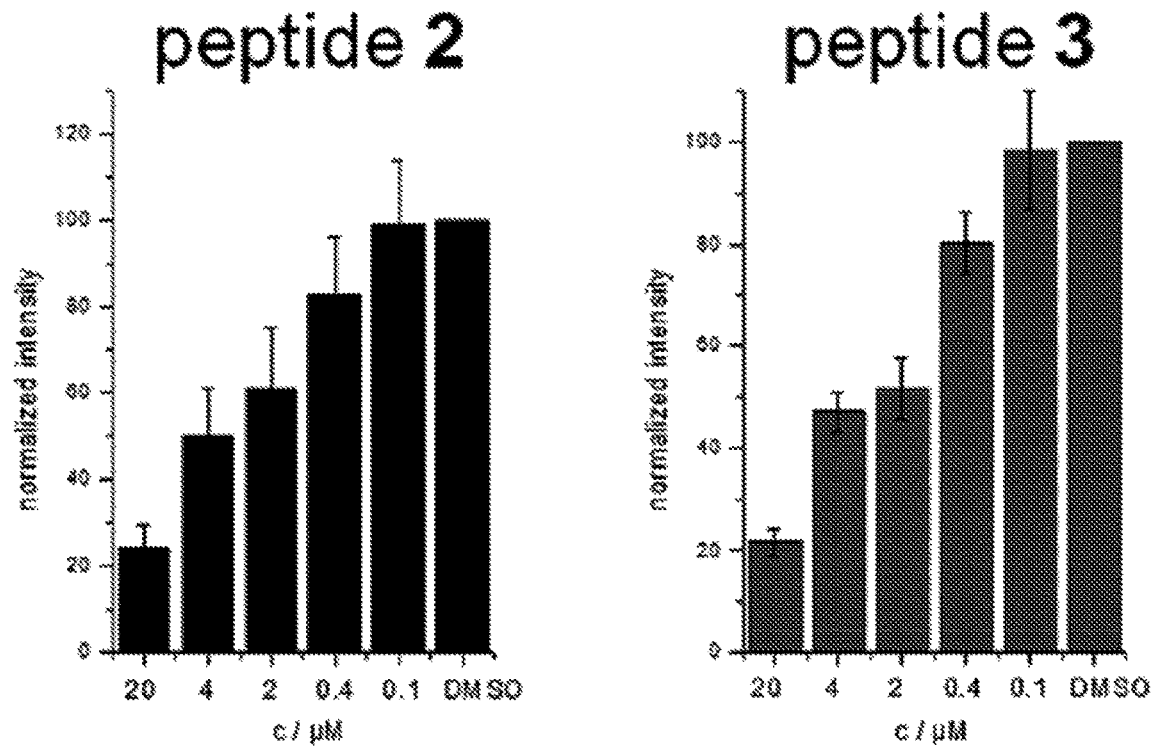
FIGS. 7A-7B. The figures depict results of ReBiL cell lysate assay showing that peptides 2 and 3 both inhibited p53-Mdm2 interaction (FIG. 7A) and p53-Mdm4 interaction (FIG. 7B) with similar activity. The assay was performed using cell lysates of Saos-2 cells. For p53-Mdm2 inhibition, IC$_{50}$=4.1 μM for peptide 2 and 2.7 μM for peptide 3; For p53-Mdm4 inhibition, IC$_{50}$=3.6 μM for peptide 2 and 3.5 μM for peptide 3. Data are shown as mean±s.e.m. (n=5) and normalized to the luminescent reading of DMSO treated cells.
Figure 7B:
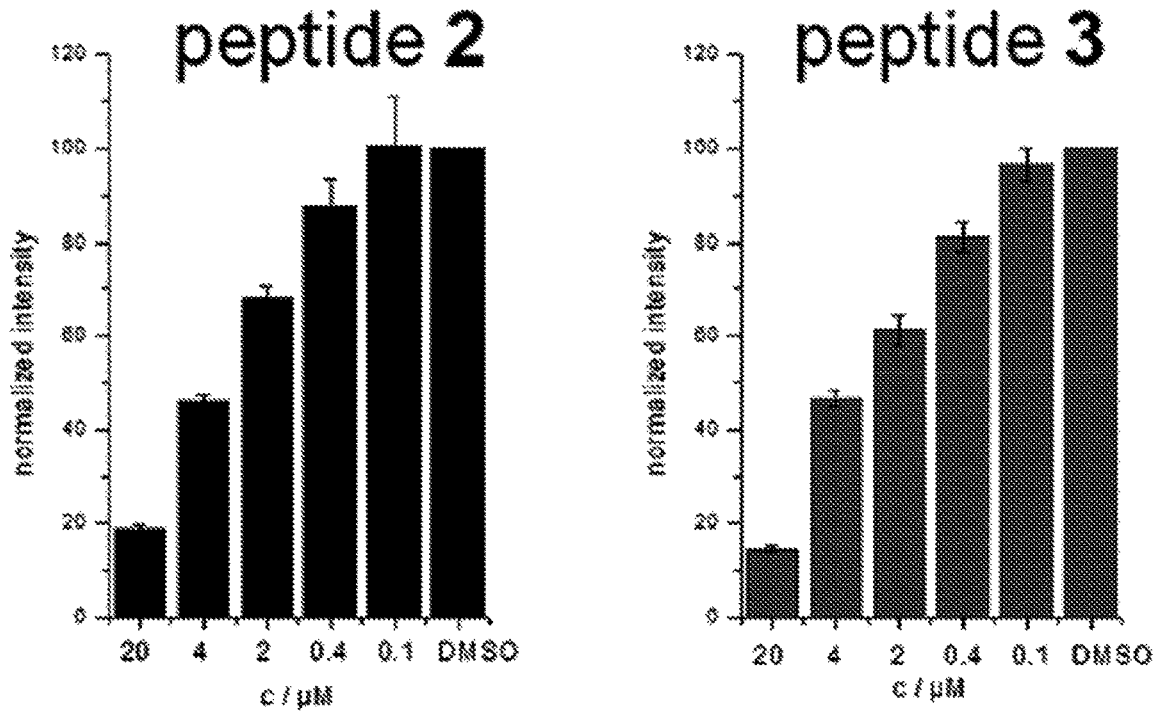

Lysates of Saos-2 cancer cells harboring ReBiL system expressing either p53-Mdm2 or p53-Mdm4 complexes were incubated with peptides 2 and 3 separately for 60 minutes at r.t. As expected, stapled peptide 2 was measured to inhibit the interaction of p53-Mdm2 with an $IC_{50}$ of 4.1 µM and of p53-Mdm4 with an $IC_{50}$ of 3.6 µM. Peptide 3 was found to be a potent inhibitor as well, disrupting p53-Mdm2 with an $IC_{50}$ of 2.7 µM and p53-Mdm4 with an $IC_{50}$ of 3.5 µM (FIGS. 7A-7B). However, the sulfonyl fluoride installed on peptide 3 did not increase its inhibiting activity significantly. Nonetheless, these results suggest that the replacement of Leu22 with the aryl sulfonyl fluoride Uaa was tolerated and did not attenuate the peptide activity.

Figure 3B:
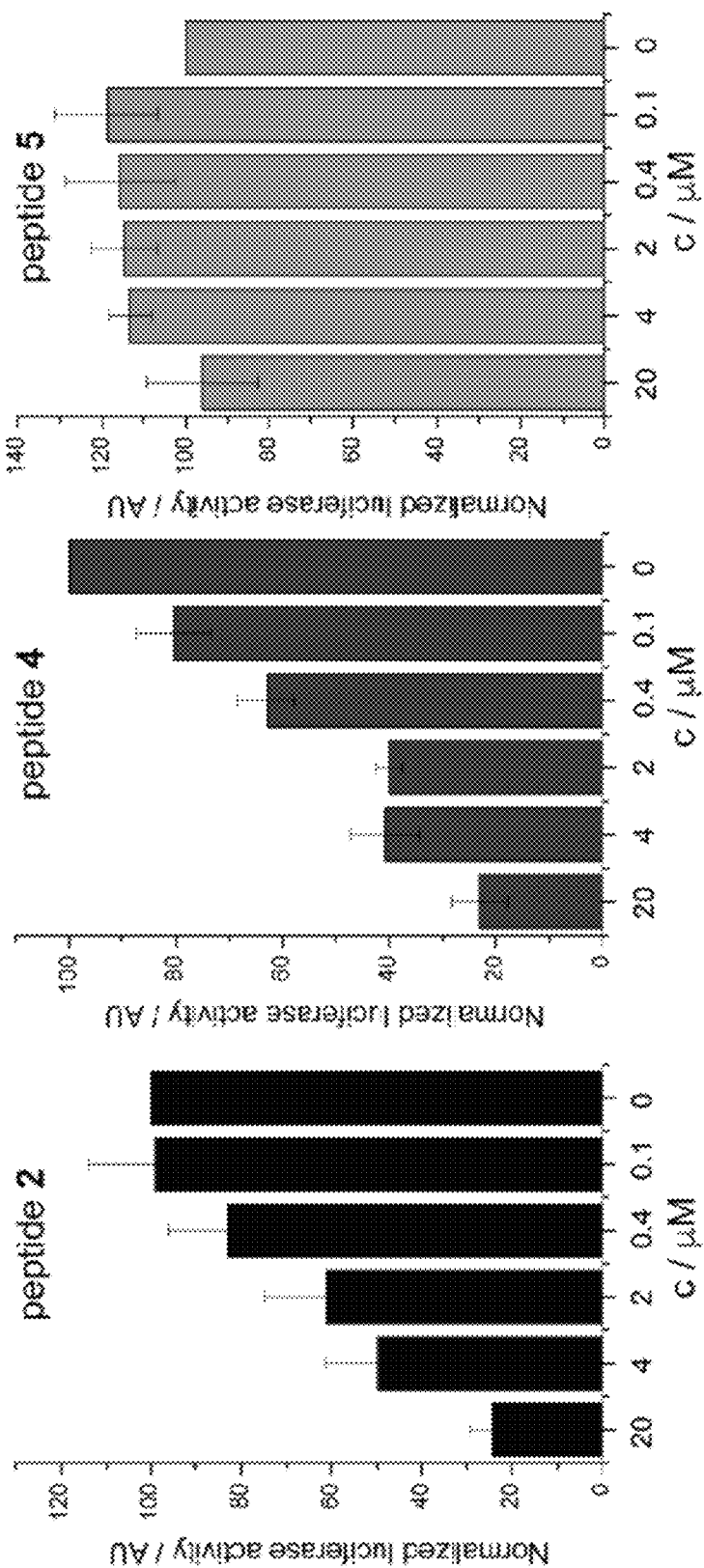
Figure 3C:
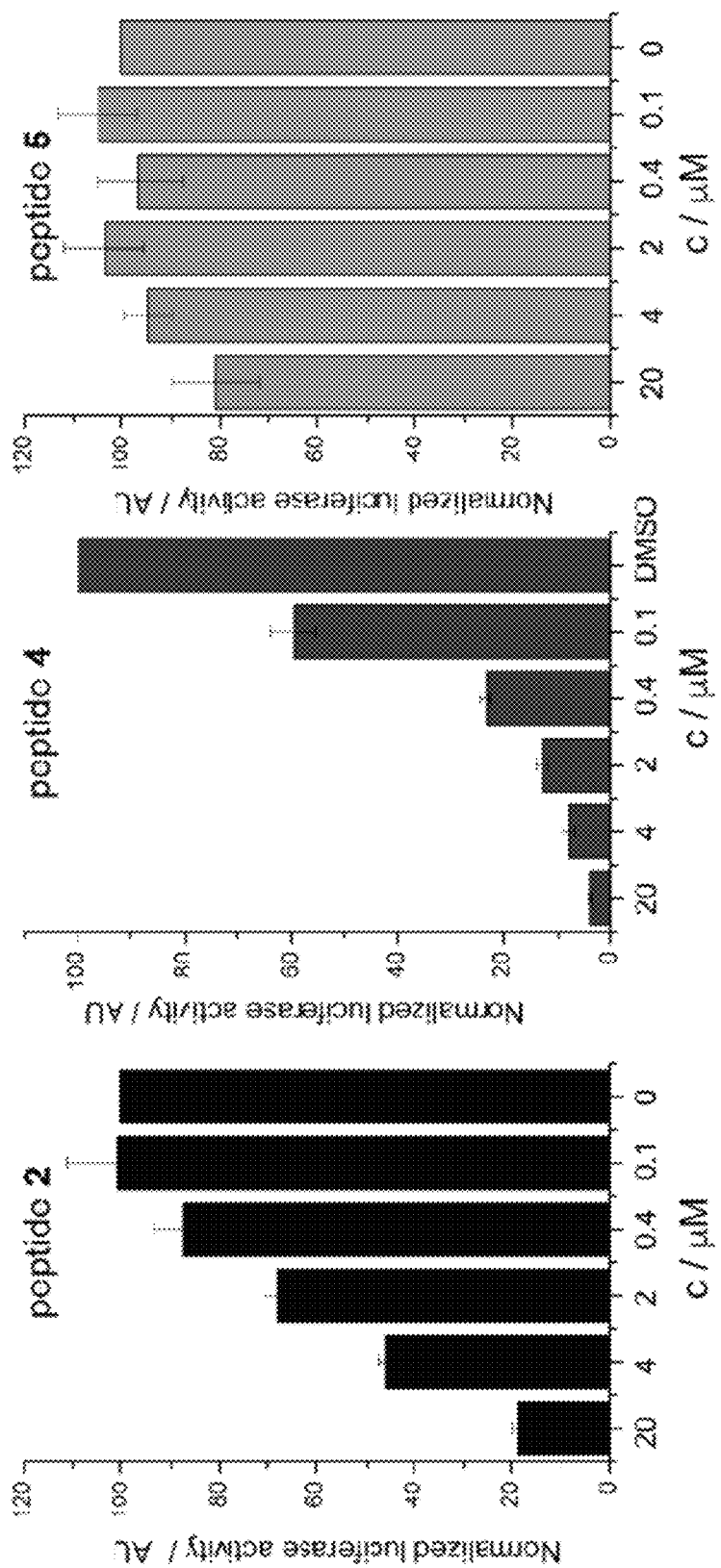
Figure 8A:
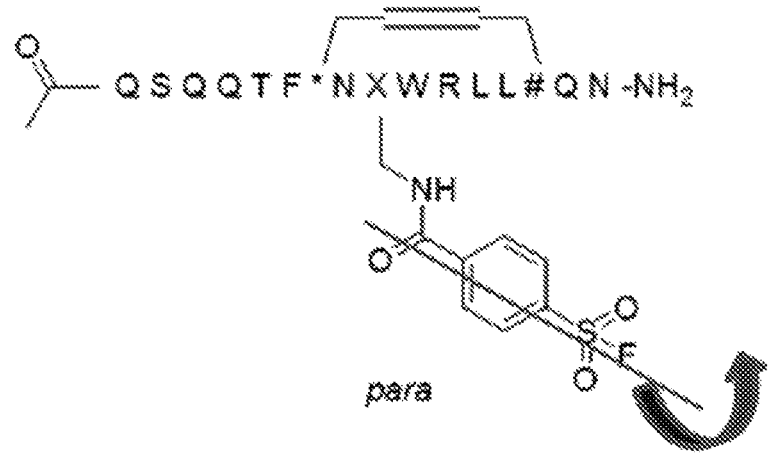
FIGS. 8A-8B. The figures demonstrates that substitution of the —SO$_2$F group on the meta position (FIG. 8B) can afford more flexibility and accessibility than the para position (FIG. 8A) in reaching and reacting with lysine or histidine side chain in proximity.
Figure 8B:
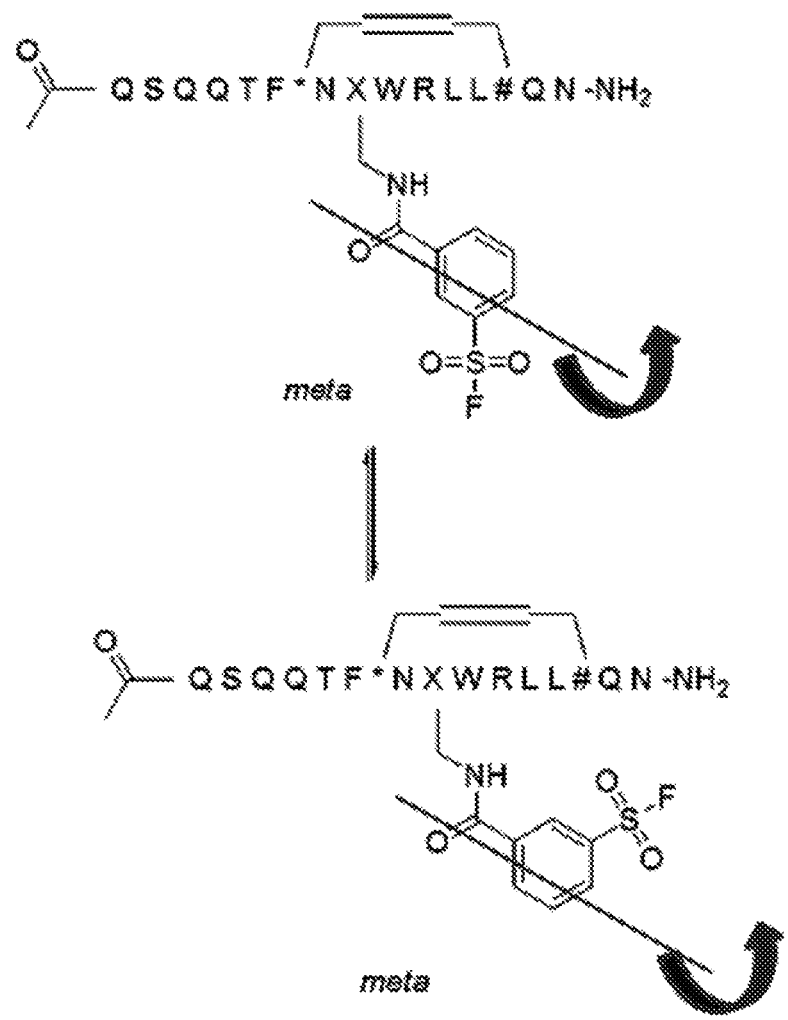

The $-SO_2F$ group in peptide 3 was installed on the Uaa at the para position of the phenyl ring. We reasoned that meta-substitution of the $-SO_2F$ group on the Uaa would afford more conformational accessibility to facilitate crosslinking to appropriately distanced residues (FIGS. 8A-8B). We therefore synthesized peptide 4 and measured its activity using ReBiL. In comparison with peptide 2 ($IC_{50}$=4.1 µM), peptide 4 ($IC_{50}$=1.3 µM) showed increased activity in inhibiting p53-Mdm2 (FIG. 3B). However, when incubating the peptides with cell lysates harboring p53-Mdm4, the stapled peptide 4 inhibited p53-Mdm4 interaction much more efficiently than the parental SAHp53-8 peptide 2, with $IC_{50}$ improved by one order of magnitude from 3.6 µM for 2 to 0.2 µM for 4 (FIG. 3C). As a negative control, peptide 5 was synthesized, in which phenylalanine 19 was mutated to alanine to abolish binding [7]. This peptide did not show any activity in inhibiting p53-Mdm2 or p53-Mdm4 (FIGS. 3B-3C), indicating that the measured activity of peptide 4 was dependent on binding with the target protein.

To test the binding selectivity of peptides 2, 4 and 5, we then incubated the peptides with cell lysates of Saos-2 cells harboring ReBiL system expressing Brca1-Bard1 instead of p53-Mdm2/Mdmx [12]. All three peptides did not inhibit the Brca1-Bard1 interaction (FIG. 3D), indicating that peptides 2 and 4 selectively bind Mdm2/Mdm4. The activity of the stapled peptide 4 to Mdm4 is ten-fold higher than to Mdm2, possibly due to a favored orientation between the peptide ligand and Mdm4 after leucine 22 is substituted by the bulky Uaa 1b [9]. Altogether these results show that the performance of the stapled SAHp53-8 peptide can be significantly improved by installing the Ar—SO$_2$F "click" function.

Figure 4:
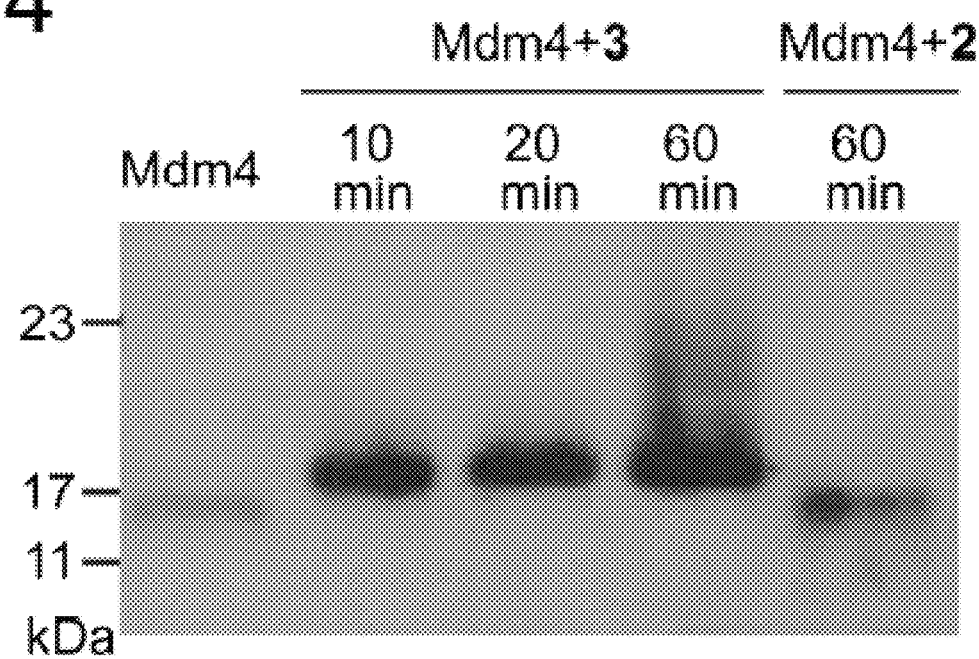
FIG. 4. The stapled peptide 4 bound Mdm4 covalently. Immunoblot showing peptide 4 upshifted Mdm4 to a higher molecular weight after binding. His-tagged Mdm4 (1.5 μM) was incubated with 2 or 4 (3 μM) separately in PBS buffer (pH 7.5) for different time. After separation by SDS-PAGE, an anti-His antibody was used to detect Mdm4. Binding of peptide 4, but not peptide 2, shifted the Mdm4 band to a higher molecular weight, suggesting covalent binding of 4 to Mdm4.
Figure 5:
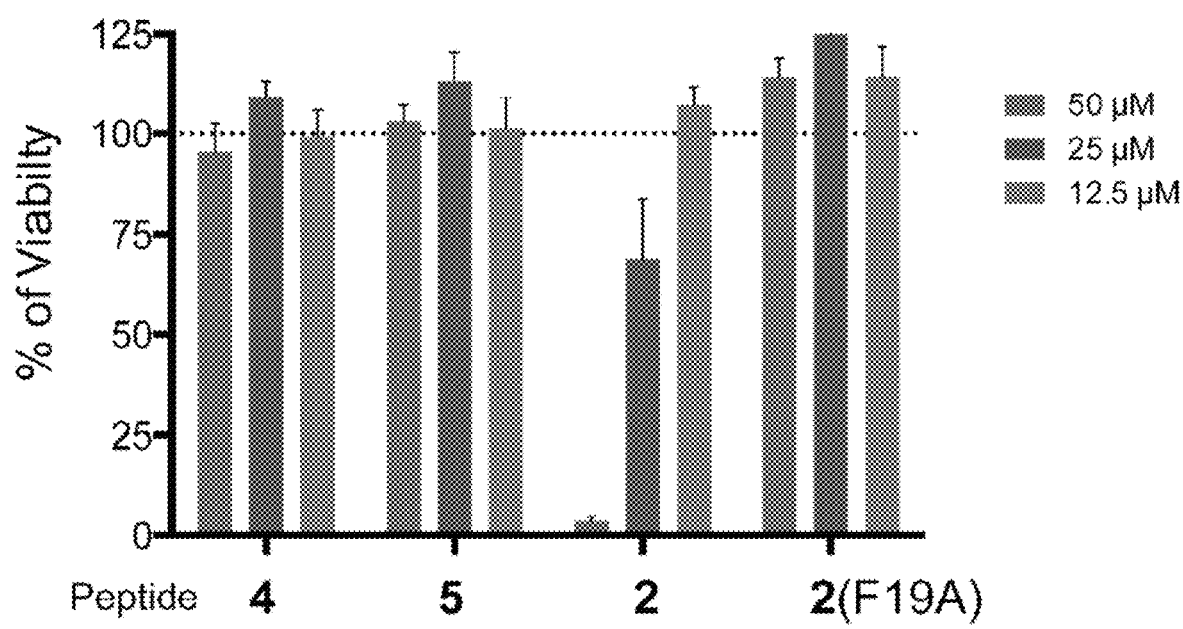
FIG. 5. Histogram depicting cell viability of Saos-2 reporter cells showed no significant cytotoxicity of the stapled peptide 4. Error bars are s.e.m. (n=5) and normalized to the luminescence reading of DMSO treated cells. For each bin, the concentration of reagents was 50, 25, or 12.5 uM, left to right, respectively.

To verify if the peptide 4 binds with Mdm4 covalently, we incubated purified Mdm4 and 4 at 37° C. in PBS buffer (pH 7.5) for 10, 20 and 60 min and detected the crosslinking reaction by immunoblotting the His-tagged Mdm4 using an anti-His antibody (FIG. 4). Already, after 10 min the "sulfate click reaction" was complete as indicated by the shift of the band to a higher molecular weight. No band shifting was detected when Mdm4 was co-incubated with SAHp53-8 (2). In addition, ESI-MS analysis of the reaction product confirmed the covalent complex formation of 4 with Mdm4. The ESI-MS spectrum (triplicate) of His-tagged Mdm4 was obtained; [M+H]$^+$=16971.63 Da. The ESI-MS analysis (triplicate) of Mdm4 incubated with 4 (for 60 min), confirming the covalent addition of the stapled peptide 4. [M+4-HF+H]$^+$=19219.76 Da. Crosslinking of 4 results in a loss of HF. The His-tagged Mdm4 showed a mass peak at 16971.63 Da. After incubation of Mdm4 with 4, a peak at 19219.76 Da was observed corresponding to the mass of the stapled peptide covalently conjugated to Mdm4.

To evaluate potential p53-independent cytotoxicity of the peptides, peptides 2 and 4 and their F19A mutants were separately incubated with the p53 null Saos-2 cells to measure cell viability. Peptide 2 reduced cell viability at increasing concentration, consistent with what was reported [12]. In contrast, peptide 4 was nontoxic to the p53 null reporter cells.

In summary, we have developed a new strategy for generating covalent peptide inhibitors via proximity-enabled bioreactivity. The peptide, upon binding, is able to form a covalent linkage with its target protein by sulfur fluoride exchange (SuFEx) of the embedded Uaa bearing aryl sulfonyl fluoride. Using this strategy we increased the inhibition activity of the stapled SAHp53-8 peptide to Mdm4 by 10-fold without being cytotoxic. Our concept and findings can be valuable for developing covalent macromolecular inhibitors of physiologically relevant protein interactions as biotherapeutics.

EXPERIMENTAL

Reagents.

His tagged Mdm4 was purchased from Sino Biological Inc. (cat. Number 15395-H07E-10). Reagents and amino acids for peptide synthesis were purchased from ChemImpex, Novabiochem (Merck) or Sigma. Alkenyl amino acids were purchased from AAPPTec.

Reactivity of Ar—SO$_2$F to Lysine and Histidine.

To test the reactivity of Ar—SO$_2$F towards lysine and histidine, we initially used Uaa 6. Both lysine and histidine reacted with the Ar—SO$_2$F amino acid 6 forming the product with high purity, as judged by HPLC-MS analyses. Because of the reactivity of the —SO$_2$F group in 6 to nucleophilic attack by piperidine, direct incorporation of 6 into peptides using Fmoc-based solid phase peptide synthesis failed. To overcome this observation, we designed Uaa 1a,b, the —SO$_2$—F group of which is introduced after complete assembly of the peptide chain on solid support.

Peptide Synthesis.

The stapled peptides were synthesized on a 0.3 mmol scale by standard protocols using Fmoc chemistry. As solid support a Rink amide resin was used (Novabiochem Rink Amide MBHA resin, 100-200 mesh, loading=0.6 mmole/g). Fmoc amino acids were coupled in five-fold excess with HBTU/DIEA (1:2) in DMF for 30 min. The Fmoc-protected olefin building blocks were coupled in 2.5-fold excess using HBTU/DIEA (1:1) in DMF for 45 min. Fmoc deprotection was realized by treating the peptide-bound resin with 20% (v/v) piperidine/DMF for 15 min. After assembly of the linear peptide chain the N-terminus of 2, 3, 4 and 5 was acetylated using a solution of acetic anhydride and DIEA in DMF. Ring-closing metathesis (RCM) was performed as described previously [51]. After assembly, peptides were treated with 4% N$_2$H$_4$ solution in order to remove ivDde and subsequently 3-(fluorosulfonyl)benzoic acid was coupled to the amino side chain of diaminopropionic acid (Dap) using five-fold excess with PyBOP/DIEA (1:2) in DMF for 30 min. 3-(fluorosulfonyl)benzoic acid was prepared previously according to the procedure from ref$^1$ by adding 3-(chlorosulfonyl)benzoic acid to a solution of KF/HF for 1 h. Final deprotection and cleavage of the peptides from the resin was realized using TFA/H2O/TIS (85/5/5, v/v). Crude peptides were precipitated by the addition of cold diethyl ether and purified on a reversed-phase C18 column (WATERS XBRIDGE™ Prep C18). Composition and purity of the stapled peptides was confirmed by LC-MS mass spectrometry using a C18 column (Phenomenex, Gemini). ESI-MS (peptide 2)=(ES+) [M+2H]$^{2+}$=calcd: 1055.3 (monoisotopic); obsd: 1055.4; ESI-MS (peptide 3)=(ES+) [M+2H]$^{2+}$=calcd: 1134.4 (monoisotopic); obsd: 1134.6; ESI-MS (peptide 4)= (ES+) [M+2H]$^{2+}$=calcd: 1134.4 (monoisotopic); obsd: 1134.6; ESI-MS (peptide 5)=(ES+) [M+2H]$^{2+}$=calcd: 1096.4 (monoisotopic); obsd: 1096.6.

ReBiL Assay.

ReBiL assay was essentially performed as described previously [S2]. Cellular lysates obtained from p53-Mdm2, p53-Mdm4, or Brca1-Bard1 reporter cells (Saos-2) were incubated with peptides in the presence of serum (FBS) in a 384-well plate at room temperature for 60 minutes. STEADY-GLO® was added, and luminescence was read in a Tecan M200 luminometer at 26° C. Mass spectrometric analyses of Mdm4 samples were performed as previously described [S3]. Cell viability was measured on the p53-null Saos-2 cells by CELL TITER-GLO® assay per Promega's instructions. Peptides were incubated with the Saos-2 cells at 37° C. for 8 h.

REFERENCES (EXAMPLE 1)

[1] M. Wade, Y. C. Li, G. M. Wahl, Nat. Rev. Cancer 2013, 13, 83-96; [2] C. J. Brown, S. Lain, C. S. Verma, A. R. Fersht, D. P. Lane, Nat. Rev. Cancer 2009, 9, 862-873; [3] D. G. Kirsch, M. B. Kastan, J. Clin. Oncol. 1998, 16, 3158-3168; [4] A. Ventura, D. G. Kirsch, M. E. Mclaughlin, D. A. Tuveson, J. Grimm, L. Lintault, J. Newman, E. E. Reczek, R. Weissleder, T. Jacks, Nature 2007, 445, 661-665; [5] M. Wade, G. M. Wahl, Mol. Cancer Res. 2009, 7, 1-11; [6] F. Bernal, M. Wade, M. Godes, T. N. Davis, D. G. Whitehead, A. L. Kung, G. M. Wahl, L. D. Walensky, Cancer Cell 2010, 18, 411-422; [7] F. Bernal, A. F. Tyler, S. J. Korsmeyer, L. D. Walensky, G. L. Verdine, J. Am. Chem. Soc. 2007, 129, 2456-2457; [8] C. J. Brown, S. T. Quah, J. Jong, A. M. Goh, P. C. Chiam, K. H. Khoo, M. L. Choong, M. A. Lee, L. Yurlova, K. Zolghadr, T. L. Joseph, C. S. Verma, D. P. Lane, ACS Chem. Biol. 2013, 8, 506-512; [9] Y. S. Chang, B. Graves, V. Guerlavais, C. Tovar, K. Packman, K. H. To, K. A. Olson, K. Kesavan, P. Gangurde, A. Mukherjee, T. Baker, K. Darlak, C. Elkin, K. Filipovic, F. Z. Qureshi, H. Cai, P. Berry, E. Feyfant, X. E. Shi, J. Horstick, D. A. Annis, A. M. Manning, N. Fotouhi, H. Nash, L. T.

Vassilev, T. K. Sawyer, Proc. Natl. Acad. Sci. U.S.A 2013, 110, 3445-3454; [10] P. M. Cromm, J. Spiegel, T. Grossmann, ACS Chem. Biol. 2015, 10, 1362-1375; [11] L. D. Walensky, G. H. Bird, J. Med. Chem. 2014, 57, 6275-6288; [12] Y.-C. Li, L. W. Rodewald, C. Hoppmann, E. T. Wong, S. Lebreton, P. Safar, M. Patek, L. Wang, K. F. Wertman, G. M. Wahl, Cell Reports 2014, 9, 1946-1958; [13] B. X. Tan, C. J. Brown, F. J. Ferrer, T. Y. Yuen, S. T. Quah, B. H. Chan, A. E. Jansson, H. L. Teo, P. Nordlund, D. P. Lane, Sci. Rep. 2015, 10, 12116; [14] Q. Chu, R. E. Moellering, G. J. Hilinski, Y.-W. Kim, T. N. Grossmann, J. T.-H. Yeh, G. L. Verdine, Med. Chem. Commun. 2015, 6, 111-119; [15] J. Singh, R. C. Petter, T. A. Baillie, A. Whitty, Nat. Rev. Drug Dis. 2011, 10, 307-317; [16] (a) Y. Takaoka, A. Ojida, I. Hamachi, Angew. Chem. Int. Ed. 2013, 52, 4088-4106; (b) U. Reinhardt, J. Lotze, S. Zernia, K. Mori, A. G. Beck-Sickinger, O. Seitz, Angew. Chem. Int. Ed. 2014, 53, 10237-10241; [17] Z. Xiang, H. Ren, Y. S. Hu, I. Coin, J. Wei, H. Cang, L. Wang, Nat Methods 2013, 10, 885-888; [18] I. Coin, V. Katritch, T. Sun, Z. Xiang, F. Y. Siu, M. Beyermann, R. C. Stevens, L. Wang, Cell 2013, 155, 1258-1269; [19] X.-H. Chen, Z. Xiang, Y. S. Hu, V. K. Lacey, H. Cang, L. Wang, ACS Chem. Biol. 2014, 9, 1956-1961; [20] J. L. Furman, M. Kang, S. Choi, Y. Cao, E. D. Wold, S. B. Sun, V. V. Smider, P. G. Schultz, C. H. Kim, J. Am. Chem. Soc. 2014, 136, 8411-8417; [21] J. Dong, L. Krasnova, M. G. Finn, K. B. Sharpless, Angew. Chem. Int. Ed. 2014, 53, 9430-9448; [22] N. P. Grimster, S. Connelly, A. Baranczak, J. Dong, L. B. Krasnova, K. B. Sharpless, E. T. Powers, I. A. Wilson, J. W. Kelly J. Am. Chem. Soc. 2013, 135, 5656-68; [23] A. Narayanan, L. H. Jones, Chem. Sci. 2015, 6, 2650-2659; [24] A. J. Brouwer, A. Jonker, P. Werkhoven, E. Kuo, N. Li, N. Gallastegui, J. Kemmink, B. I. Florea, M. Groll, H. S. Overkleeft, R. M. Liskamp, J. Med. Chem. 2012, 55, 10995-11003; [25] S. Baek, P. S. Kutchukian, G. L. Verdine, R. Huber, T. A. Holak, K. W. Lee, G. M. Popowicz, J. Am. Chem. Soc. 2012, 134, 103-106; [26] C. R. Braun, J. Mintseris, E. Gavathiotis, G. H. Bird, S. P. Gygi L. D. Walensky, Chem. Biol. 2010, 17, 1325-1333; [51] Kim, Y.-W.; Grossmann, T. N.; Verdine, G. L. Nat. Prot. 2011, 6, 761-771; [S2] Li, Y.-C.; Rodewald, L. W.; Hoppmann, C.; Wong, E. T.; Lebreton, S.; Safar, P.; Patek, M.; Wang, L.; Wertman, K. F.; Wahl, G. M. Cell Reports 2014, 9, 1946-1958; [S3] Xiang, Z.; Ren, H.; Hu, Y. S.; Coin, I.; Wei, J.; Cang, H.; Wang, L. Nat. Methods 2013, 10, 885-888.

What is claimed is:

1. A compound of Formula (IIIa):

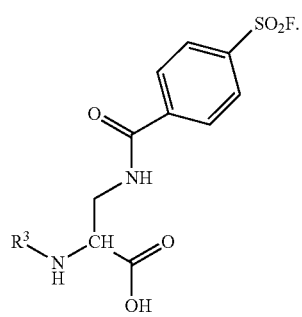

wherein $R^3$ is hydrogen or an amino protecting group.

2. A compound having the formula:

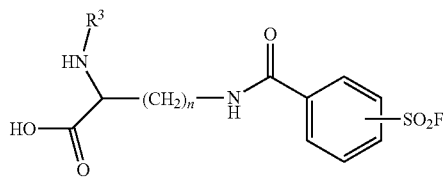

wherein $R^3$ is hydrogen or an amino protecting group, and n is an integer from 1 to 8.

3. The compound according to claim 2, wherein n is 1, 2, or 3.

4. The compound according to claim 1, wherein $R^3$ is hydrogen.

5. The compound according to claim 1, wherein $R^3$ is the amino protecting group.

6. The compound of claim 5, wherein the amino protecting group is tert-butyloxycarbonyl, 9H-fluoren-9-yl-methoxycarbonyl, benzyloxy-carbonyl, allyloxycarbonyl, 4-methyltrityl, 1-(4,4-dimethyl-2,6-dioxocyclohex-1-ylidene)-3-ethyl, or 1-(4,4-dimethyl-2,6-dioxocyclohex-1-ylidene)-3-methylbutyl.

7. The compound according to claim 2, wherein $R^3$ is hydrogen.

8. The compound according to claim 2, wherein $R^3$ is the amino protecting group.

9. The compound of claim 8, wherein the amino protecting group is tert-butyloxycarbonyl, 9H-fluoren-9-yl-methoxycarbonyl, benzyloxy-carbonyl, allyloxycarbonyl, 4-methyltrityl, 1-(4,4-dimethyl-2,6-dioxocyclohex-1-ylidene)-3-ethyl, or 1-(4,4-dimethyl-2,6-dioxocyclohex-1-ylidene)-3-methylbutyl.

* * * * *